(12) United States Patent
Basile et al.

(10) Patent No.: US 9,396,921 B2
(45) Date of Patent: *Jul. 19, 2016

(54) METHOD AND APPARATUS FOR PYROLYSIS-INDUCED CLEAVAGE IN PEPTIDES AND PROTEINS

(71) Applicant: the University of Wyoming, Laramie, WY (US)

(72) Inventors: Franco Basile, Fort Collins, CO (US); Shaofeng Zhang, Exton, PA (US)

(73) Assignee: Wyoming Research Products Center, Laramie, WY (US)

( * ) Notice: Subject to any disclaimer, the term of this patent is extended or adjusted under 35 U.S.C. 154(b) by 0 days.

This patent is subject to a terminal disclaimer.

(21) Appl. No.: 13/938,482

(22) Filed: Jul. 10, 2013

(65) Prior Publication Data

US 2014/0284466 A1 Sep. 25, 2014

Related U.S. Application Data

(60) Division of application No. 12/371,893, filed on Feb. 16, 2009, now Pat. No. 8,637,325, which is a continuation-in-part of application No. 12/307,538, filed as application No. PCT/US2007/015444 on Jul. 5, 2007.

(60) Provisional application No. 60/818,858, filed on Jul. 6, 2006.

(51) Int. Cl.
| | |
|---|---|
| *B01D 59/44* | (2006.01) |
| *H01J 49/04* | (2006.01) |
| *C07K 1/12* | (2006.01) |
| *G01N 33/68* | (2006.01) |
| *H01J 49/14* | (2006.01) |
| *H01J 49/26* | (2006.01) |

(52) U.S. Cl.
CPC ............. *H01J 49/0468* (2013.01); *C07K 1/12* (2013.01); *G01N 33/6848* (2013.01); *H01J 49/0472* (2013.01); *H01J 49/142* (2013.01); *H01J 49/26* (2013.01); *Y10T 436/24* (2015.01); *Y10T 436/25* (2015.01)

(58) Field of Classification Search
CPC ... C07K 1/12; G01N 33/6848; H01J 49/0468; H01J 49/0472; H01J 49/142; H01J 49/26; Y10T 436/24; Y10T 436/25
See application file for complete search history.

(56) References Cited

U.S. PATENT DOCUMENTS

| | | | | |
|---|---|---|---|---|
| 6,600,155 | B1 * | 7/2003 | Andrien et al. | 250/287 |
| 6,908,740 | B2 * | 6/2005 | Vandekerckhove et al. | 435/7.1 |
| 8,637,325 | B2 * | 1/2014 | Basile et al. | 436/501 |
| 2010/0044560 | A1 * | 2/2010 | Basile et al. | 250/282 |
| 2011/0084203 | A1 * | 4/2011 | Basile et al. | 250/282 |
| 2013/0303729 | A1 * | 11/2013 | Basile et al. | 530/343 |

OTHER PUBLICATIONS

Hauser et al. Online Microwave D-Cleavage LC-ESI-MS/MS of Intact Proteins: Site-Specific Cleavages at Aspartic Acid Residues and Disulfide Bonds. J Proteome Research, 2008 (Published on Web Jan. 17, 2008). vol. 7, pp. 1012-1026.*

* cited by examiner

*Primary Examiner* — Marcela M Cordero Garcia
(74) *Attorney, Agent, or Firm* — Davis, Brown, Koehn, Shors & Roberts, P.C.; Kent A. Herink

(57) ABSTRACT

A method and apparatus for conducting the rapid pyrolysis of peptides, proteins, polymers, and biological materials. The method can be carried out at atmospheric pressures and takes only about 5 to 30 seconds. The samples are cleaved at the C-terminus of aspartic acid. The apparatus employs a probe on which the sample is heated and digested components analyzed.

5 Claims, 70 Drawing Sheets

Protein Summary Report

```
Format as  [Protein Summary (deprecated)]                    Help
   Significance threshold p < [0.05]    Max. number of hits [AUTO]
   Standard scoring ⊙  MudPIT scoring ○  Ions score or expect cut-off [0]   Show sub-sets [0]
   Show pop-ups ⊙  Suppress Pop-ups ○  Sort unassigned [Decreasing Score] Require bold red ☐
  [Re-Search All]  [Search Unmatched]
```

```
Index
Accession  Mass   Score  Description
1. 1HER    14290  107    Lysozyme (EC 3.2.1.17) mutant (T40S) - chicken 2. 1LSY    14276  107    Lysozyme (EC 3.2.1.17) mutant with asp 52
                         replaced by ser d52s- chicken
```

FIG. 20B

Results List

1. 1HER  Mass: 14290  Score: 87  Expect: 0.0062  Queries matched: 5
   lysozyme (EC 3.2.1.17) mutant (T40S) - chicken

| Observed | Mr(expt) | Mr(calc) | Delta | Start | End | Miss | Ions | Peptide |
   |---|---|---|---|---|---|---|---|---|
   | 605.6000 | 604.5927 | 605.3649 | -0.7722 | 1 | 5 | 0 | 10 | -.KVFGR.C |
   | 828.6000 | 827.5927 | 828.4606 | -0.8679 | 120 | 126 | 0 | 29 | D.VQAWIRG.C |
   | 1201.6000 | 1200.5927 | 1200.6550 | -0.0622 | 120 | 129 | 0 | 19 | D.VQAWIRGCRL.- |
   | 1327.6000 | 1326.5927 | 1327.6309 | -1.0382 | 15 | 29 | 0 | 40 | D.NYRGYSLGNWV.C |
   | 1434.7000 | 1433.6927 | 1434.7408 | -1.0481 | 53 | 63 | 0 | 25 | D.YGILQINSRWW.C |

2. 1LSY  Mass: 14276  Score: 87  Expect: 0.0062  Queries matched: 5
   Lysozyme (EC 3.2.1.17) mutant with asp 52 replaced by ser (d52s) - chicken

| Observed | Mr(expt) | Mr(calc) | Delta | Start | End | Miss | Ions | Peptide |
   |---|---|---|---|---|---|---|---|---|
   | 605.6000 | 604.5927 | 605.3649 | -0.7722 | 1 | 5 | 0 | 10 | -.KVFGR.C |
   | 828.6000 | 827.5927 | 828.4606 | -0.8679 | 120 | 126 | 0 | 29 | D.VQAWIRG.C |
   | 1201.6000 | 1200.5927 | 1200.6550 | -0.0622 | 120 | 129 | 0 | 19 | D.VQAWIRGCRL.- |
   | 1327.6000 | 1326.5927 | 1327.6309 | -1.0382 | 15 | 29 | 0 | 40 | D.NYRGYSLGNWV.C |
   | 1434.7000 | 1433.6927 | 1434.7408 | -1.0481 | 53 | 63 | 0 | 25 | S.YGILQINSRWW.C |

3. 1HEO  Mass: 14304  Score: 87  Expect: 0.0066  Queries matched: 5
   lysozyme (EC 3.2.1.17) mutant (T40S, S91T) - chicken

| Observed | Mr(expt) | Mr(calc) | Delta | Start | End | Miss | Ions | Peptide |
   |---|---|---|---|---|---|---|---|---|
   | 605.6000 | 604.5927 | 605.3649 | -0.7722 | 1 | 5 | 0 | 10 | -.KVFGR.C |
   | 828.6000 | 827.5927 | 828.4606 | -0.8679 | 120 | 126 | 0 | 29 | D.VQAWIRG.C |
   | 1201.6000 | 1200.5927 | 1200.6550 | -0.0622 | 120 | 129 | 0 | 19 | D.VQAWIRGCRL.- |
   | 1327.6000 | 1326.5927 | 1327.6309 | -1.0382 | 15 | 29 | 0 | 40 | D.NYRGYSLGNWV.C |
   | 1434.7000 | 1433.6927 | 1434.7408 | -1.0481 | 53 | 63 | 0 | 25 | D.YGILQINSRWW.C |

4. 2IFF  Mass: 14276  Score: 87  Expect: 0.0071  Queries matched: 5
   lysozyme (EC 3.2.1.17) c (with mouse IgG-1 Fv fragment antibody D1.3), chain Y - chicken

| Observed | Mr(expt) | Mr(calc) | Delta | Start | End | Miss | Ions | Peptide |
   |---|---|---|---|---|---|---|---|---|
   | 605.6000 | 604.5927 | 605.3649 | -0.7722 | 1 | 5 | 0 | 10 | -.KVFGR.C |
   | 828.6000 | 827.5927 | 828.4606 | -0.8679 | 120 | 126 | 0 | 29 | D.VQAWIRG.C |
   | 1201.6000 | 1200.5927 | 1200.6550 | -0.0622 | 120 | 129 | 0 | 19 | D.VQAWIRGCRL.- |
   | 1327.6000 | 1326.5927 | 1327.6309 | -1.0382 | 15 | 29 | 0 | 40 | D.NYRGYSLGNWV.C |
   | 1434.7000 | 1433.6927 | 1434.7408 | -1.0481 | 53 | 63 | 0 | 25 | D.YGILQINSRWW.C |

FIG. 20C

Index

```
   Accession  Mass  Score  Description
1. INCT       5741    38   insulin - cat
```

---

Results List

1.  INCT    Mass: 5741    Score: 38    Expect: 5.6e+02    Queries matched: 2
    insulin - cat

| Observed | Mr(expt) | Mr(calc) | Delta | Start | End | Miss | Ions | Peptide |
    |---|---|---|---|---|---|---|---|---|
    | 544.6000 | 543.5927 | 544.2857 | -0.6930 | 31 | 35 | 0 | 17 | X.GIVEQ.C |
    | 756.6000 | 755.5927 | 756.3919 | -0.7992 | 1 | 6 | 0 | 25 | -.FVNQHL.C |

Search Parameters

Type of search    : MS/MS Ion Search
Enzyme            : None
Mass values       : Monoisotopic

FIG. 22

Index

| Accession | Mass | Score | Description |
|---|---|---|---|
| 1. Q6LER6_HUMAN | 3194 | 62 | Cytochrome c (Fragment).- Homo sapiens (Human). |

Results List

1. Q6LER6_HUMAN    Mass: 3194    Score: 62    Expect: 1.9    Queries matched: 1
   Cytochrome c (Fragment).- Homo sapiens (Human).

| Observed | Mr(expt) | Mr(calc) | Delta | Start | End | Miss | Ions | Peptide |
|---|---|---|---|---|---|---|---|---|
| 1263.0000 | 1261.9927 | 1262.7234 | -0.7307 | 18 - | 28 | 0 | 64 | D.LIAYLKKATNE.- |

Search Parameters

Type of search        : MS/MS Ion Search
Enzyme               : None
Mass values          : Monoisotopic
Protein Mass        : Unrestricted
Peptide Mass Tolerance : ± 2 Da
Fragment Mass Tolerance: ± 1.5 Da
Max Missed Cleavages   : 1
Instrument type      : Default
Query1 (1263.0000,1+) : <no title>

FIG. 26

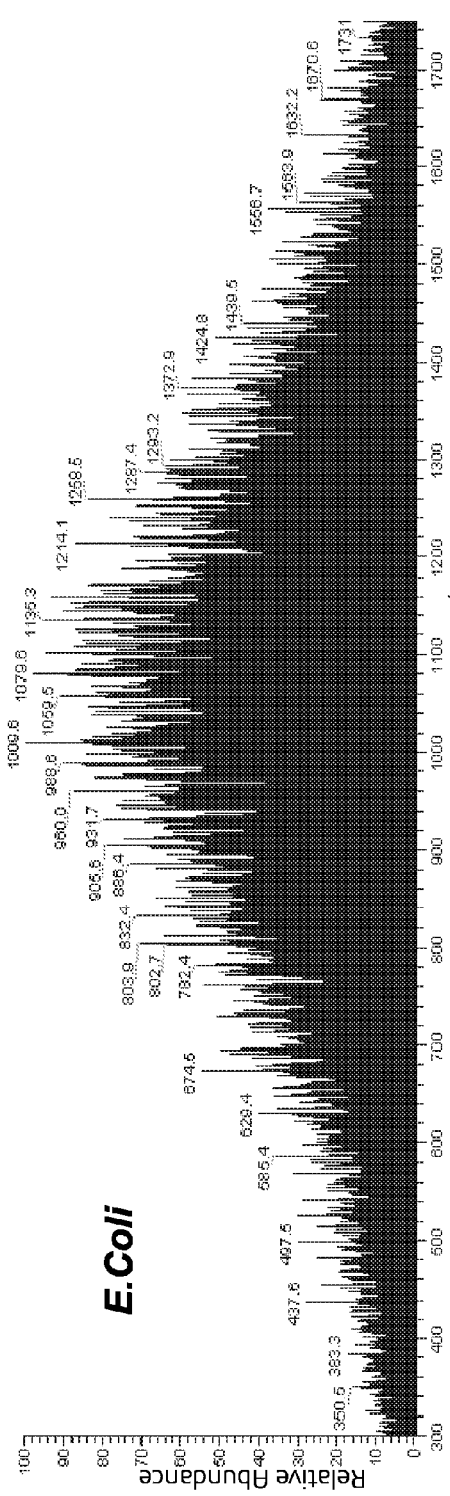
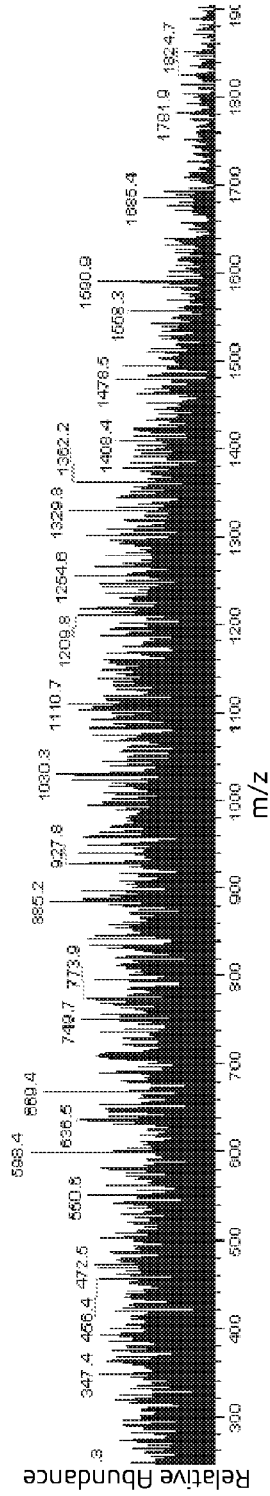
FIG. 29A
FIG. 29B

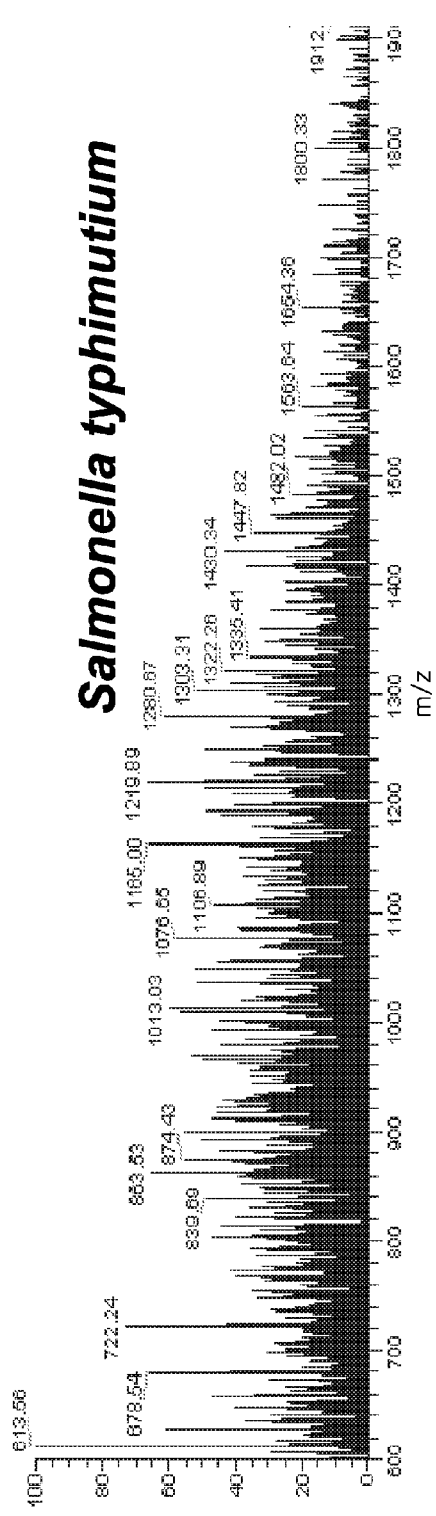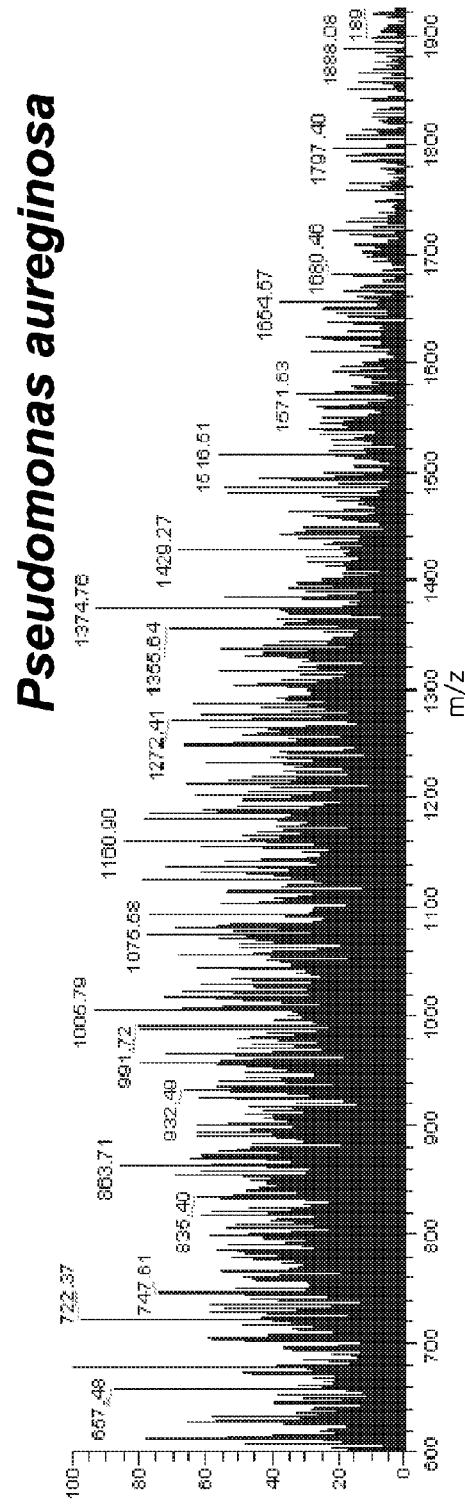

FIG. 35

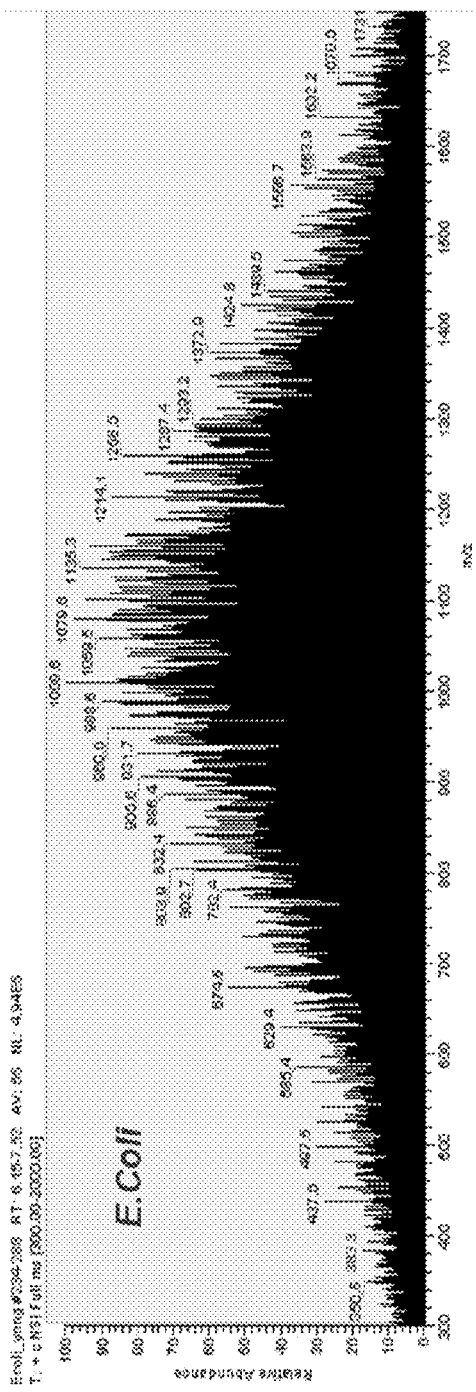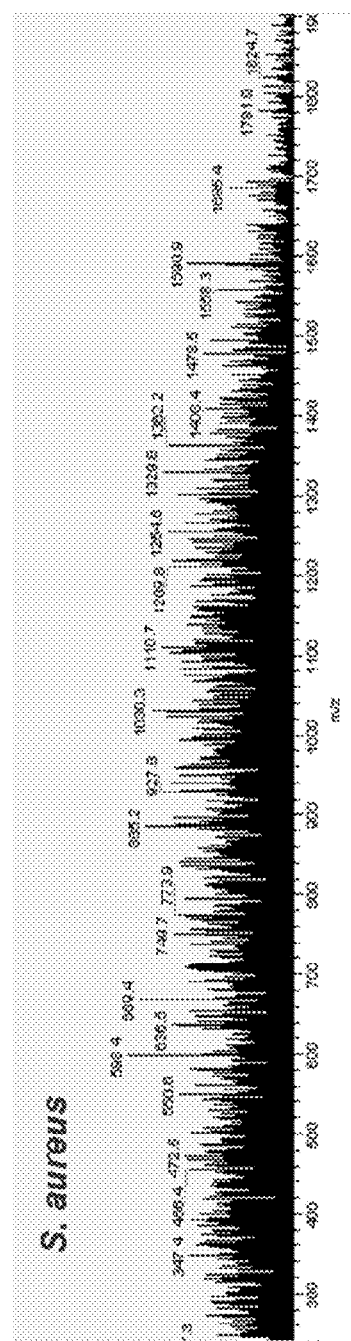
FIG. 37 A
FIG. 37 B

SEQUENCE LISTING

```
<160> NUMBER OF SEQ ID NOS: 38

<210> SEQ ID NO 1
<211> LENGTH: 8
<212> TYPE: PRT
<213> ORGANISM: Artificial Sequence
<220> FEATURE:
<223> OTHER INFORMATION: Synthetic

<400> SEQUENCE: 1

Asp Arg Val Tyr Ile His Pro Phe
1               5

<210> SEQ ID NO 2
<211> LENGTH: 12
<212> TYPE: PRT
<213> ORGANISM: Artificial Sequence
<220> FEATURE:
<223> OTHER INFORMATION: Synthetic

<400> SEQUENCE: 2

His Ser Asp Ala Val Phe Thr Asp Asn Tyr Thr Arg
1               5                   10

<210> SEQ ID NO 3
<211> LENGTH: 11
<212> TYPE: PRT
<213> ORGANISM: Artificial Sequence
```

```
<220> FEATURE:
<223> OTHER INFORMATION: Synthetic

<400> SEQUENCE: 3

Tyr Thr Asp Ile Glu Met Asn Arg Leu Gly Lys
1               5                   10

<210> SEQ ID NO 4
<211> LENGTH: 9
<212> TYPE: PRT
<213> ORGANISM: Artificial Sequence
<220> FEATURE:
<223> OTHER INFORMATION: Synthetic

<400> SEQUENCE: 4

Ala Val Phe Thr Asp Asn Tyr Thr Arg
1               5

<210> SEQ ID NO 5
<211> LENGTH: 4
<212> TYPE: PRT
<213> ORGANISM: Artificial Sequence
<220> FEATURE:
<223> OTHER INFORMATION: Synthetic

<400> SEQUENCE: 5

Asn Tyr Thr Arg
1

<210> SEQ ID NO 6
<211> LENGTH: 9
<212> TYPE: PRT
<213> ORGANISM: Artificial Sequence
<220> FEATURE:
<223> OTHER INFORMATION: Synthetic

<400> SEQUENCE: 6

Val Gln Ala Trp Arg Gly Cys Arg Leu
1               5

<210> SEQ ID NO 7
<211> LENGTH: 10
<212> TYPE: PRT
<213> ORGANISM: Artificial Sequence
<220> FEATURE:
<223> OTHER INFORMATION: Synthetic

<400> SEQUENCE: 7

Ser Tyr Ser Met Glu His Phe Arg Trp Gly
1               5                   10

<210> SEQ ID NO 8
<211> LENGTH: 6
<212> TYPE: PRT
<213> ORGANISM: Artificial Sequence
<220> FEATURE:
<223> OTHER INFORMATION: Synthetic

<400> SEQUENCE: 8

Pro His Cys Lys Arg Met
1               5

<210> SEQ ID NO 9
<211> LENGTH: 14
<212> TYPE: PRT
<213> ORGANISM: Artificial Sequence
<220> FEATURE:
```

<223> OTHER INFORMATION: Synthetic

<400> SEQUENCE: 9

Ala Gly Cys Lys Asn Phe Phe Trp Lys Thr Phe Thr Ser Cys
1               5                   10

<210> SEQ ID NO 10
<211> LENGTH: 7
<212> TYPE: PRT
<213> ORGANISM: Artificial Sequence
<220> FEATURE:
<223> OTHER INFORMATION: Synthetic

<400> SEQUENCE: 10

Arg Val Tyr Ile His Pro Phe
1               5

<210> SEQ ID NO 11
<211> LENGTH: 7
<212> TYPE: PRT
<213> ORGANISM: Artificial Sequence
<220> FEATURE:
<223> OTHER INFORMATION: Synthetic

<400> SEQUENCE: 11

Glu Met Asn Arg Leu Gly Lys
1               5

<210> SEQ ID NO 12
<211> LENGTH: 6
<212> TYPE: PRT
<213> ORGANISM: Artificial Sequence
<220> FEATURE:
<223> OTHER INFORMATION: Synthetic

<400> SEQUENCE: 12

Met Asn Arg Leu Gly Lys
1               5

<210> SEQ ID NO 13
<211> LENGTH: 6
<212> TYPE: PRT
<213> ORGANISM: Artificial Sequence
<220> FEATURE:
<223> OTHER INFORMATION: Synthetic

<400> SEQUENCE: 13

Lys Val Phe Gly Arg Cys
1               5

<210> SEQ ID NO 14
<211> LENGTH: 12
<212> TYPE: PRT
<213> ORGANISM: Artificial Sequence
<220> FEATURE:
<223> OTHER INFORMATION: Synthetic

<400> SEQUENCE: 14

Asp Asn Tyr Arg Gly Tyr Ser Leu Gly Asn Trp Val
1               5                   10

<210> SEQ ID NO 15
<211> LENGTH: 12
<212> TYPE: PRT
<213> ORGANISM: Artificial Sequence
<220> FEATURE:
<223> OTHER INFORMATION: Synthetic

```
<400> SEQUENCE: 15

Asp Tyr Gly Ile Leu Gln Ile Asn Ser Arg Trp Trp
1               5                   10

<210> SEQ ID NO 16
<211> LENGTH: 10
<212> TYPE: PRT
<213> ORGANISM: Artificial Sequence
<220> FEATURE:
<223> OTHER INFORMATION: Synthetic

<400> SEQUENCE: 16

Asp Gly Arg Thr Pro Gly Ser Arg Asn Leu
1               5                   10

<210> SEQ ID NO 17
<211> LENGTH: 11
<212> TYPE: PRT
<213> ORGANISM: Artificial Sequence
<220> FEATURE:
<223> OTHER INFORMATION: Synthetic

<400> SEQUENCE: 17

Asp Val Gln Ala Trp Ile Arg Gly Cys Arg Leu
1               5                   10

<210> SEQ ID NO 18
<211> LENGTH: 8
<212> TYPE: PRT
<213> ORGANISM: Artificial Sequence
<220> FEATURE:
<223> OTHER INFORMATION: Synthetic

<400> SEQUENCE: 18

Asp Val Gln Ala Trp Ile Arg Gly
1               5

<210> SEQ ID NO 19
<211> LENGTH: 8
<212> TYPE: PRT
<213> ORGANISM: Artificial Sequence
<220> FEATURE:
<223> OTHER INFORMATION: Synthetic

<400> SEQUENCE: 19

Ser Glu Lys Leu Asp Gln Trp Leu
1               5

<210> SEQ ID NO 20
<211> LENGTH: 6
<212> TYPE: PRT
<213> ORGANISM: Artificial Sequence
<220> FEATURE:
<223> OTHER INFORMATION: Synthetic

<400> SEQUENCE: 20

Asp His Pro Phe Leu Phe
1               5

<210> SEQ ID NO 21
<211> LENGTH: 17
<212> TYPE: PRT
<213> ORGANISM: Artificial Sequence
<220> FEATURE:
<223> OTHER INFORMATION: Synthetic
```

```
<400> SEQUENCE: 21

Asp Ala Ala Ser Val Ser Glu Glu Phe Arg Ala Asp His Pro Phe Leu
1               5                   10                  15

Phe

<210> SEQ ID NO 22
<211> LENGTH: 10
<212> TYPE: PRT
<213> ORGANISM: Artificial Sequence
<220> FEATURE:
<223> OTHER INFORMATION: Synthetic

<400> SEQUENCE: 22

Gly Ser Ile Gly Ala Ala Ser Met Glu Phe
1               5                   10

<210> SEQ ID NO 23
<211> LENGTH: 12
<212> TYPE: PRT
<213> ORGANISM: Artificial Sequence
<220> FEATURE:
<223> OTHER INFORMATION: Synthetic

<400> SEQUENCE: 23

Asp Leu Ile Ala Tyr Leu Lys Lys Ala Thr Asn Glu
1               5                   10

<210> SEQ ID NO 24
<211> LENGTH: 129
<212> TYPE: PRT
<213> ORGANISM: Artificial Sequence
<220> FEATURE:
<223> OTHER INFORMATION: Synthetic

<400> SEQUENCE: 24

Lys Val Phe Gly Arg Cys Glu Leu Ala Ala Ala Met Lys Arg His Gly
1               5                   10                  15

Leu Asp Asn Tyr Arg Gly Tyr Ser Leu Gly Asn Trp Val Cys Ala Ala
                20                  25                  30

Lys Phe Glu Ser Asn Phe Asn Thr Gln Ala Thr Asn Arg Asn Thr Asp
            35                  40                  45

Gly Ser Thr Asp Tyr Gly Ile Leu Gln Ile Asn Ser Arg Trp Trp Cys
        50                  55                  60

Asn Asp Gly Arg Thr Pro Gly Ser Arg Asn Leu Cys Asn Ile Pro Cys
65                  70                  75                  80

Ser Ala Leu Leu Ser Ser Asp Ile Thr Ala Ser Val Asn Cys Ala Lys
                85                  90                  95

Lys Ile Val Ser Asp Ala Asn Gly Met Asn Ala Trp Val Ala Trp Arg
            100                 105                 110

Asn Arg Cys Lys Gly Thr Asp Val Gln Ala Trp Ile Arg Gly Cys Arg
        115                 120                 125

Leu

<210> SEQ ID NO 25
<211> LENGTH: 10
<212> TYPE: PRT
<213> ORGANISM: Artificial Sequence
<220> FEATURE:
<223> OTHER INFORMATION: Synthetic

<400> SEQUENCE: 25
```

```
Lys Asn Phe Phe Trp Lys Thr Phe Thr Ser
1               5                   10
```

<210> SEQ ID NO 26
<211> LENGTH: 20
<212> TYPE: PRT
<213> ORGANISM: Artificial Sequence
<220> FEATURE:
<223> OTHER INFORMATION: Synthetic

<400> SEQUENCE: 26

```
Gly Ile Val Glu Gln Cys Cys Ala Ser Val Cys Ser Leu Tyr Gln Leu
1               5                   10                  15

Glu Asn Tyr Cys
            20
```

<210> SEQ ID NO 27
<211> LENGTH: 20
<212> TYPE: PRT
<213> ORGANISM: Artificial Sequence
<220> FEATURE:
<223> OTHER INFORMATION: Synthetic

<400> SEQUENCE: 27

```
Gly Ile Val Glu Gln Cys Cys Ala Ser Val Cys Ser Leu Tyr Gln Leu
1               5                   10                  15

Glu Asn Tyr Cys
            20
```

<210> SEQ ID NO 28
<211> LENGTH: 6
<212> TYPE: PRT
<213> ORGANISM: Artificial Sequence
<220> FEATURE:
<223> OTHER INFORMATION: Synthetic

<400> SEQUENCE: 28

```
Phe Val Asn Gln Gly Leu
1               5
```

<210> SEQ ID NO 29
<211> LENGTH: 5
<212> TYPE: PRT
<213> ORGANISM: Artificial Sequence
<220> FEATURE:
<223> OTHER INFORMATION: Synthetic

<400> SEQUENCE: 29

```
Gly Ile Val Glu Gln
1               5
```

<210> SEQ ID NO 30
<211> LENGTH: 123
<212> TYPE: PRT
<213> ORGANISM: Artificial Sequence
<220> FEATURE:
<223> OTHER INFORMATION: Synthetic

<400> SEQUENCE: 30

```
Glu Gln Leu Thr Lys Cys Glu Val Phe Gln Glu Leu Lys Asp Leu Lys
1               5                   10                  15

Gly Tyr Gly Gly Val Ser Leu Pro Glu Trp Val Cys Thr Thr Phe His
            20                  25                  30

Thr Ser Gly Tyr Asp Thr Glu Ala Ile Val Gln Asn Asn Asp Ser Thr
        35                  40                  45
```

```
Glu Tyr Gly Leu Phe Gln Ile Asn Asn Lys Ile Trp Cys Lys Asn Asp
         50                  55                  60

Gln Asp Pro His Ser Ser Asn Ile Cys Asn Ile Ser Cys Asp Lys Phe
 65                  70                  75                  80

Leu Asp Asp Leu Thr Asp Ile Met Cys Val Lys Lys Ile Leu
                 85                  90                  95

Asp Lys Val Gly Ile Asn Tyr Trp Leu Ala His Lys Ala Leu Cys Ser
             100                 105                 110

Glu Lys Leu Asp Gln Trp Leu Cys Glu Lys Leu
        115                 120
```

<210> SEQ ID NO 31
<211> LENGTH: 6
<212> TYPE: PRT
<213> ORGANISM: Artificial Sequence
<220> FEATURE:
<223> OTHER INFORMATION: Synthetic

<400> SEQUENCE: 31

```
Glu Gln Leu Thr Lys Cys
 1               5
```

<210> SEQ ID NO 32
<211> LENGTH: 7
<212> TYPE: PRT
<213> ORGANISM: Artificial Sequence
<220> FEATURE:
<223> OTHER INFORMATION: Synthetic

<400> SEQUENCE: 32

```
Gln Trp Leu Cys Glu Lys Leu
 1               5
```

<210> SEQ ID NO 33
<211> LENGTH: 8
<212> TYPE: PRT
<213> ORGANISM: Artificial Sequence
<220> FEATURE:
<223> OTHER INFORMATION: Sythetic

<400> SEQUENCE: 33

```
Ser Glu Lys Leu Asp Gln Trp Leu
 1               5
```

<210> SEQ ID NO 34
<211> LENGTH: 13
<212> TYPE: PRT
<213> ORGANISM: Artificial Sequence
<220> FEATURE:
<223> OTHER INFORMATION: Synthetic

<400> SEQUENCE: 34

```
Lys Val Gly Ile Asn Tyr Trp Leu Ala His Lys Ala Leu
 1               5                  10
```

<210> SEQ ID NO 35
<211> LENGTH: 14
<212> TYPE: PRT
<213> ORGANISM: Artificial Sequence
<220> FEATURE:
<223> OTHER INFORMATION: Synthetic

<400> SEQUENCE: 35

```
Ser Thr Glu Tyr Gly Leu Phe Gln Ile Asn Asn Lys Ile Trp
```

```
<210> SEQ ID NO 36
<211> LENGTH: 14
<212> TYPE: PRT
<213> ORGANISM: Artificial Sequence
<220> FEATURE:
<223> OTHER INFORMATION: Synthetic

<400> SEQUENCE: 36

Leu Lys Gly Tyr Gly Gly Val Ser Leu Pro Glu Trp Val Trp
1               5                   10

<210> SEQ ID NO 37
<211> LENGTH: 8
<212> TYPE: PRT
<213> ORGANISM: Artificial Sequence
<220> FEATURE:
<223> OTHER INFORMATION: Synthetic

<400> SEQUENCE: 37

Gln Asp Pro His Ser Ser Asn Ile
1               5

<210> SEQ ID NO 38
<211> LENGTH: 385
<212> TYPE: PRT
<213> ORGANISM: Artificial Sequence
<220> FEATURE:
<223> OTHER INFORMATION: Synthetic

<400> SEQUENCE: 38

Gly Ser Ile Gly Ala Ala Ser Met Glu Phe Cys Phe Asp Val Phe Lys
1               5                   10                  15

Glu Leu Lys Val His His Ala Asn Glu Asn Ile Phe Tyr Cys Pro Ile
                20                  25                  30

Ala Ile Met Ser Ala Leu Ala Met Val Tyr Leu Gly Ala Lys Asp Ser
            35                  40                  45

Thr Arg Thr Gln Ile Asn Lys Val Val Arg Phe Asp Lys Leu Pro Gly
        50                  55                  60

Phe Gly Asp Ser Ile Glu Ala Gln Cys Gly Thr Ser Val Asn Val His
65                  70                  75                  80

Ser Ser Leu Arg Asp Ile Leu Asn Gln Ile Thr Lys Pro Asn Asp Val
                85                  90                  95

Tyr Ser Phe Ser Leu Ala Ser Arg Leu Tyr Ala Glu Glu Arg Tyr Pro
            100                 105                 110

Ile Leu Pro Glu Tyr Leu Gln Cys Val Lys Glu Leu Tyr Arg Gly Gly
        115                 120                 125

Leu Glu Pro Ile Asn Phe Gln Thr Ala Ala Asp Gln Ala Arg Glu Leu
    130                 135                 140

Ile Asn Ser Trp Val Glu Ser Gln Thr Asn Gly Ile Ile Arg Asn Val
145                 150                 155                 160

Leu Gln Pro Ser Ser Val Asp Ser Gln Thr Ala Met Val Leu Val Asn
                165                 170                 175

Ala Ile Val Phe Lys Gly Leu Trp Glu Lys Ala Phe Lys Asp Glu Asp
            180                 185                 190

Thr Gln Ala Met Pro Phe Arg Val Thr Glu Gln Glu Ser Lys Pro Val
        195                 200                 205

Gln Met Met Tyr Gln Ile Gly Leu Phe Arg Val Ala Ser Met Ala Ser
    210                 215                 220
```

-continued

```
Glu Lys Met Lys Ile Leu Glu Leu Pro Phe Ala Ser Gly Thr Met Ser
225             230              235             240

Met Leu Val Leu Leu Pro Asp Glu Val Ser Gly Leu Glu Gln Leu Glu
                245             250             255

Ser Ile Ile Asn Phe Glu Lys Leu Thr Glu Trp Thr Ser Ser Asn Val
            260             265             270

Met Glu Glu Arg Lys Ile Lys Val Tyr Leu Pro Arg Met Lys Met Glu
        275             280             285

Glu Lys Tyr Asn Leu Thr Ser Val Leu Met Ala Met Gly Ile Thr Asp
    290             295             300

Val Phe Ser Ser Ser Ala Asn Leu Ser Gly Ile Ser Ser Ala Glu Ser
305             310             315             320

Leu Lys Ile Ser Gln Ala Val His Ala Ala His Ala Glu Ile Asn Glu
                325             330             335

Ala Gly Arg Glu Val Val Gly Ser Ala Glu Ala Gly Val Asp Ala Ala
            340             345             350

Ser Val Ser Glu Glu Phe Arg Ala Asp His Pro Phe Leu Phe Cys Ile
        355             360             365

Lys His Ile Ala Thr Asn Ala Val Leu Phe Phe Gly Arg Cys Val Ser
    370             375             380

Pro
385
```

METHOD AND APPARATUS FOR PYROLYSIS-INDUCED CLEAVAGE IN PEPTIDES AND PROTEINS

The United States Government has rights in this invention under National Institutes of Health—National Center for Research Resource (R15-RR020354-01A1) and United States Department of Agriculture (USDA Grant #448800).

REFERENCE TO THE SEQUENCE LISTING

Applicant hereby incorporates by reference material submitted via Web-EFS in the following file:

| File Name | Date Created | Size |
| --- | --- | --- |
| 06-106 Div Seq listingReplacement_ST25.txt | Sep. 3, 2015 | 11.8 kb |

BACKGROUND OF THE INVENTION

This application is a divisional application of U.S. patent application Ser. No. 12/371,893, filed Feb. 16, 2009, which is a continuation-in-part of U.S. patent application Ser. No. 12/307,538, filed Jan. 5, 2009, which is the National Phase Entry of PCT Application No. PCT/US2007/015444, filed Jul. 5, 2007, which claims priority to U.S. Provisional Application Ser. No. 60/818,858 filed on Jul. 6, 2006

The invention relates generally to pyrolysis-induced cleavage of peptides and proteins and, more specifically, to a simple and site-specific nonenzymatic method based on pyrolysis has been developed to cleave peptides and proteins.

Pyrolytic cleavage is found to be specific and rapid as it induced a cleavage at the C-terminal side of aspartic acid, at the N-terminal side of csyeine and at disulfide bonds in the temperature range of 220-250° C. in 10 s. Electrospray ionization (ESI) mass spectrometry (MS) and tandem-MS (MS/MS) were used to characterize and identify pyrolysis cleavage products, confirming that sequence information is conserved after the pyrolysis process in both peptides and protein tested. This suggests that pyrolysis-induced cleavage at aspartyl residues can be used as a rapid protein digestion procedure for the generation of sequence-specific protein biomarkers.

Protein digestion along with either peptide mass mapping or sequence-specific mass spectra forms part of a powerful bottom-up method for protein identification and characterization. This approach has been made possible by advances in both mass analyzer designs and the advent of new ionization techniques like matrix-assisted laser desorption/ionization (MALDI) and electrospray ionization (ESI). Digestion of proteins into peptides is usually carried out by enzymatic action, commonly tryptic, along with chemical methods like CNBr cleavage at methionine and oxidative chemical cleavage at tyrosine and trytophan. Even though these methods provide the required site-specificity for successful database search and protein identification, they depend on relatively slow enzymatic activity or require time-consuming or labor intensive procedures. Moreover, tryptic-based approaches may not be particularly suited for proteins lacking arginine and/or lysine amino acids or non-soluble proteins. In addition, for applications requiring automated and field-portable instrumentation and using proteomic-based analyses, approaches using enzymatic digestion may add to the complexity and cost of the final field-portable device. It is with this focus on automation and miniaturization of the sample preparation step for bottom-up proteomic analyses for microorganism detection (i.e., biodetection) that our laboratory is developing rapid reagentless approaches for site-specific cleavage of peptides and proteins based on pyrolysis, electrochemical oxidation, and microwave-heated mild acid hydrolysis.

Pyrolysis has been widely used as a sample preparation step in the analysis of low molecular weight volatile products by mass spectrometry. More recently, however, the focus has been shifted to the analysis of nonvolatile pyrolysis products of biological and synthetic polymers by MALDI-MS.

Besides offering the ability to analyze the intact synthetic polymer molecules, ESI and MALDI allow the analysis of the non-volatile pyrolysis products of these compounds. MALDI-MS is particularly well suited for the analysis of high molecular weight mixtures and complex synthetic polymer compounds due to the predominant singly charged nature of the signals generated. The use of MALDI-MS to study non-volatile pyrolysis products was first demonstrated with the analysis of pyrolytic products of segmented polyurethane. This study identified several series of oligomeric non-volatile products over the mass range ~800-10,000 Da, including linear and cyclic polyester oligomers. MALDI-MS was also employed to study low-temperature pyrolysis products from poly(ethylene glycol). This last study found that the dominant oligomeric products had hydroxyl and ethyl ether end groups, while at higher temperatures, methyl ether and vinyl ether end groups became more abundant in the pyrolyzates. Other studies have also used MALDI-MS for the study of thermal oxidative degradation of nylon-6 and the thermal degradation of aromatic poly(carbonate) polymers in the temperature range of 300-700° C. Pyrolysis was also combined with MALDIMS to study the non-volatile pyrolysis products of poly-amino acids and a small protein pyrolyzed in a nitrogen atmosphere and at temperatures ranging from 245 to 285° C. In this last study, the pyrolysis products were extracted and analyzed by MALDI-MS and it was hypothesized that the amino acid chains undergo dehydration through the formation of cyclic oligopeptides. In addition, the use of ESI-MS for the analysis of nonvolatile pyrolysis products was demonstrated with the pyrolysis of dimethylamphetamine and the analysis of thermal decomposition of three common pharmaceuticals: acetaminophen, indomethacin, and mefenamic acid. In all these studies, however, sample preparation was required and involved dissolving and extracting the non-volatile residues with appropriate solvents (ESI) or mixing with matrices (MALDI). This sample pre-processing step increases analysis time and could possibly affect the analysis by introducing a sampling bias and consequently not detecting important products. The introduction of ambient MS techniques has brought a new dimension in mass spectrometric measurements as they allow the analysis of samples in their native environment. To date, a number of ambient ionization methods for MS analysis have been introduced, but most notably are direct analysis in real-time (DART) and desorption electrospray ionization (DESI). Of interest to this investigation is the ability of DESI to ionize compounds from surfaces with a mechanism similar to conventional ESI and its applicability to analytes of a wide range of molecular weights. These analytes include, but are not limited to, pharmaceuticals and controlled substances, peptides and proteins explosives, clinical samples, intact tissues, synthetic polymers and bacteria. DESI is a rapid desorption/ionization source for MS and requires little to no sample preparation. DESI is carried out by directing aerosolized and electrosprayed charged droplets and ions of solvent onto the surface to be analyzed. The charged droplets impact on the surface and "pick up" available soluble molecules. These charged droplets subsequently "bounce" at a lower angle towards the MS inlet and yield gaseous ions of the compound in an analogous mechanism to that in ESI. Hence, DESI yields mass spectra similar to those obtained by ESI which are characterized by multiply charged ions and are amenable for tandem mass analysis (MS/MS). However, it is reasonable to assume that the nature and polarity of the DESI solvent can be varied to affect sampling of pyrolysis products during the surface pick up step of the DESI process.

SUMMARY OF THE INVENTION

The present invention consists of heating a protein sample defined as a pure protein, a mixture of proteins, whole microorganisms or intact tissue, to pyrolytic temperatures in a short period of time. Preferably, the sample is heated to between about 180° C. and about 250° C., and most preferably to between about 210° C. and 230° C., in a period of between about 5 seconds and about 30 seconds, and most preferably in about 10 seconds. This can be carried out under atmospheric conditions. The pyrolosis can be carried out by any method that provides sufficient heat transfer to the sample, including but not limited to laser radiation, microwave radiation, membrane heaters, ovens, and stoves.

The present invention in preferred embodiments consists of the use of pyrolysis as a sample preparation technique by applying pyrolysis as a site-specific peptide and protein cleavage method. This methodology is found to specifically induce hydrolysis at the C-terminus of the aspartic acid residue, at disulfides bonds, and at the N-terminaus of cysteine in a polypeptide chain in less than 10 seconds. Peptides containing aspartic acid were tested along with the protein lysozyme. Tandem MS (MS/MS) results confirm cleavage at the C-terminus of aspartic acid.

An alternative embodiment of the present invention consists of an on-probe pyrolyzer interfaced to a desorption electrospray ionization (DESI) source as an in situ and rapid pyrolysis technique to investigate non-volatile pyrolytic residues by MS and MS/MS analyses. The technique is useful in sample analysis, including the analysis of biological samples and synthetic polymers.

The purpose of this invention is the rapid and non-enzymatic of peptides and proteins at specific amino acid positions with rapid heating. The invention can be used in proteomic applications to where the purpose is to identify the original protein. The invention being described here achieves the level of site-specificity, is very rapid and uses no enzymes.

The invention has advantages over the enzymatic approach in that it is rapid and inexpensive. The invention performs the digestion in 10 seconds as compared to the several hours to overnight incubation required for the enzyme approach. Moreover, the approach can be easily automated via an electronic circuit. This approach is also very inexpensive as it requires simple hardware and consumes no reagents.

The invention has direct applications to proteomics research, spanning from the health care industry, medical research, homeland security (bioweapons detection). It can be applied to techniques to identify proteins, mixtures of proteins, or the source of proteins as in the identification of microorganisms.

The advantages of this methodology are its fast speed, simplicity and low cost of the device, amino acid site-specificity, low chemical noise, and easy interfacing to MS instrumentation.

BRIEF DESCRIPTION OF THE DRAWINGS

FIGS. 20A-C show the Mascot search results of lysozyme.

FIG. 22 shows the Mascot search result of insulin using the MS/MS data of ions at m/z 778 and 566.

FIG. 26 shows the data file of ion m/z 1263 showing the identification of cytochrome C.

FIGS. 29 (A)-(B) show the full ESI mass spectrum scan of pyrolyzed samples of E. coli and S. Aureus via direct infusion ESI-MS.

FIGS. 30 (A)-(B) show the on-probe DESI-MS full scan of pyrolyzed bacteria whole cells Salmonella typhimutium (A), and Pseudomonas aureginosa (B).

Figure 35:
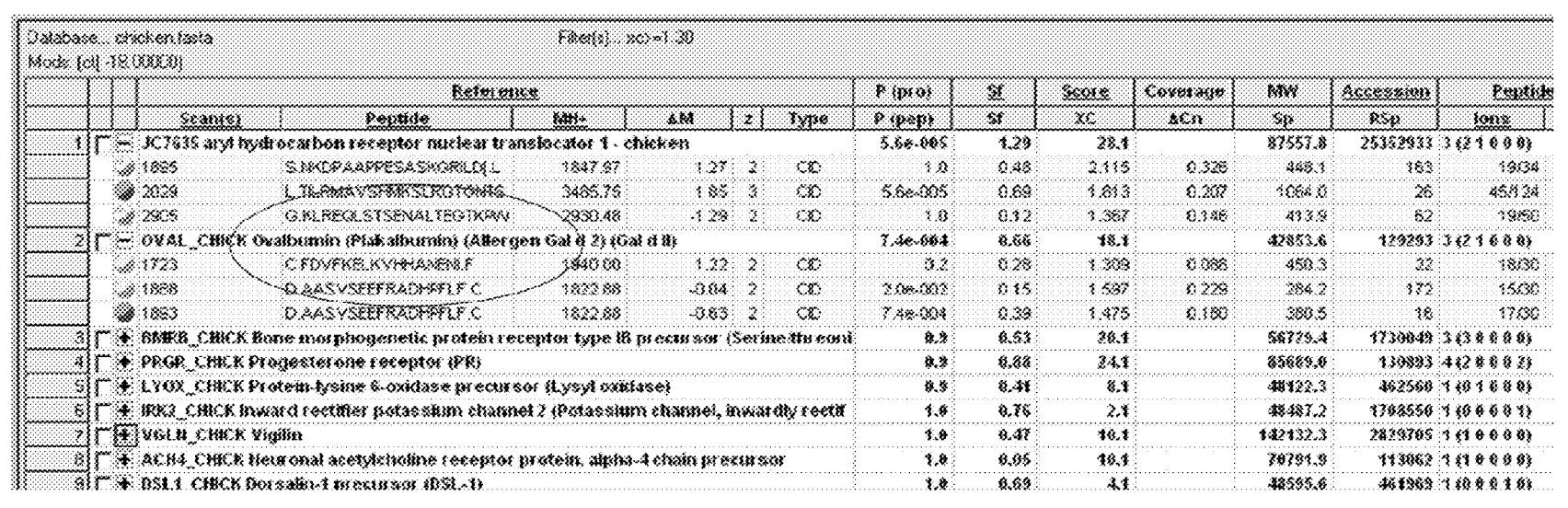

FIG. 35 is a chart of Sequest results gained via HPLC-MS.

FIGS. 37(A) and 37(B) are charts of the full ESI scan of pyrolyzed whole cells of E. coli and S. aureus, respectively.

DETAILED DESCRIPTION OF PREFERRED EMBODIMENTS

Example 1

Figure 1A:
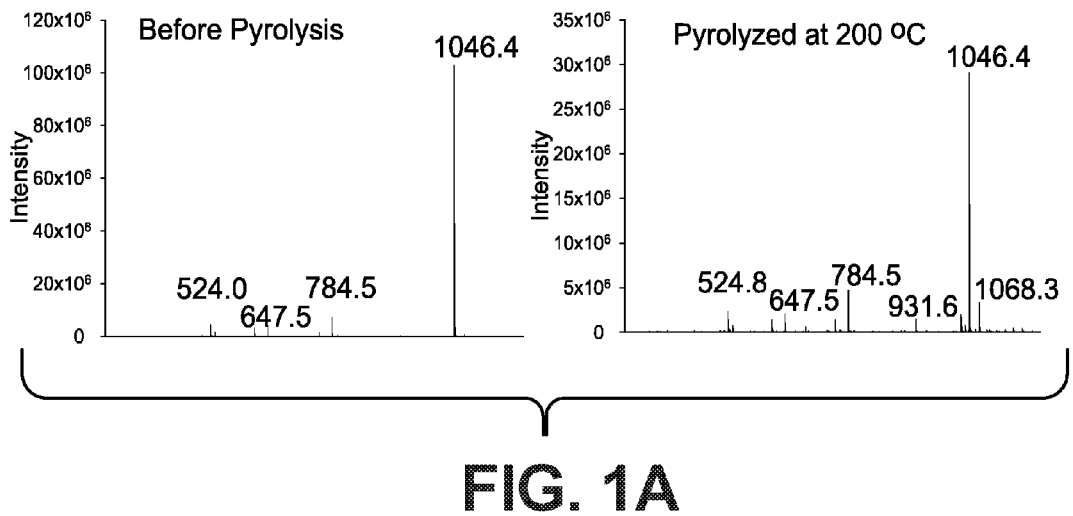
FIGS. 1A-C show the full scan mass spectra of peptide A before pyrolysis (A) and after pyrolysis at different temperatures (B-C).

Pyrolysis-Induced Cleavage at Aspartic Acid Residue in Peptides and Proteins

Chemicals.

Peptides used were: (A) Angiotensin II, human, DRVYIHPF (SEQ ID NO. 1); (B) VIP (1-12) peptide, HSDAVFTDNYTR (SEQ ID NO. 2); and (C) VSV-G peptide, YTDIEMNRLGK (SEQ ID NO. 3) (all from AnaSpec, San Jose, Calif.). Lysozyme protein (from Sigma-Aldrich, St. Louis, Mo.) was used without further purification. All solvents used for sample preparation and MS measurements were HPLC grade (Burdick & Jackson, Muskegon, Mich.), and the formic acid (96%) was ACS Reagent grade (Aldrich, St. Louis, Mo.).

Pyrolyzer Design and Pyrolysis Procedure.

Approximately a 1 mg solid sample of peptide or protein was pyrolyzed under ambient conditions. Samples were placed in a glass tube (length 31 mm and internal diameter 4 mm; Agilent, Santa Clara, Calif., Part #5180-0841) and heated using a resistance heating wire (Omega, Stamford, Conn., nickel-chromium wire, part #NI60-015-50, length 20 cm) enwound around the tube, powered by 13 V alternating current (AC). Temperature was measured in situ using a thermocouple probe (model HH12A, Omega Company, Stamford, Conn.) reaching down the bottom of the glass tube. The sample was heated for 10 s under atmospheric condition to a final temperature of 220° C. The nonvolatile pyrolysis residue was collected by washing/extracting the inside of the tube with 1 mL of a 50/50 (v/v) methanol-water solution with 0.1% formic acid (FA).

Mass Spectrometry.

The extracted solution of pyrolysis products was directly analyzed using a quadrupole ion-trap MS (LCQ classic, Finnigan, San Jose, Calif.) equipped with a nano-Electrospray Ionization (nano-ESI) source by infusing it into the mass spectrometer at a flow rate of 3 µL/min via a 250-µL syringe. Tandem MS (MS/MS) was conducted with the following parameters: activation q of 0.250; isolation width was 1 amu, and the percentage relative collision energy was in the range of 25-40% and was adjusted such that the relative abundance of the precursor ion in the product ion spectrum was approximately 30-50% relative intensity.

MALDI-MS experiments were performed using a MALDI Time-of-Flight MS (Voyager DE-PRO, Applied Biosystems, Foster City, Calif.) instrument equipped with a $N_2$ laser and operated in the reflectron mode. The matrix R-cyano-4-hydroxy-cinnamic acid (CHCA) (Aldrich) was used for all measurements and was prepared by dissolving 10 mg of CHCA in a 1 mL solution of 1:1 acetonitrile/water with 0.1% trifluoroacetic acid (TFA) (Pierce Chemical Co., Rockford, Ill.). The extracted solution of pyrolysis products was directly mixed with the matrix at different volume ratios and air-dried onto a MALDI plate.

Results and Discussion

Analysis of Nonvolatile Pyrolysis Products of Peptides.

Figure 1B:
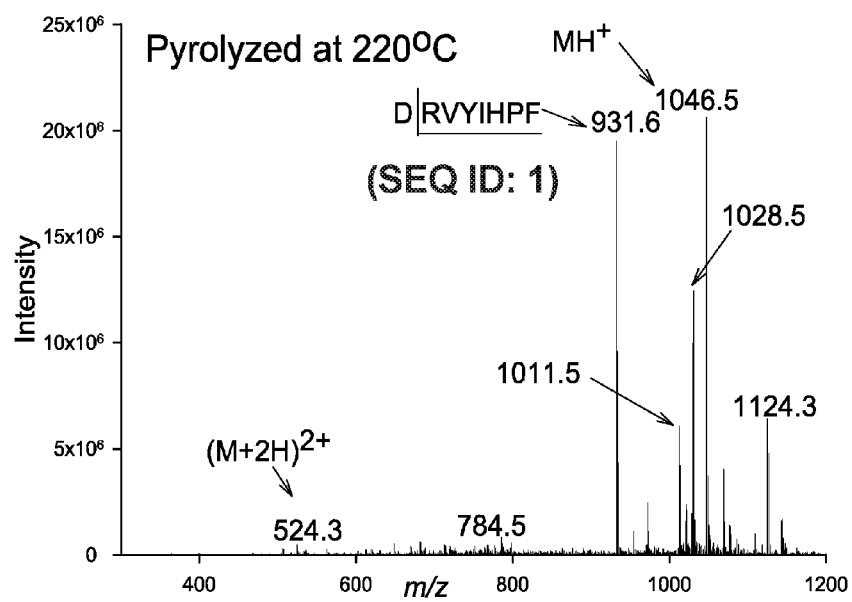
Figure 1C:
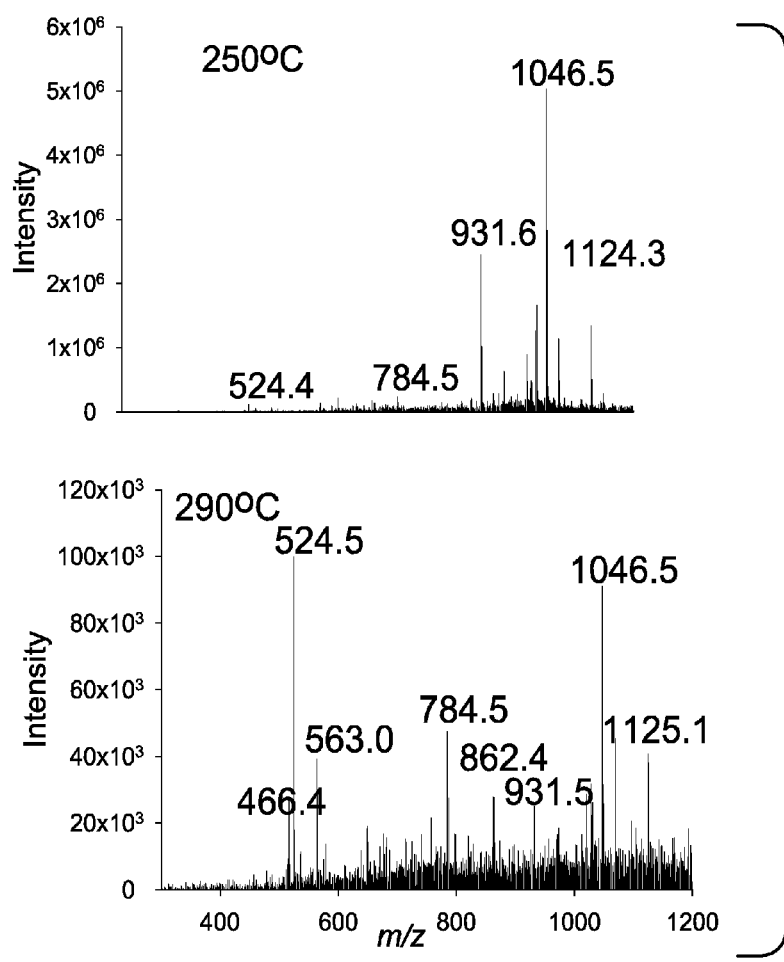

Three peptides containing aspartic acid were pyrolyzed, their nonvolatile products were analyzed by ESI-MS, and their amino acid sequences were confirmed by tandem MS: (A) Angiotensin II, human, DRVYIHPF (SEQ ID NO. 1); (B) VIP (1-12) peptide, HSDAVFTDNYTR (SEQ ID NO. 2); and (C) VSV-G peptide, YTDIEMNRLGK (SEQ ID NO. 3). FIGS. 1A-C show the full scan mass spectra of peptide A before and after pyrolysis at different temperatures.

For the peptides tested at pyrolysis temperatures of 200° C. and lower (data not shown), no significant pyrolysis fragments were detected. On the other extreme, at a pyrolysis temperatures of 290° C. and higher (data not shown), extensive fragmentation products were observed, most likely due to peptide carbonization. At pyrolysis temperatures between 220 and 250° C., the pyrolysis fragment for peptide A due to C-terminus of aspartic acid. Peptide fragmentation at the C-terminus of aspartic acid is believed to proceed via the formation of a five-member cyclic anhydride followed by hydrolysis, because pyrolysis is performed in air and at atmospheric pressure (Scheme 1) (Inglis, S. A. Cleavage at aspartic acid. *Methods Enzymol.* 1983, 91, 324-332).

Scheme 1

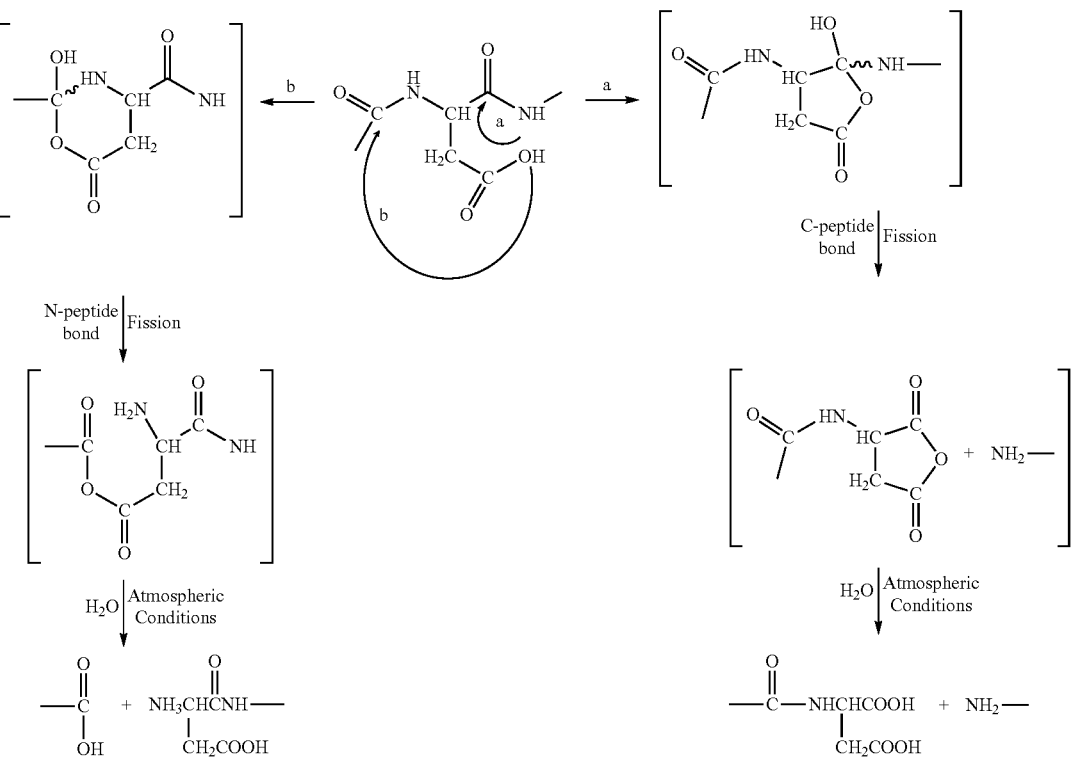

Figure 2:
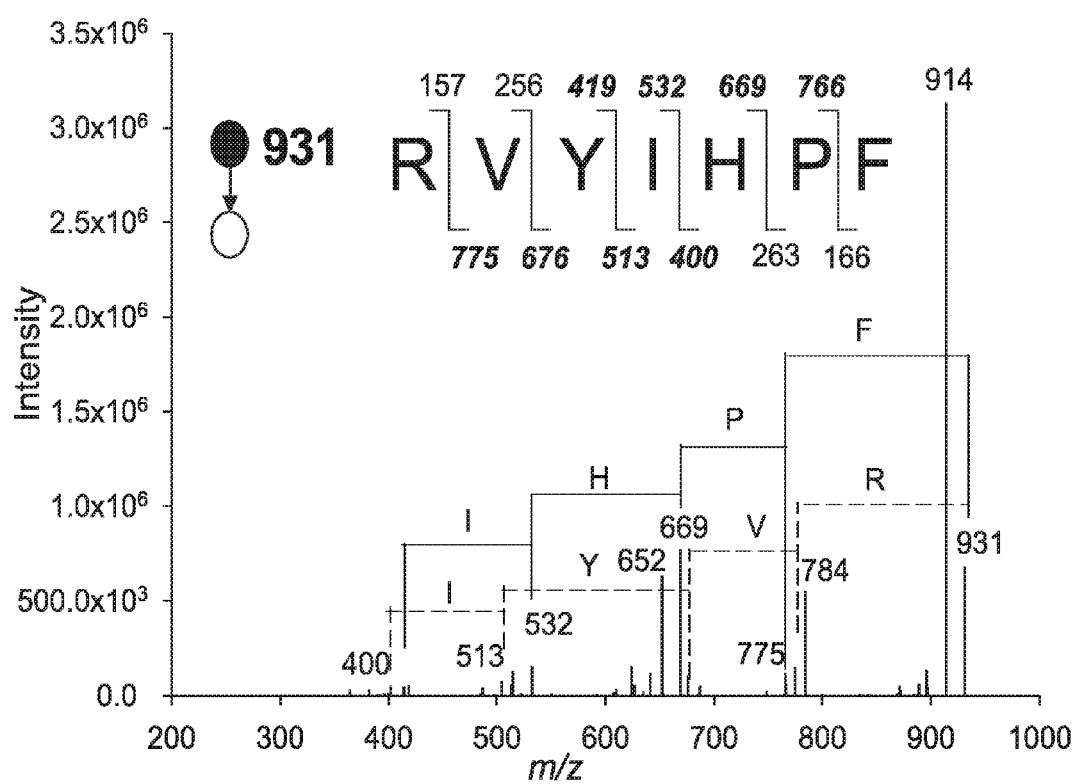
FIG. 2 is the tandem mass spectrum of Angiotensin II pyrolysis product at m/z 931.6.

C-terminal cleavage at aspartic acid was detected at m/z 931.6. Tandem MS (MS/MS) of this ion (FIG. 2) confirmed the sequence RVYIHPF, the product of a C-terminus cleavage at the aspartic acid residue of peptide A. Other peaks present in the spectrum resulted from consecutive loss of water, observed at m/z 1028.5 (C-terminus oxazolone formation) (Zhang, S.; Basile, F. Investigation of Non-Volatile Pyrolysis Products of Proteins Using Electrospray Ionization Multistep Tandem Mass Spectrometry. 54th ASMS Conference, 2006), and loss of ammonia, observed at m/z 1011.5 (from arginine).

Figure 3A:
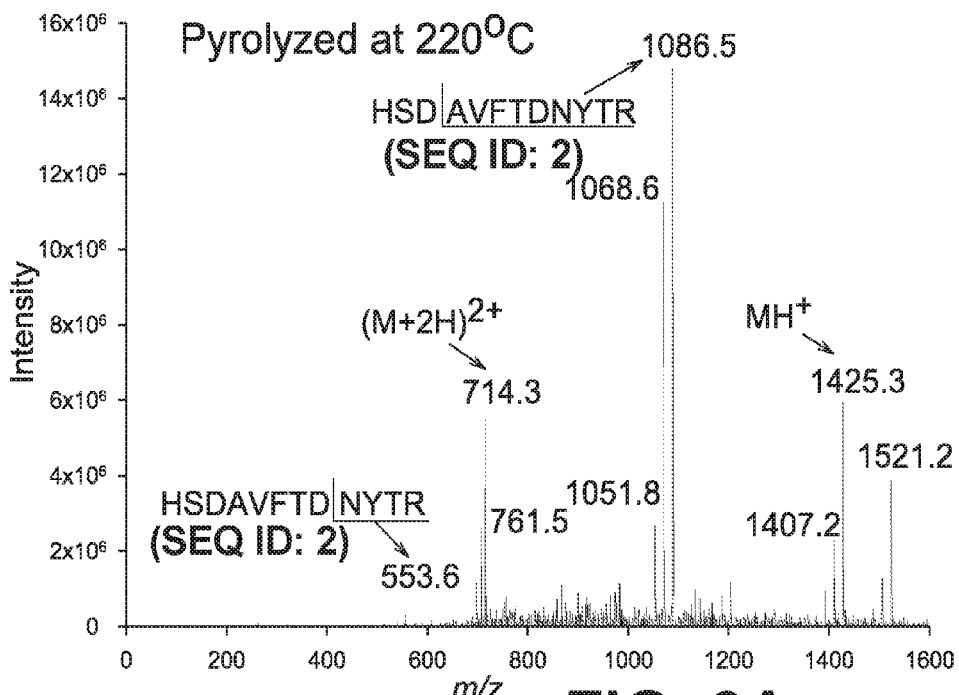
FIGS. 3A and 3B are graphs of the ESI-mass spectrum of pyrolysis products of the VIP (1-12) peptide showing site-specific cleavage at the two aspartic acid sites (3A) and the ESI-mass spectrum of pyrolysis products of the VSV-G peptide (3B).
Figure 3B:
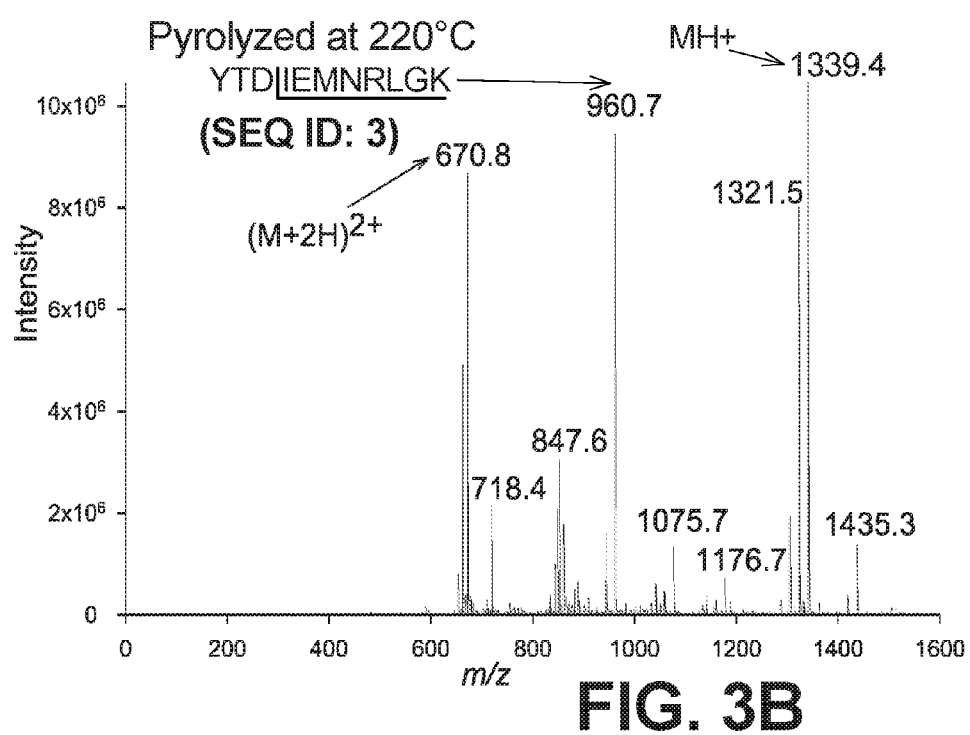
Figure 4A:
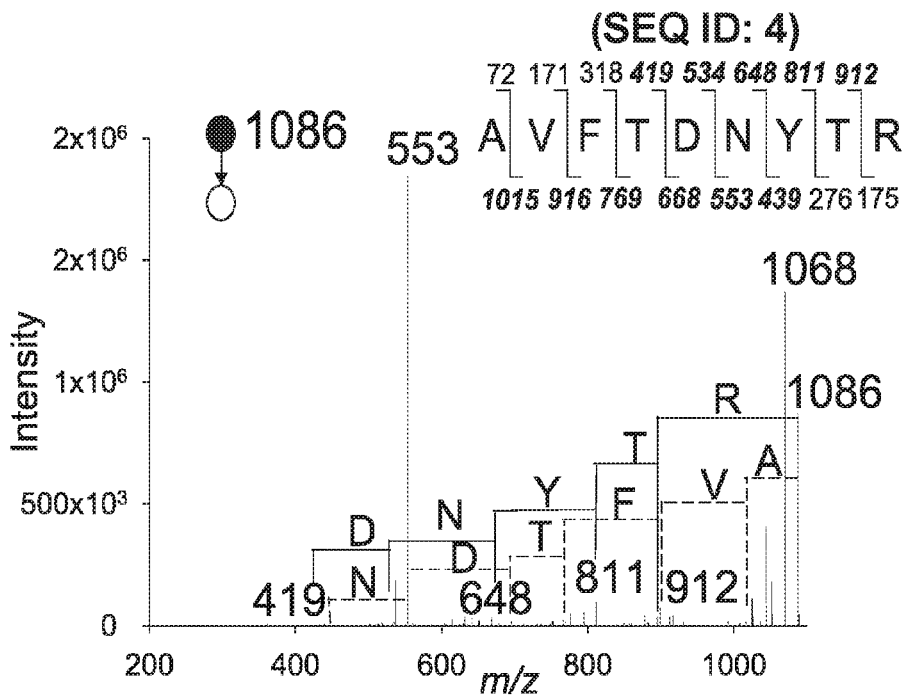
FIGS. 4A and 4B are graphs of the tandem mass spectra of pyrolysis products of the VIP (1-12) peptide, confirming their sequences.
Figure 4B:
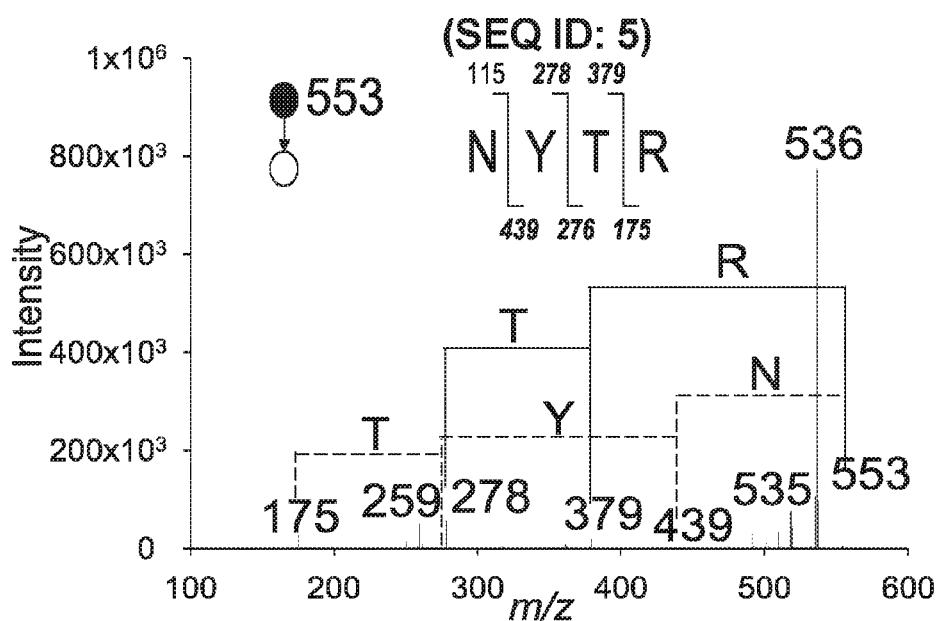

Site-specific pyrolysis-induced cleavage was also observed for peptide B, which contains two aspartic acid residues (ESI-mass spectrum shown in FIG. 3A). After pyrolysis at 220° C., two nonvolatile peptide products were observed at m/z 1086.5 (AVFTDNYTR) (SEQ ID NO. 4) and m/z 553.6 (NYTR) (SEQ ID NO. 5), corresponding to cleavages at each of the two aspartic acid C-terminus sites. Amino acid sequences of these pyrolysis products were confirmed by MS/MS measurements (shown in FIGS. 4A and 4B). Also, possible peptide oxidation products were observed at m/z 1521 for peptide B and at m/z 1435 for peptide C, and their structures are currently being investigated. Similar results were observed for peptide C (FIG. 3B).

These results demonstrate that pyrolysis at temperatures between 220 and 250° C. favors cleavage in peptides at the The overall susceptibility of the aspartic acid group to internal cleavage may stem from the fact that the â-carboxyl group (i.e., side-chain carboxyl group) acts as a proton donor and its hydroxyl oxygen as a nucleophile toward the adjacent carbonyl carbons in the peptide bond. Reaction path "a" in Scheme 1 leads to the formation of a five-member ring, while path "b" forms a six-member ring species. Hydrolysis of these cyclic intermediates results in C- or N-terminus cleavages of the aspartic acid residue, respectively. The six-member ring molecule leading to the N-terminus cleavage is expected to be thermodynamically more stable than the five-member cyclic anhydride molecule (Loudon, G. M. *Organic Chemistry*; Addison-Wesley Publishing Co.: Massachusetts, 1983). However, only C-terminus cleavage products have been detected under pyrolysis conditions, and these would result from the formation of the five-member ring species. Hence, it is hypothesized that the reaction path "a" leading to the pyrolysis-induced C-terminus cleavage is kinetically favored rather than thermodynamically controlled.

Analysis of Nonvolatile Pyrolysis Products of Lysozyme.

Figure 5A:
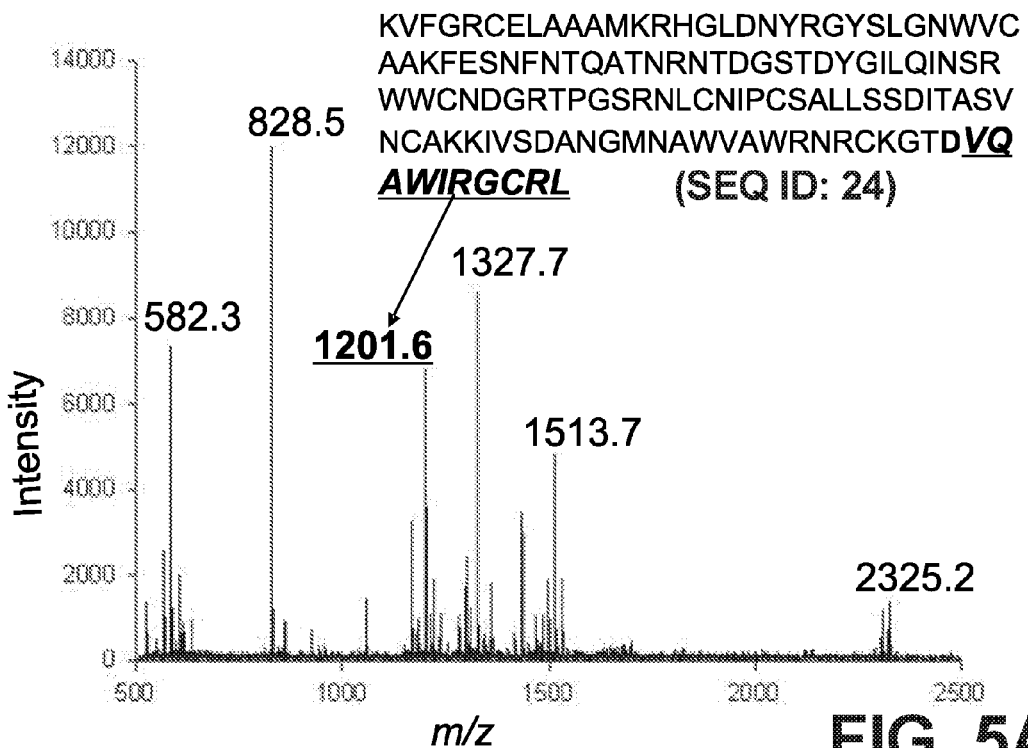
FIGS. 5A and 5B are graphs of the MALDI-mass spectrum of pyrolysis products of the protein lysozyme (14 kDa), indicating the peptide product detected (5A) and the ESI-tandem mass spectrum of the precursor ion at m/z 1201.6 (5B), confirming that sequence information is preserved after protein pyrolysis.

The potential of this methodology to digest intact proteins to smaller peptides for subsequent MS/MS analyses was further tested. MALDI-MS analysis of the nonvolatile pyrolysis products of the protein lysozyme resulted in a series of strong signals in the mass range of 500-2500 u, indicating that complete degradation or carbonization of the protein does not occur at 220° C. (FIG. 5A). Moreover, the ion at m/z 1201.6 observed in the MALDI-mass spectrum matches one of the expected products corresponding to the cleavage at the C-terminus of aspartic acid in lysozyme, the peptide (D)VQAWRGCRL (SEQ ID NO. 6).

Figure 5B:
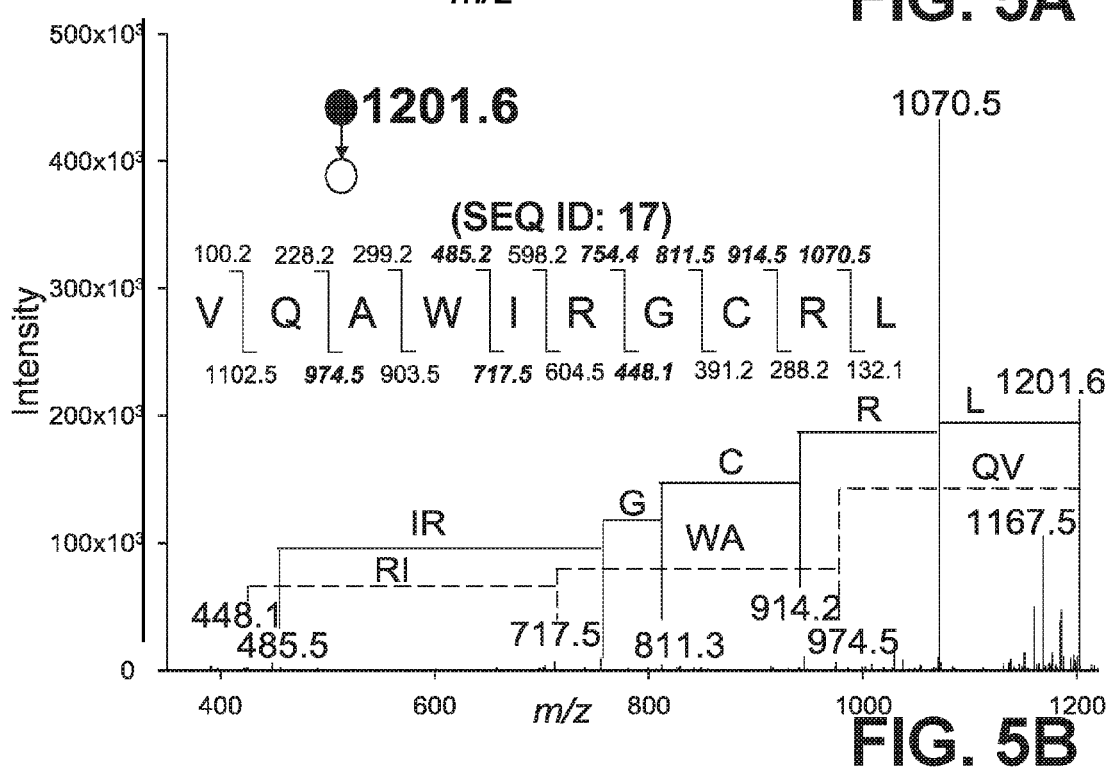

Analysis of this pyrolysis digestion product by ESI-MS/MS (MS/MS of m/z 1201.6) yielded sequence information confirming the peptide amino acid sequence (FIG. 5B). Moreover, fragment ion data were used for successful protein identification via database search (Mascot score 52; threshold score for significant homology was 43; Matrix Science, UK). Hence, the observed pyrolysis digestion product at m/z 1201.6 corresponds to the C-terminal peptide in the lysozyme protein sequence, confirming that the pyrolysis product is derived from the protein and that sequence information is conserved. We are currently investigating factors affecting sequence coverage and the structure of additional pyrolysis products observed (e.g., dehydration, deamination, and oxidation products), the effect of neighboring amino acids on cleavage, and the ability of the method to cleave at other aspartic acid residues, that is, other than those near the C-terminal of the protein sequence.

Conclusion.

The ability of pyrolysis-based digestion methods to produce sequence-specific biomarkers has been demonstrated for peptides and the protein lysozyme. This approach offers the possibility of developing rapid and field-portable proteomic-based methods to detect and identify biological samples, for example, protein toxins and/or pathogenic bacteria (e.g., *Bacillus anthracis*). In this particular application, protein sequence coverage is not a requirement, but, rather, the reproducibility and simplicity of the pyrolysis method is used to generate biological-specific biomarkers.

Example 2

Pyrolysis Device and Procedures

Figure 6A:
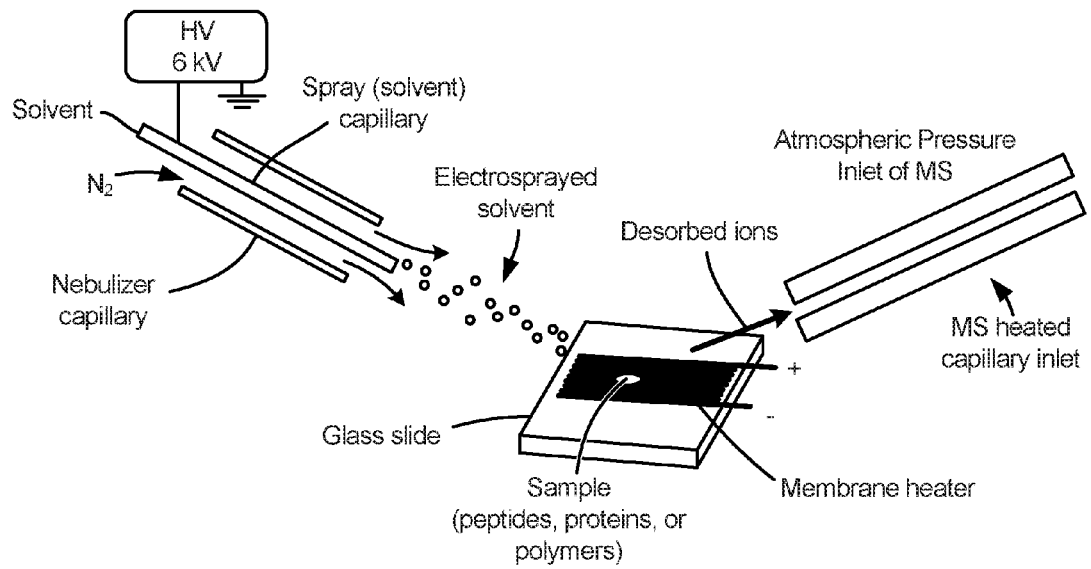
FIG. 6(A) is a diagrammatical view of the on-probe pyrolyzer interfaced to the DESI source.
Figure 6B:
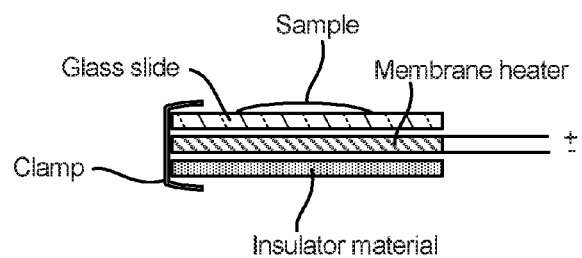
FIG. 6(B) is a diagrammatical view of the on-probe pyrolyzer.

A diagram of the on-probe pyrolyzer interfaced to the DESI source is shown in FIG. 6A. A homebuilt DESI source was interfaced with a quadrupole ion trap MS (LCQ Classic, Thermo Electron, San Jose, Calif.) and was operated in the positive ion mode. The on-probe pyrolyzer consisted of a membrane heater (Model #HM6815, Minco, Minneapolis, Minn.) placed underneath a removable glass slide held tightly together with a clamp (FIG. 6B). The sample to be pyrolyzed was placed directly on the center of the glass slide. The membrane heater was powered by alternating current (AC) from a transformer (Model #3PN116C, Superior Electric, Farmington, Conn.) and heating and final pyrolysis temperature were controlled by adjusting the voltage of the transformer and the heating time. For our current setup, a voltage of 20 V applied for 11 s resulted in a final pyrolysis temperature of 220° C. These values for pyrolysis temperature and time were used for all biological samples analyzed in this study. The glass slide surface temperature was measured in situ using a thermocouple probe (Model #HH12A, Omega Company, Stamford, Conn.) placed in direct contact. After sample pyrolysis, the probe was cooled to room temperature (<5 min) and the DESI-MS analysis carried out. This setup is amenable to conducting pyrolysis in either the off-line or on-line mode with the DESI source, that is, a sample placed on a slide can be pyrolyzed in a furnace under controlled atmospheric conditions and later analyzed by DESI-MS. However, all measurements in this report were performed in the on-line configuration (FIG. 6A).

Several model samples were tested with this new on-probe pyrolyzer DESI-MS instrument. Peptides analyzed included Angiotensin II-human, of sequence DRVYIHPF (SEQ ID NO. 1), and the peptide VIP (1-12), of sequence HSDAVFTDNYTR (SEQ ID NO. 2) (both from AnaSpec, San Jose, Calif.). The proteins used were lysozyme and RNase A, and the synthetic polymer used was poly(ethylene glycol) (PEG 2000) (all from Sigma-Aldrich, St. Louis, Mo.). Methanol, water (from Burdick & Jackson, Muskegon) and tetrahydrofuran (THF, from EMD Chemicals, San Diego, Calif.) were used for sample preparation and MS measurements (all HPLC grade). About a 1 mg sample of the peptides was dissolved in 200 μL of methanol, and the entire solution air-dried on a glass slide (covering a surface area approx. 6 $cm^2$, ~0.1 mg sample/$cm^2$) and placed on the on-probe pyrolyzer. Lysozyme and RNase A were prepared in a similar fashion, but dissolved in water. For poly(ethylene glycol), about 10 mg of PEG 2000 was dissolved in 1 mL of THF, air-dried on a glass slide (~1 mg/$cm^2$), placed on the on-probe pyrolyzer and heated to a final temperature of 250° C. for 30 min.

DESI and Mass Spectrometry Parameters

The DESI source was operated with a high voltage of 6 kV applied to the spraying solvent. The spraying solvent consisting of 50% methanol in water (v/v) was delivered at a flow rate of 7 μL/min via a syringe pump. All mass spectra were collected in spectral average mode. The pressure of the DESI nebulizer gas ($N_2$) was set as 250 psi.

Tandem MS (MS/MS) measurements were conducted with the following parameters: activation q of 0.250; isolation width was 1 amu and the percentage relative collision energy was in the range of 25-40%, and was adjusted to get a precursor ion peak of 25% relative intensity or less (when possible).

Results and Discussion

The utility and versatility of the DESI source interfaced with the on-probe pyrolyzer for the analysis of non-volatile pyrolysis products were demonstrated with several model compounds that included peptides, proteins and a synthetic polymer.

Example 3

On-Probe Pyrolysis DESI-MS Analysis of Biomolecules

As described in Example 1, the site-specific pyrolysis-induced cleavage at the amino acid aspartic acid (letter symbol "D") in both peptides and proteins has been achieved by heating samples to a temperature of 220-250° C. for 10 s under atmospheric pressure conditions. Peptides and proteins in this previous study were pyrolyzed in an open-ended tube furnace, extracted with a suitable solvent and analyzed by ESI-MS and MS/MS to characterize and identify non-volatile pyrolysis cleavage products. In this Example, the same samples were pyrolyzed on-probe and products were analyzed in situ by DESI-MS, bypassing the sample extraction, transfer, and ESIinfusion steps. In the ESI-MS study and the DESI-MS study here described, pyrolysis of peptides and proteins above 300° C. produced complete charring of the polypeptide backbone.

Pyrolysis induced site-specific cleavage at aspartic acid has was observed mostly at low temperature pyrolysis. However, this pyrolysis cleavage reaction is not exclusive in biomolecules as other pyrolysis fragments have been detected and the system here described is presently being used to further characterize the structure and nature of these pyrolysis fragments.

Figure 7A:
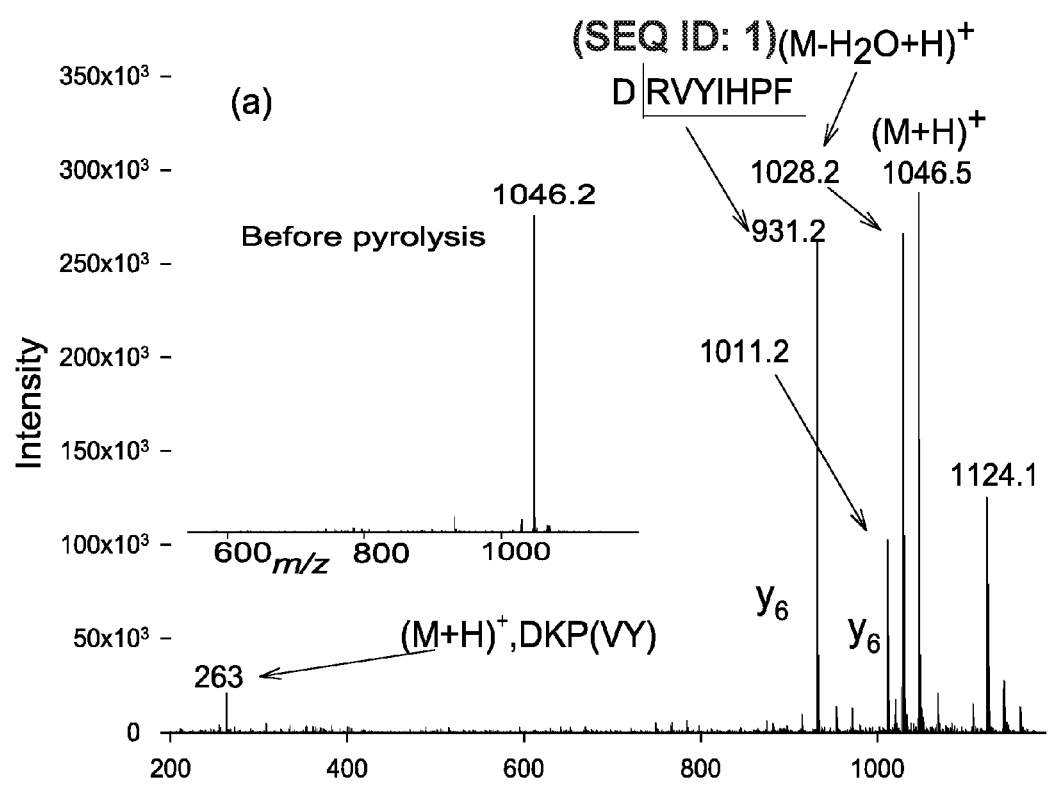
FIG. 7(A) is a diagrammatical view of the on-probe pyrolysis (220° C., 11 s) DESI-mass spectrum of Angiotensin II (inset: before pyrolysis DESI-mass spectrum); site-specific cleavage is induced at the C-terminus of aspartic acid. Ions at m/z 1028 and 1011 are the result of dehydration and deamination reactions.
Figure 7B:
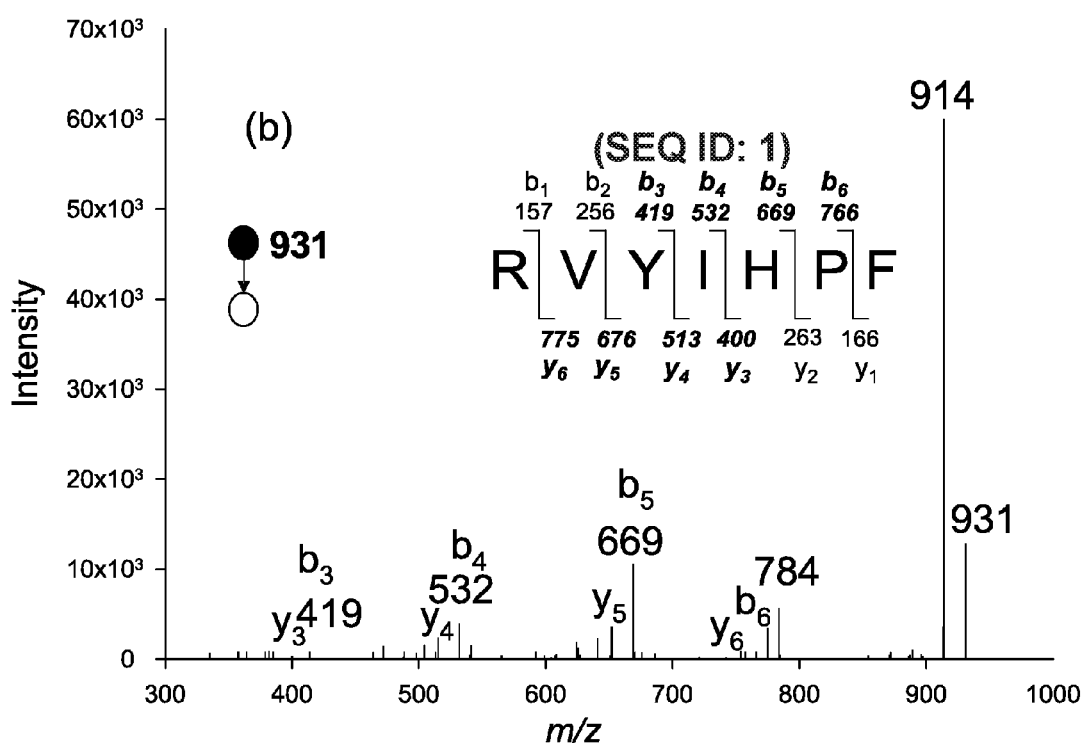
FIG. 7(B) is a diagrammatical view of the on-probe pyrolysis DESI-tandem mass spectrum of the ion at m/z 931.

FIGS. 7A and 7B illustrate the DESI-mass spectra before and after onprobe pyrolysis of the peptide Angiotensin II, along with the tandem mass spectrum of the pyrolytic product at m/z 931. The DESI-mass spectrum of the non-volatile products also shows the formation of a dehydration product at m/z 1028.2, a possible oxidation product at m/z 1124.1 (of yet unknown structure) and the product of the pyrolysis induced site-specific cleavage at aspartic acid at m/z 931.2 (the D-cleavage pyrolysis peptide product). Tandem MS data of the ion at m/z 931 confirms that sequence-specific information is preserved after low temperature pyrolysis of peptides.

Figure 8A:
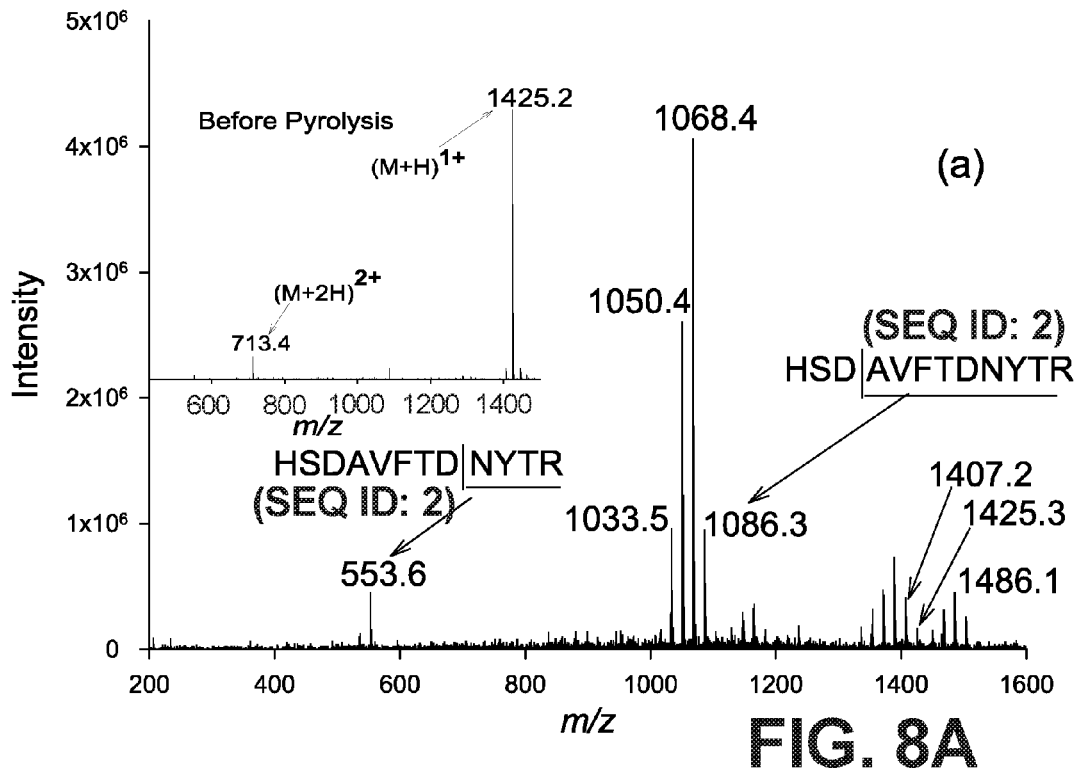
FIGS. 8(A-C) are diagrammatical views of (a) the on-probe pyrolysis DESI-mass spectrum of the VIP peptide showing site-specific cleavages at the two aspartic acids amino acids (inset: before pyrolysis DESI-mass spectrum); and the on-probe pyrolysis DESI-tandem mass spectrum of pyrolytic product at (b) m/z 1086 and (c) m/z 553.

The above measurement demonstrates the simplicity and speed of analysis of pyrolysis residues with the on-probe pyrolyzer coupled to a DESI-MS system. No solvents were required for residue extraction and solubilization, assuring the analysis of the entire pyrolysis product mixture (i.e., the nonvolatile fraction, vide infra). However, it is reassuring to note that all products detected in the on-probe pyrolysis DESI-MS analysis in FIGS. 8A-C were also observed in the open-ended tube furnace pyrolysis and ESI-MS analysis, which required sample extraction and solubilization. It is important to note that lower MW products like diketopiperazines (DKP) known to be generated under Curie-point and atmospheric pyrolytic conditions were only observed in the analysis of the Angiotensin II peptide (signal at m/z 263 corresponding to the (M+H)+DKP of VY). This may be due to several factors: first, volatile DKP products may have been lost during the pyrolysis process since the on-probe pyrolyzer is operated at atmospheric pressure. Second, early work on the formation of DKP from dipeptides (D. Gross, G. Grodsky, J. Am. Chem. Soc. 77 (1955) 1678-1680; H. J. Svec, G. A. Junk, J. Am. Chem. Soc. 86 (1964) 2278-2282) found that only a small percentage (~7%) of the original dipeptide was converted to DKP at 215° C. And finally, ionization suppression of the DKP (M+H)+ signals within the desorbed DESI droplets may take place, especially if analyzing a complex mixture of pyrolytic products with dissimilar droplet surface activities or DKPs in mixtures with peptides containing highly basic groups (i.e., arginine), as it is the case here.

Figure 8B:
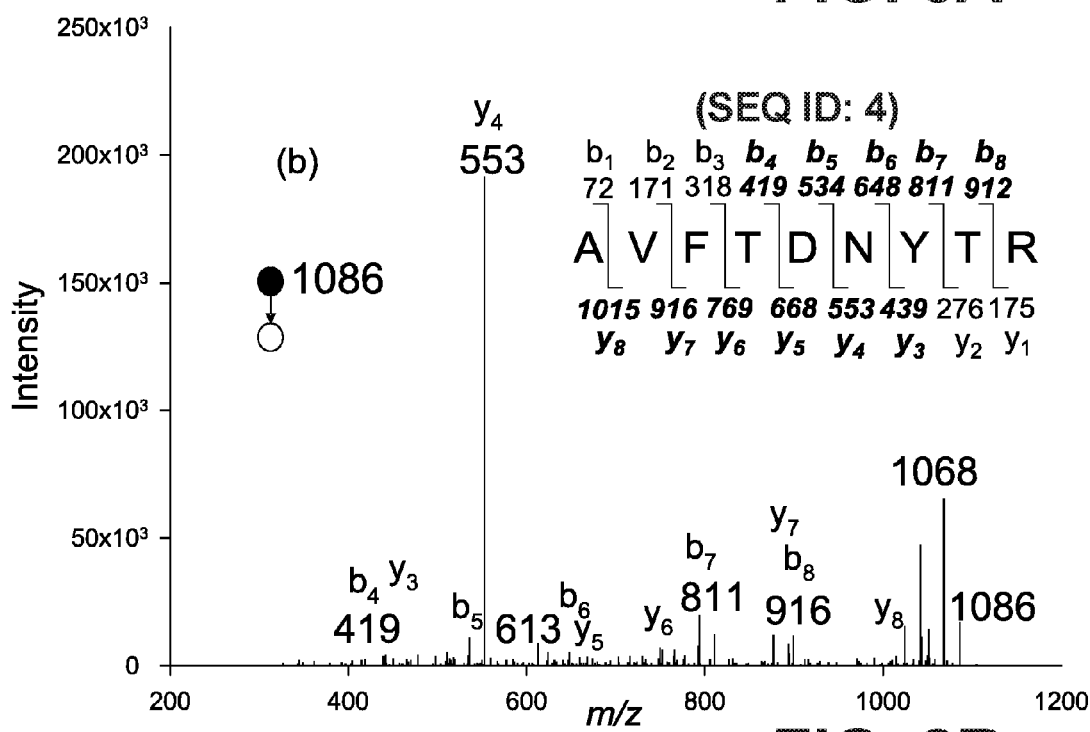
Figure 8C:
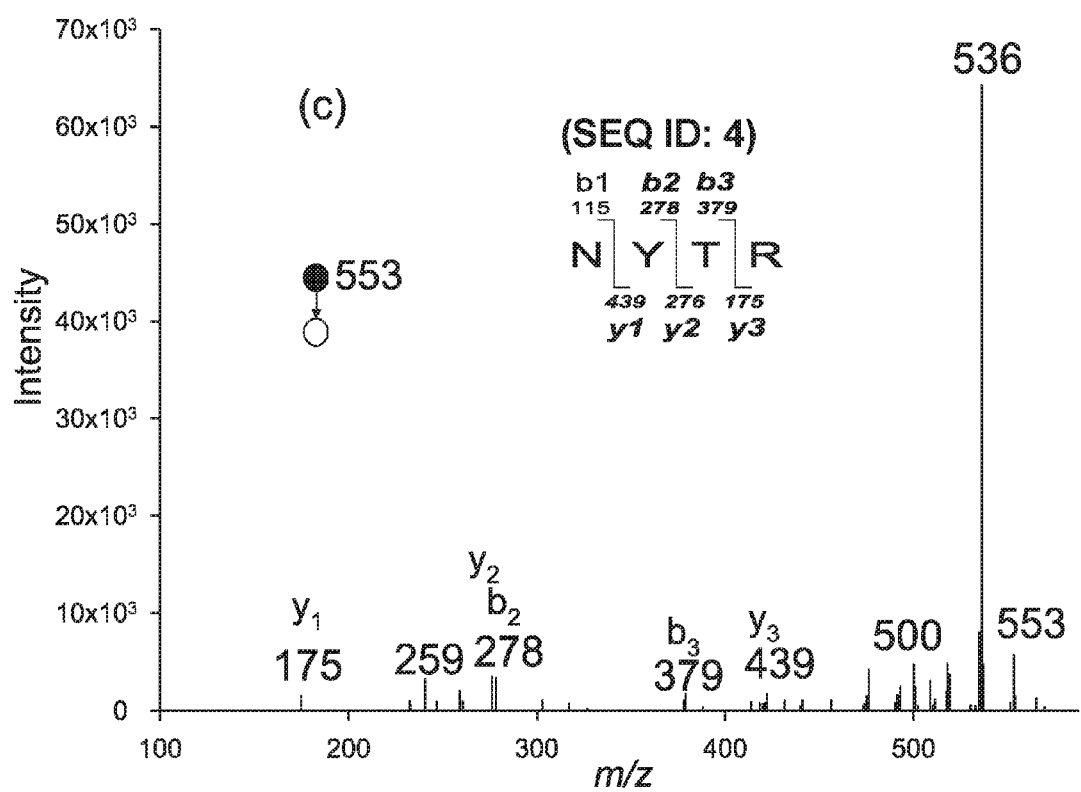
Figure 9A:
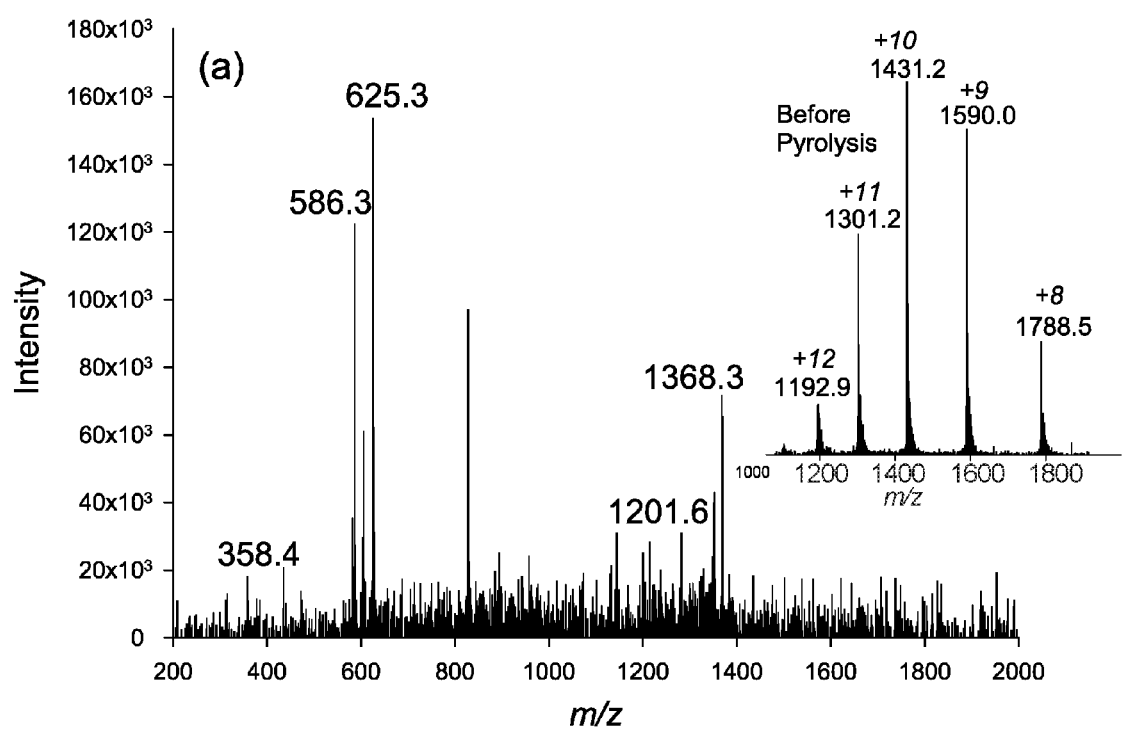
FIG. 9(A) is a diagrammatical view of the on-probe pyrolysis DESI-mass spectrum of lysozyme (inset: before pyrolysis DESI-mass spectrum)
Figure 9B:
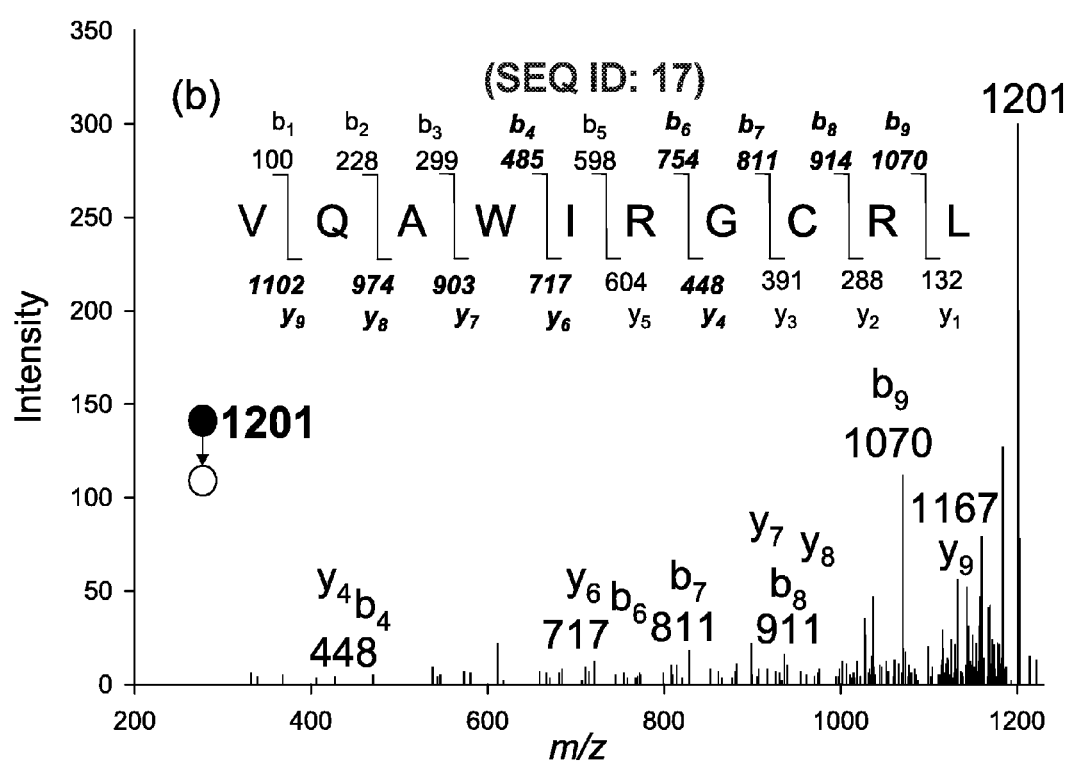
FIG. 9(B) a diagrammatical view of the on-probe pyrolysis DESI-tandem mass spectrum of the ion at m/z 1201.
Figure 10:
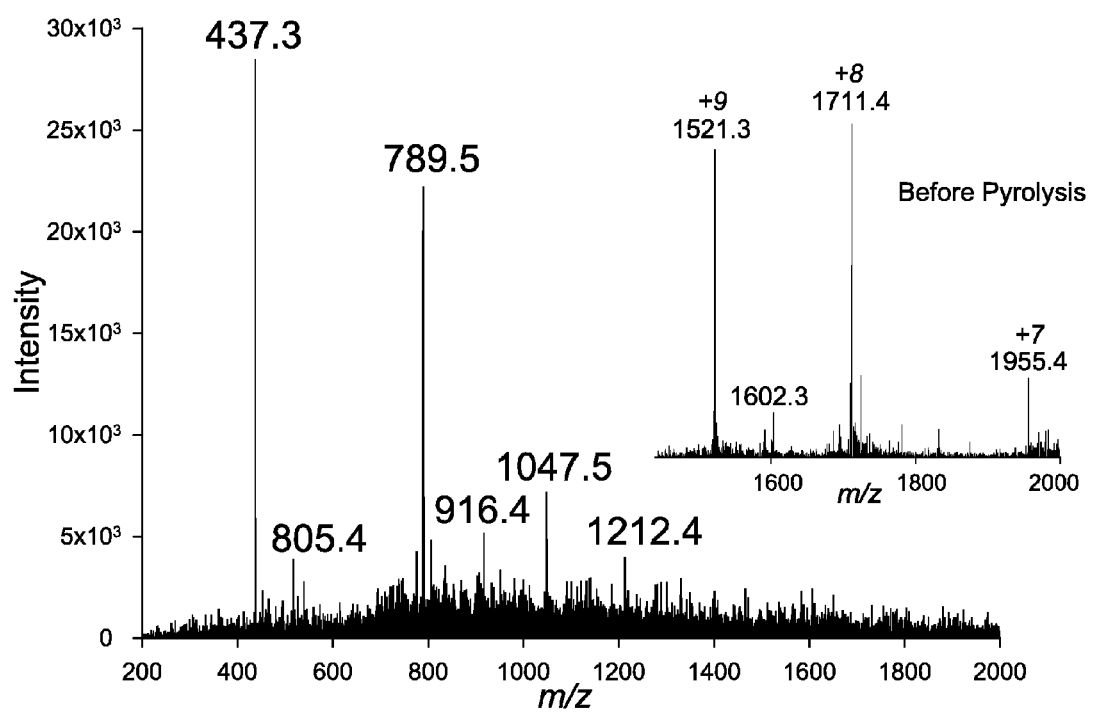
FIG. 10 is the on-probe pyrolysis DESI-mass spectrum of the protein RNase A (inset: before pyrolysis DESI-mass spectrum).

FIGS. 9A and 9B illustrate the on-probe pyrolysis and DESI-MS analysis of another peptide, VIP (1-12) peptide, which contains two aspartic acid residues. Specifically, the on-probe pyrolysis DESI-mass spectrum (FIG. 8A) is characterized by the ions at m/z 553.6 and 1086.3, which correspond to the expected products due to site-specific cleavages at the two aspartic acid residues (D-cleavage pyrolysis). This D-cleavage pyrolysis is believed to proceed via a similar mechanism as in the solution phase reaction, that is, the formation of a five-member cyclic anhydride followed by hydrolysis. Similar results were also obtained in the open-ended tube furnace (at atmospheric pressure conditions) and solvent extraction ESI-MS analysis of the pyrolysis residues. Other ions observed at m/z's 1068 and 1050 result from consecutive losses of water and ammonia (from arginine) from the pyrolysis fragment at m/z 1086.3, and these ions were also observed in the off-line pyrolysis and extraction ESI-MS measurements. FIGS. 8B and 8C show the on-probe DESI-tandem mass spectra of the pyrolysis products at m/z 1086 and 553, confirming their sequences and the site-specificity of the pyrolysis cleavage at aspartic acid. Also, the on-probe pyrolysis DESI-MS instrument was used to analyze the non-volatile pyrolysis products of the proteins lysozyme (MW 14.3 kDa) and RNase A (MW 13.7 kDa). FIGS. 9A and 9B show the DESI-mass spectra of lysozyme before and after pyrolysis and the DESI-tandem mass spectrum for the ion at m/z 1201. This ion corresponds to the protein C-terminus peptide due to D-cleavage pyrolysis as confirmed by the DESI-tandem mass spectral data in FIG. 9B. In previous work, it was successfully shown that this sequence information can be used to identify the protein via a proteomic-based approach and database search (e.g., MASCOT, Matrix Science Ltd., London, UK). FIG. 10 illustrates the on-probe pyrolysis DESI-MS analysis of the protein RNase A with the detection of several prominent pyrolysis products observed at m/z's 437.3, 789.5, 916.4, 1047.5 and 1212.4; however, none of the main signals observed match expected products resulting from D-cleavage pyrolysis. In previous investigations and in this study, the D-cleavage pyrolysis peptide product was derived from the C-terminus of the protein sequence, and not from cleavages of internal D groups.

On-Probe DESI-MS Analysis of Poly(Ethylene Glycol)

Figure 11A:
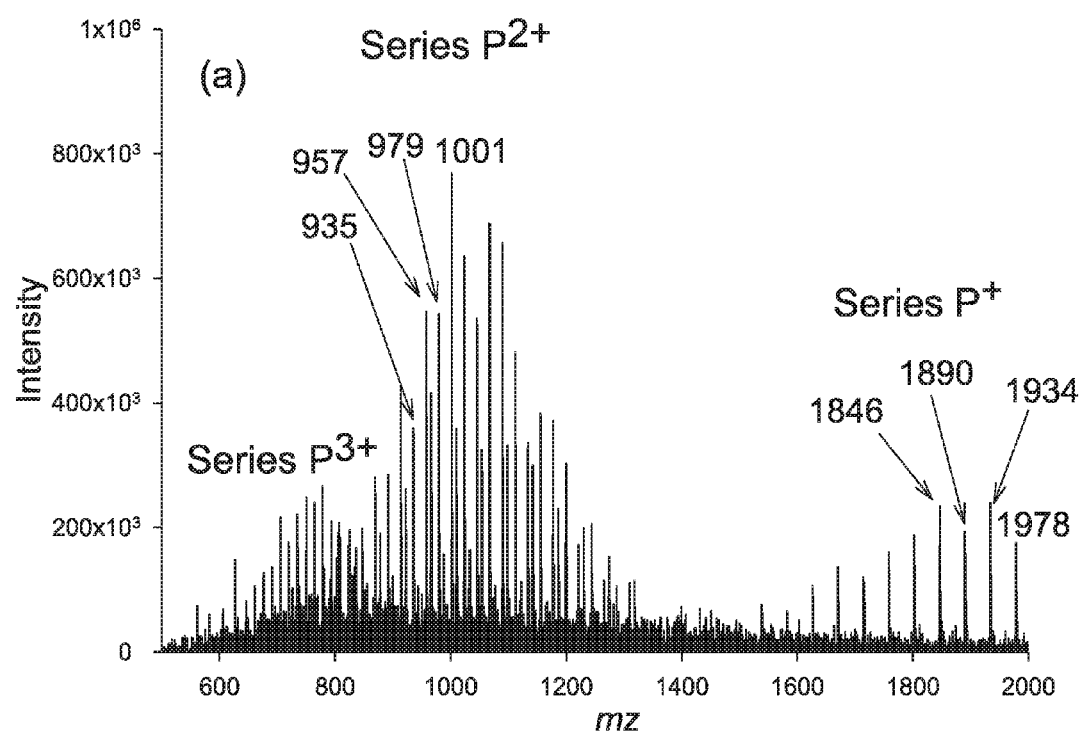
FIG. 11(A) is the DESI-mass spectrum of PEG 2000 before pyrolysis.
Figure 11B:
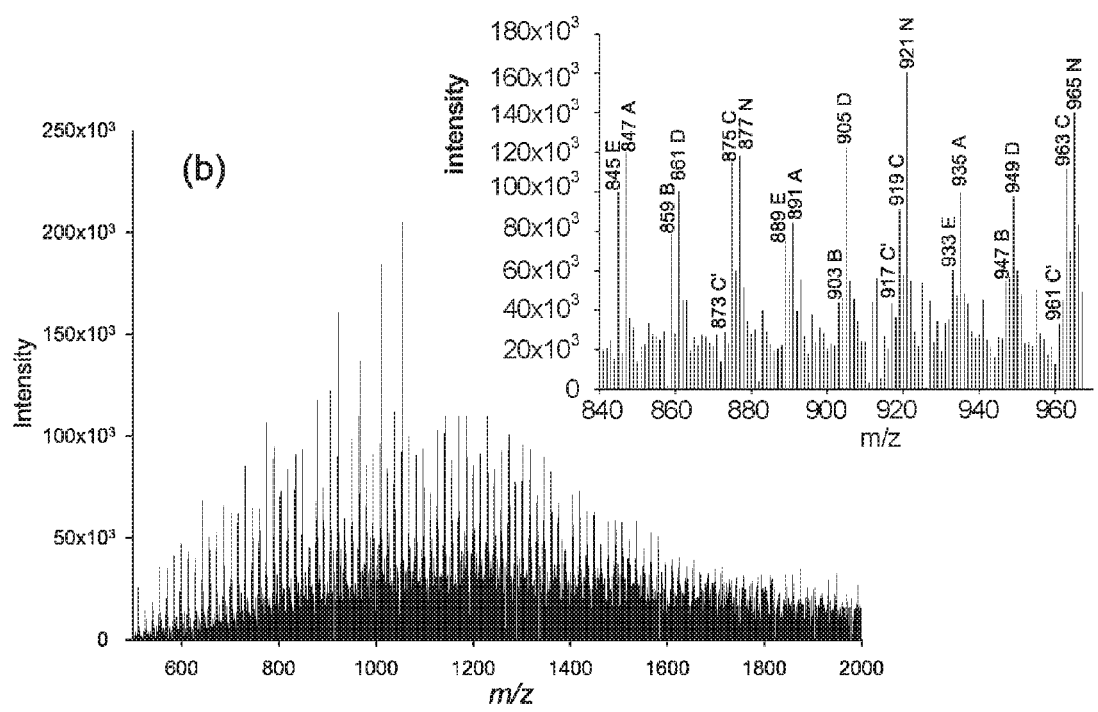
FIG. 11(B) is the on-probe pyrolysis (250° C., 30 min) DESI-mass spectrum of PEG 2000 (inset: zoomed mass spectrum in the range 840-970 Da).

Poly(ethylene glycol) with an average molecular weight of 2000 g/mol (PEG 2000) was used to test the ability of the on-probe pyrolyzer DESI-MS instrument to study thermal degradation processes in synthetic polymers. FIGS. 11A and 11B show the DESI-mass spectra of the PEG 2000 before and after onprobe pyrolysis at 250° C. for 30 min. The DESI-mass spectrum of untreated PEG 2000 (FIG. 6A) shows a distribution of singly charged ions near m/z 2000 as their $(M+Na)^+$ ions (monomer unit Dm=44 u) denoted in the spectrum as the $P^+$-series. A doubly charged $P^{2+}$-series is also observed near m/z 1000 (monomer unit Dm=22 u) and is composed of both $(M+2Na)^{2+}$ and $(M+Na+K)^{2+}$ ions. On the other hand, the on-probe pyrolyzed DESI-mass spectrum of PEG 2000 (FIG. 11B and inset) is strikingly different, with the $P^+$ series shifted to an average molecular weight near m/z 1000, while the $P^{2+}$ and $P^{3+}$ were not detected. Careful inspection of this mass spectrum (FIG. 11B inset) reveals the presence of several series of poly(ethylene glycol) with different end groups, and these are labeled using nomenclature coined by Voorhees et al. (Voorhees, K. J., Baugh, S. F., Stevensen, D. N. J. Anal. Appl. Pyrol. 30 (1994) 47-57)). The spectrum in FIG. 11B is dominated by the unmodified hydroxylpoly(ethylene) glycol series (labeled N in the spectrum), methyl ether series (A), aldehyde series (C) and the ethyl ether series (D). Less dominant, but present, are the vinyl ether series (B), the methyl ether/aldehyde series (E) and the methyl-vinyl ether series (CO). These results are in direct agreement with previous MALDI-MS studies (Lattimer, R. P. J. Anal. Appl. Pyrol. 56 (2000) 61-78) of the pyrolyzate residues of poly(ethylene glycol), proving that the on-probe pyrolysis DESI-MS technique described in this report yields comparable results. Moreover, the on-probe pyrolysis DESI-MS approach does not require matrix compounds, decreasing sample preparation time and avoiding matrix-sample adducts that can add to the chemical noise in the mass spectrum. Also, in this Example, no cationizing agent was added to either the polymer sample or the DESI solvent, and we believe the source of the $Na^+$ ions to be the glass slide and/or from trace amounts contained in the DESI solvent.

Conclusion

An on-probe pyrolyzer interfaced with desorption electrospray ionization (DESI) mass spectrometry and tube pyrolysis with sample extraction were successfully demonstrated to induce site specific cleavage at aspartic acid in biological samples. These results are in agreement with analyses of non-volatile pyrolysis products performed either by ESI-MS or MALDI-MS, which were pyrolyzed off-line and required sample extraction and solubilization. For biological samples and using the on-probe pyrolyzer DESI-MS system, it has here been demonstrated that pyrolysis residues of peptides and the protein lysozyme retain sequence information useful for proteomic-based protein identification. Moreover, these results demonstrate that atmospheric pressure pyrolysis can induce a variety of products that include site-specific cleavages at aspartic acid, dehydration reactions in peptides and proteins, and other products. For the analysis of poly(ethylene glycol), the on-probe pyrolysis DESI-MS system yielded data and information equivalent to previous MALDI-MS analysis, where the use of a matrix compound and cationizing agent were required. Quantitative to semi-quantitative analysis with DESI-MS is feasible, although quantitation of pyrolysis products was not addressed in this work. Overall, results from this work have demonstrated clear advantages of combining an on-probe pyrolyzer with a DESI source that include: minimum sample preparation, no sample extraction or transfer after pyrolysis, atmospheric pressure pyrolysis, rapid and atmospheric pressure detection by DESIMS, the ability for sample archival (samples on slides), and tandem-MS (if using a multistage-MS system).

Example 4

Site Specific Cleavage at Aspartic Acid Residue

This example concerns, inter alia, an automation of the sample preparation step for bottom-up proteomic analyses for microorganisms (i.e., biodetection) using a rapid reagentless approach for site-specific cleavage of peptides and proteins based on pyrolysis.

Experimental

The pyrolysis experiments were conducted using the device described previously in Example 1.

Chemicals

Peptides used were: 1) Angiotensin II, human DRVYIHPF (SEQ ID NO. 1); 2) VIP (1-12) peptide, HSDAVFTDNYTR (SEQ ID NO. 2); 3) VSV-G Peptide, YTDIEMNRLGK (SEQ ID NO. 3); 4) ACTH (1-10), SYSMEHFRWG (SEQ ID NO. 7); 5) Antioxidant peptide A, PHCKRM (SEQ ID NO. 8); 6) Somatostatin14, AGCKNFFWKTFTSC (SEQ ID NO. 9) (all from AnaSpec, San Jose, Calif.). The proteins: insulin (bovine pancreas, MW 5.7K), α-lactalbumin (bovine milk, MW 14K), lysozyme (chicken egg white, MW 14.3K), albumin (chick egg white, MW 42.8K), cytochrome C (horse heart, MW 11.7K) and MALDI matrix: sinapinic acid (SA) and α-cyano-4-hydroxycinnamic acid (CHCA) were all bought from Sigma and used without further purification. All solvents (water, methanol, acteonitrile (ACN)) used for sample preparation and MS measurements were HPLC grade (Burdick & Jackson, Muskegon, Mich.) and the formic acid (FA 96%) was ACS reagent grade (Aldrich, St. Louis, Mo.).

Bacteria

*Escherichia coli* (*E. coli*), *Staphylococcus aureus* (SA), *Pseudomonas aureginosa* (PA), *Salmonella typhimutium* (ST), were purchased from American Type Culture Collection (ATCC, Manassas, Va.). Bacteria were grown under optimum laboratory conditions using tryptic soy agar (TSA; BD Science, Sparks, Md.) at 37° C. for 12-15 h. Bacterial cells were transferred to 1 mL of water using a sterile tungsten loop inoculator. The cells were vortexed for 10 seconds and centrifuged for 5 minutes at 12,000 rpm to remove the media. The supernatant was removed and the pellet was re-suspended in 1 mL of water and the washing step was repeated for 3 times. After three washing steps the cells were dried by vacuum centrifuge before being pyrolyzed.

Mass Spectrometry and HPLC

The extracted solution of pyrolysis products was directly analyzed by HPLC separation step followed by online quadrupole io-trap MS (LCQ classic, Thermo Finnigan, San Jose, Calif.) equipped with a nano-electrospray ionization (nano-ESI) source.

For direct ESI analysis, sample was infused into the mass spectrometer at a flow rate of 3 μL/min via a 250-μL syringe (Harvard Apparatus, Holliston, Mass.) via a syringe pump. The mass spectra were collected using the LCQ Tune Plus software (Thermo Finnigan, San Jose, Calif.). Tandem MS (MS/MS) was conducted with the following parameters: activation q of 0.250; isolations width was 1 amu and the percentage relative collision energy was in the range of 25-40%, and was adjusted such that the relative abundance of the precursor ion in the product ion spectrum was approximately 30-50% relative intensity.

For HPLC-ESI-MS analyses, peptide mixtures from pyrolysis products were separated using an Ultimate/Switchos HPLC system (LC Packing, Sunnyvale, Calif.). A 1 μL aliquot of a peptide mixture solution was loaded onto a separation column (PepMap, C18, 150 mm*75 μm, 100 A, Dionex, Sunnyvale, Calif.), which had been equilibrated with 95% A (Solvent A: 20% ACN containing 0.1% FA, Solvent B: 100% CAN containing 0.1% FA). Peptides were separated using the following gradient at a flow rate of 300 nL/min: 0-10 min, 5% B; 10-60 min, 5%-60% B; 60-90 min, 100% B; 90-130 min, 100% A. The HPLC column eluate was connected to the nano-electrospray ionization (nESI) source of the LCQ. Tandem MS experiments with the ion trap MS were performed by acquiring a full-scan mass spectrum between m/z 300 and 2000 followed by three data dependent product ion mass-spectral scans of the most intense precursor ions (a.k.a "big-three" scan). The collision energy for dissociation was set at 30% with a 50 ms activation time. The dynamic exclusion feature of the Xcalibur software was enabled with a repeat count of 2, a repeat duration of 0.5 min, and exclusion duration of 2 min.

MALDI-MS experiments were performed using a Voyager DE-PRO (Applied Biosystems, Foster City, Calif.) instrument equipped with a $N_2$ laser and operated in the reflection mode. The matrix α-cyano-4-hydoxy-cinnamic acid (CHCA) was used for all measurements and was prepared by dissolving 10 mg of CHCA in a 1 mL solution of 1:1 acetonitrile/water with 0.1% trifluoroacetic acid (TFA) (Pierce Chemical Company, Rockford, Ill.). The extracted solution of pyrolysis products was directly mixed with the matrix at different volume ratios and air-dried onto a MALDI plate.

Results and Discussions

1. Pyrolysis Induced Cleavage at Aspartic Acid (D-Cleavage)

Several model peptides containing aspartic acid were pyrolyzed, their non-volatile products analyzed by ESI-MS, and their amino acid sequences confirmed by tandem MS: 1, Angiotensin II, human, DRVY1HPF (SEQ ID NO. 1); 2, VIP (1-12) peptide, HSDAVFTDNYTR (SEQ ID NO. 2); 3, VSV-G Peptide, YTDIEMNRLGK (SEQ ID NO. 3); 4, ACTH (1-10): SYSMEHFRWG (SEQ ID NO. 7). Angiotensin II was pyrolyzed at different temperatures to probe the pyrolysis temperature's effect on the distribution of pyrolytic products. Angiotensin II was tested at pyrolysis temperatures of 200, 200, 250 and 290° C. The ESI-mass spectra of the pyrolytic products under various temperatures are shown in FIGS. 1A-C.

For the peptides tested at pyrolysis temperature of 200° C. The ESI-mass spectra of the pyroltic products under various temperatures are shown in FIGS. 1A-C.

For the peptides tested at pyrolysis temperatures of 200° C. and lower, no significant pyrolysis fragments were detected. At the other extreme, pyrolysis temperatures of 290° C. and higher, yielded extensive fragmentation products which were most likely due to peptide carbonization. At pyrolysis temperatures between 220° C. and 250° C., several products are detected and correspond to the pyrolysis fragment due to C-terminal cleavage at aspartic acid (detected at m/z 931.6). Tandem MS (MS/MS) of this ion (FIG. 2) confirmed the sequence RVYIHPF (SEQ ID NO. 10), the product of a C-terminus cleavage at the aspartic acid residue of angiotensin II. Other peaks present in the spectrum were observed at m/z 1028.5 (18 amu less than parent ion) and at m/z 1011.5 (17 amu less), which are believed to be a water loss (from the C-terminus) and ammonia loss (from arginine) respectively.

Figure 12A:
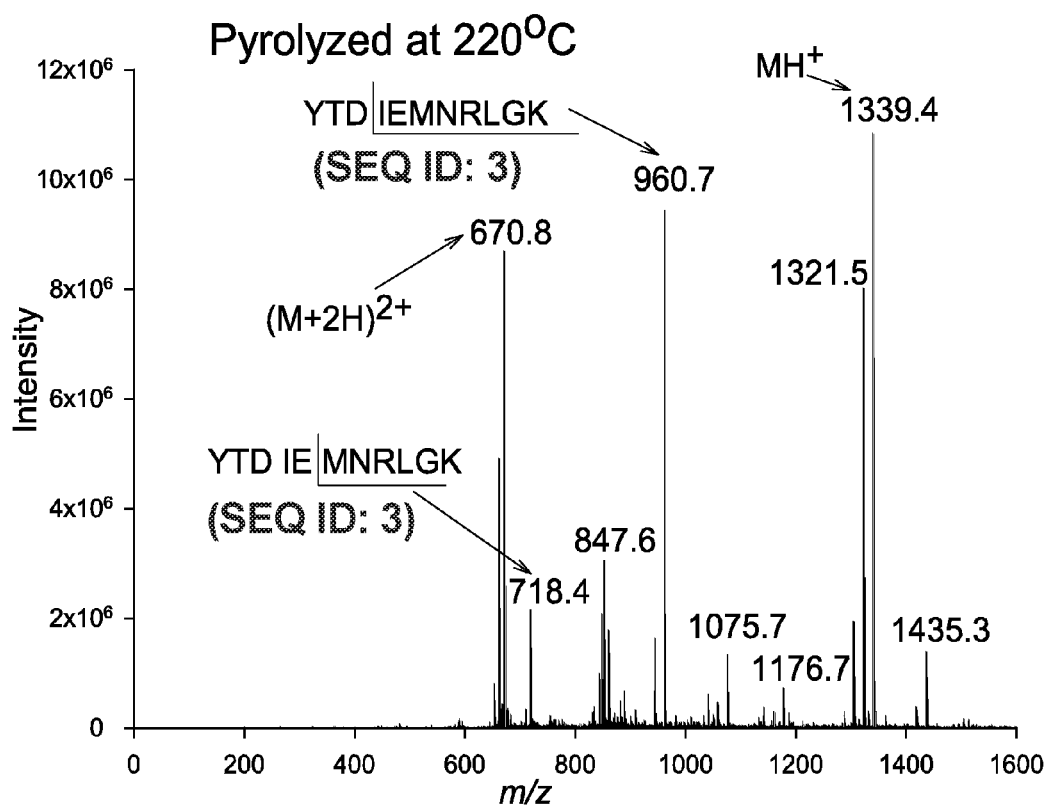
FIG. 12(A) is and ESI-MS spectrum of pyrolysis products of the VSV-G peptide showing site specific cleavage at the aspartic acid site.
Figure 12B:
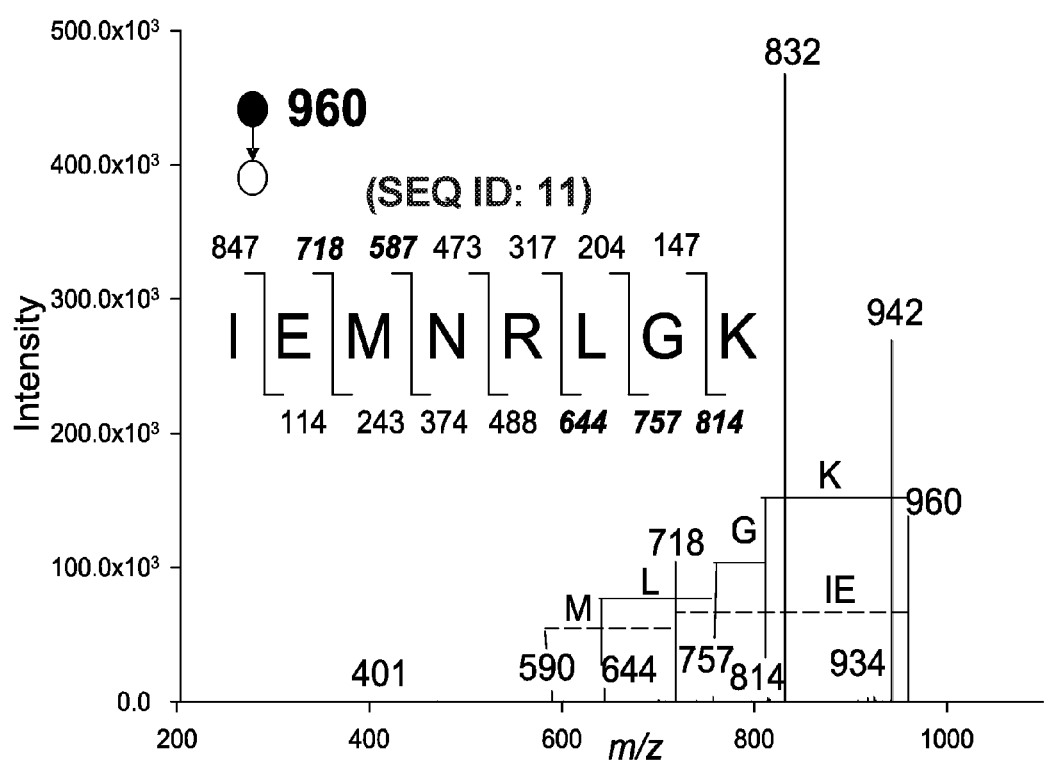
FIG. 12(B) is an $MS^2$ spectrum of the specific pyrolysis products of the VIP (1-12) peptide, confirming its sequence.

The same experiments were carried out on VIP (1-12) peptide, of sequence HSDAVFTDNYTR (SEQ ID NO. 2). Site specific pyrolysis-induced cleavage was also observed for this peptide, which contains two aspartic acid residues (ESI-mass spectrum shown in FIGS. 3A and 3B). After pyrolysis at 220° C., non-volatile peptide products are observed with the ions at m/z 1086.5 (AVFTDNYTR) (SEQ ID NO. 4) and m/z 553.6 (NYTR) (SEQ ID NO. 5), corresponding to cleavages at each of the two aspartic acid C-terminus sites. Amino acid sequences of these pyrolysis products were confirmed by MS/MS measurements (shown in FIGS. 4A and 4B). Also, another peptide reaction products was observed at m/z 1521 for VIP (1-12) peptide corresponding to the addition of trifluoroacetic acid (TFA, used to acidify solutions) to the N-terminus and at m/z 1435 for VSV-G Peptide (FIGS. 12A and 12B).

Figure 13:
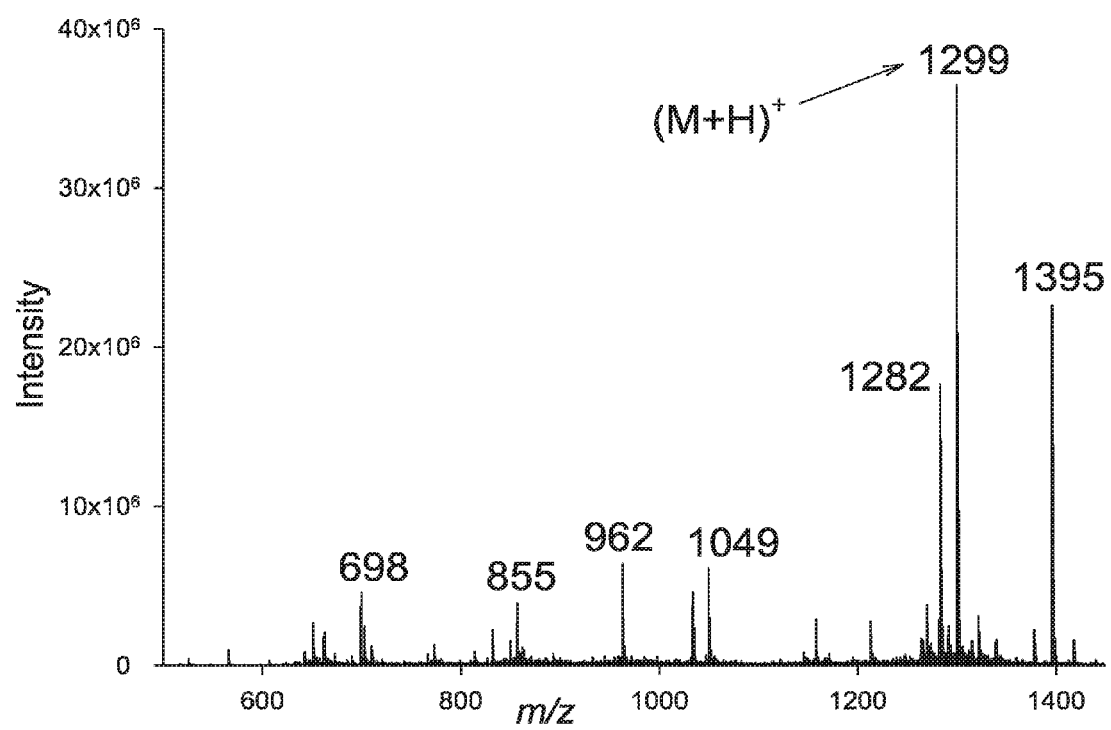
FIG. 13 is a full scan mass spectrum of pyrolysis products of peptide ACTH (1-10); the cleavage product at E with m/z 702 was not observed.

The same experiments were carried out for VSV-G Peptide, YTDIEMNRLGK, which contains the amino acids D and E (glutamic acid). The ESI full scan spectrum of pyrolytic products is shown in FIGS. 5A and 5B. The signal at m/z 960.7 corresponds to the sequence of 1EMNRLGK (SEQ ID NO. 11), a product corresponding to cleavage at D. However, a new peak at m/z 718.4 was also observed MS$^2$ experiment of this peak shows its sequence is MNRLGK (SEQ ID NO. 12), a pyrolytic product corresponding to cleavage at the C-terminus of E. Considering the similarity between D and E where both of them have a carboxylic acid in their branch chains, more experiments were don to test where E is a possible cleavage site, hence other peptides contains E but without D were tested. Peptide ACTH (1-10): SYSMEHFRWG (SEQ ID NO. 7) was tested. The full scan mass spectrum of its pyrolyzed products is shown in FIG. 13, however the expected cleavage product of E of m/z 702 was not observed.

These results demonstrate that pyrolysis at temperatures between 220° C. and 250° C. favors cleavage in peptides at the C-terminus of D. Peptide fragmentation at the C-terminus of D is believed to proceed via the formation of a five-member cyclic anhydride followed by hydrolysis, since pyrolysis is performed in air and at atmospheric pressure.

Example 5

Pyrolysis Induced Cleavage at Cysteine
(C-Cleavage)

The ability of the pyrolysis-based digestion method to produce sequence-specific biomarkers has been demonstrated for peptides and the protein lysozyme. However, only the fragment near to the C-terminus of the protein sequence has been identified, namely m/z 1201 corresponding to the D cleavage. In order to identify other prominent peaks in FIGS. 8A-C such as 828, 1328 etc., tandem MS measurements were conducted on them.

Figure 14:
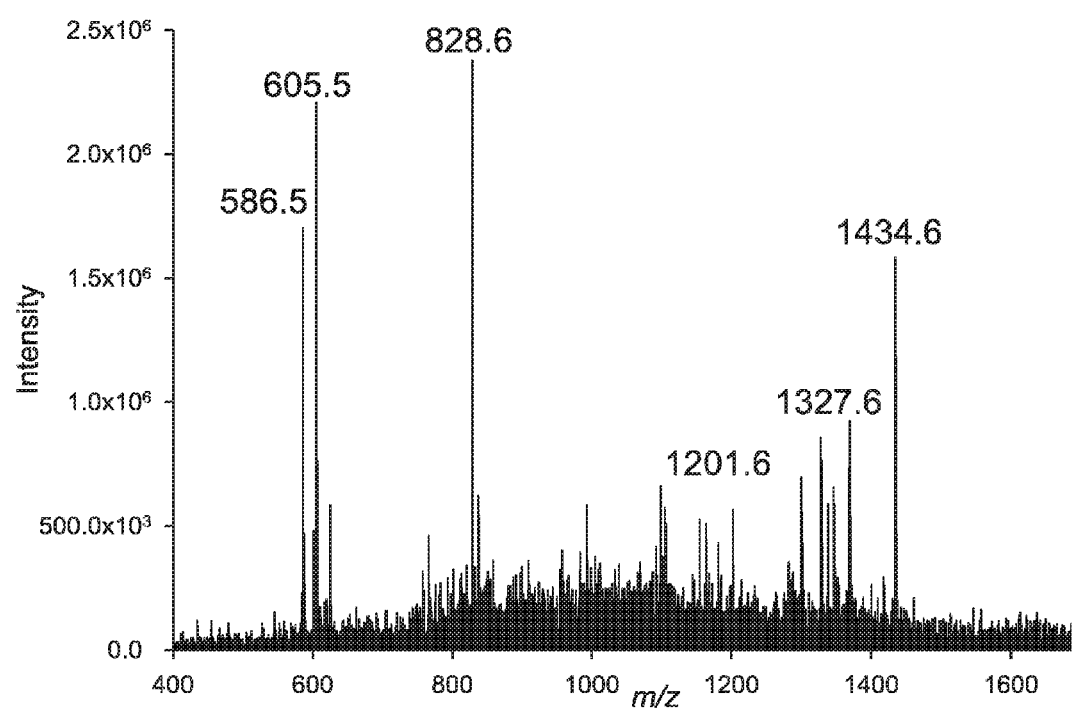
FIG. 14 is an ESI full scan mass spectrum of pyrolysis products of the protein lysozyme.
Figure 15A:
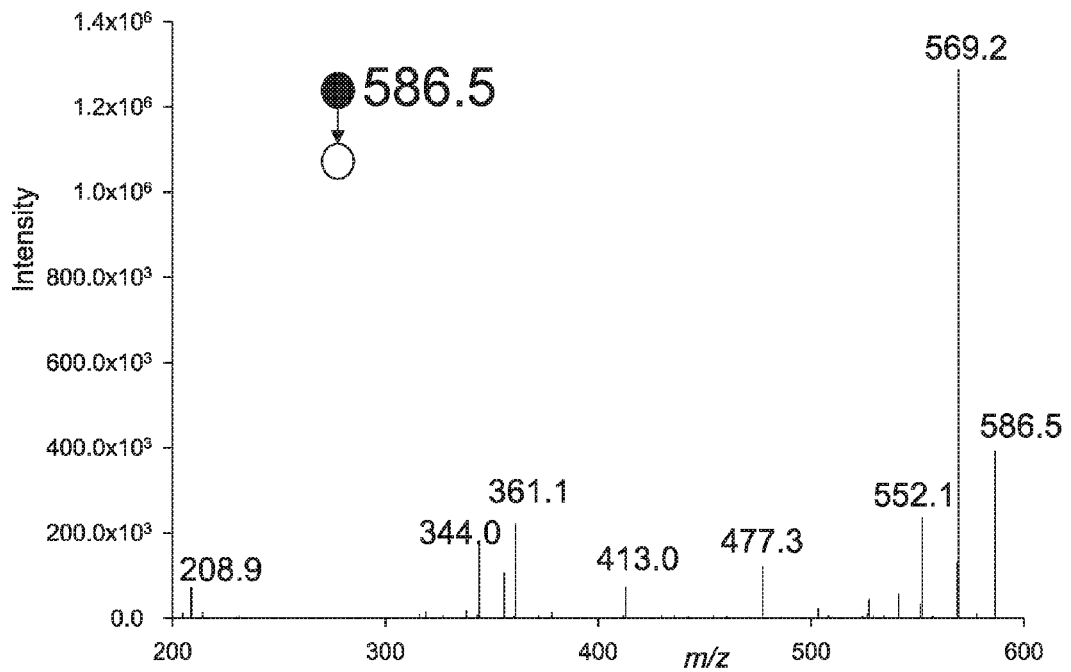
FIGS. 15 (A-E) are charts of the MS/MS spectra of ions m/z 586.5, 605.6, 828.6, 1327.6, and 1434.6, respectively.
Figure 15B:
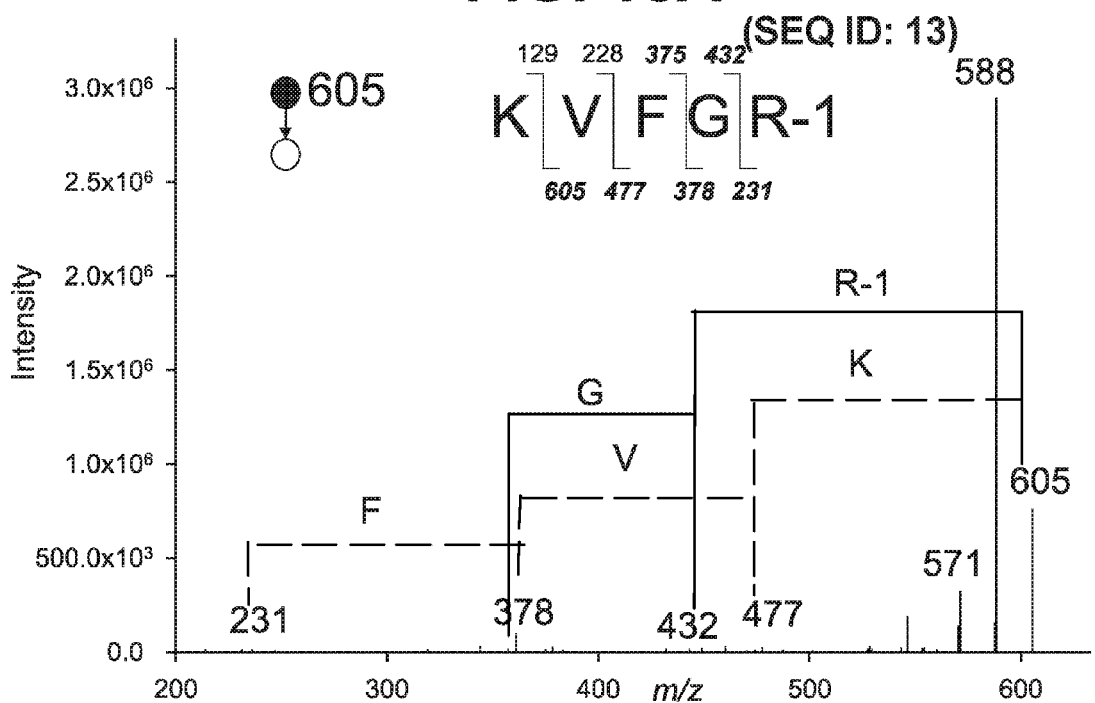
Figure 15C:
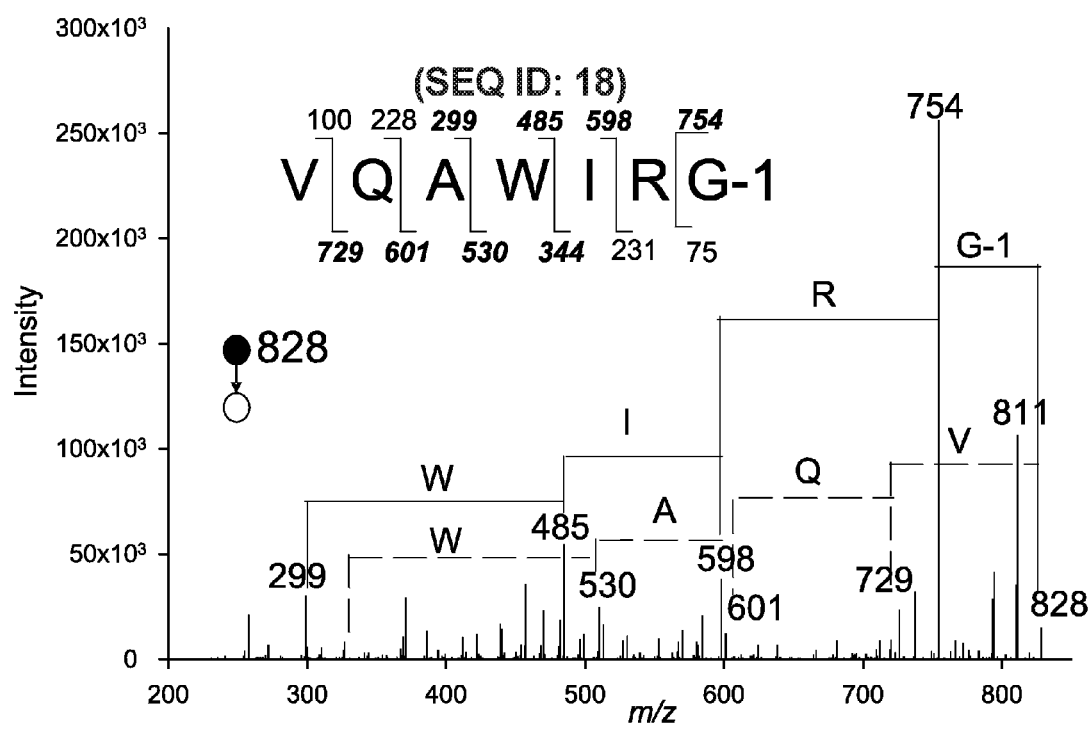
Figure 15D:
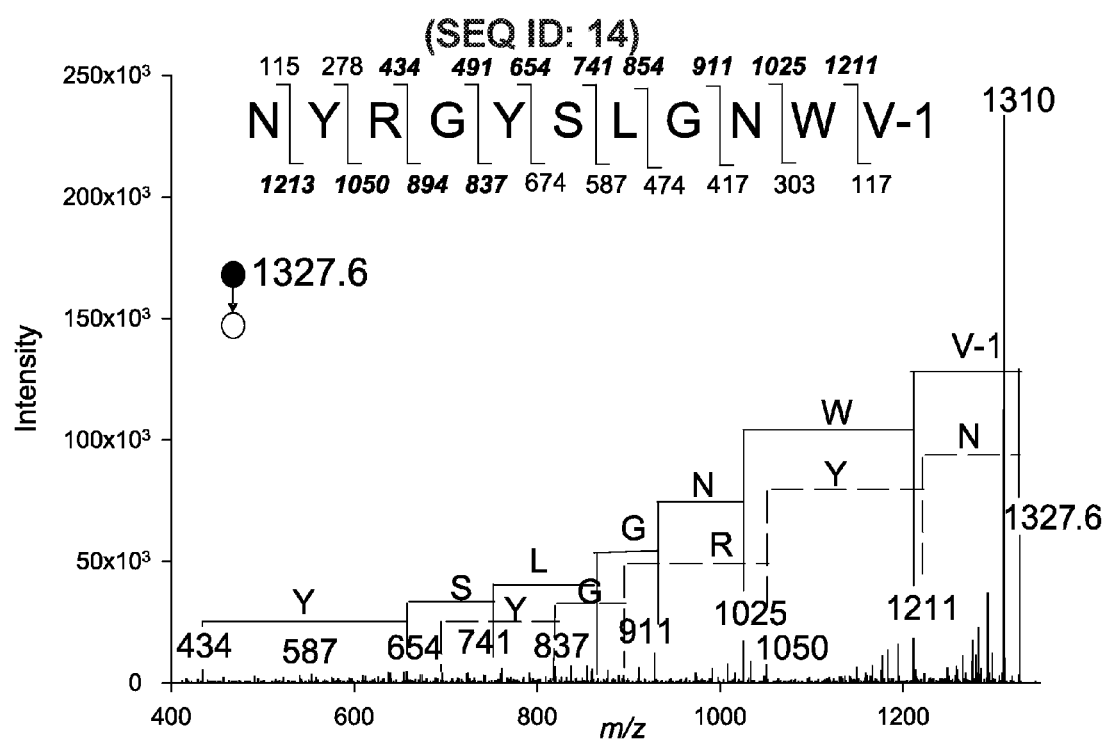
Figure 15E:
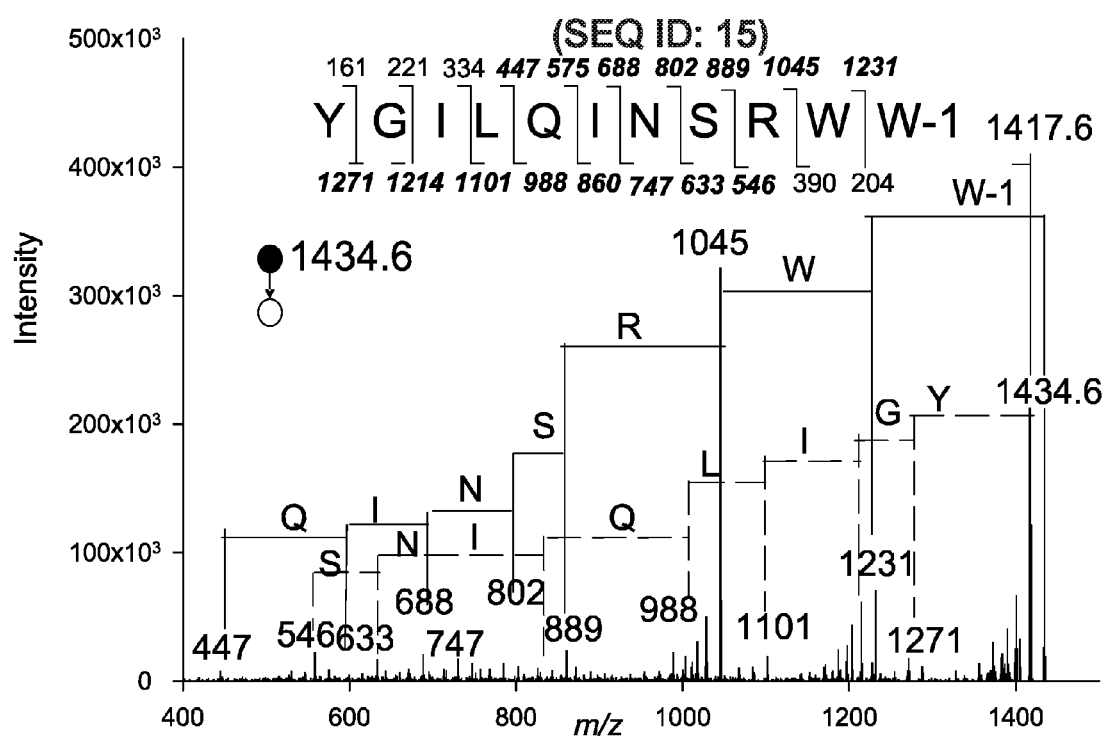

The ESI full scan spectrum of pyrolyzed lysozyme at 220° C. is shown in FIG. 14 and the MS/MS spectra of m/z 586.5, 605.6, 828.6, 1327.6, 1434.5 are shown in FIGS. 15A-E, respectively.

Figure 16:
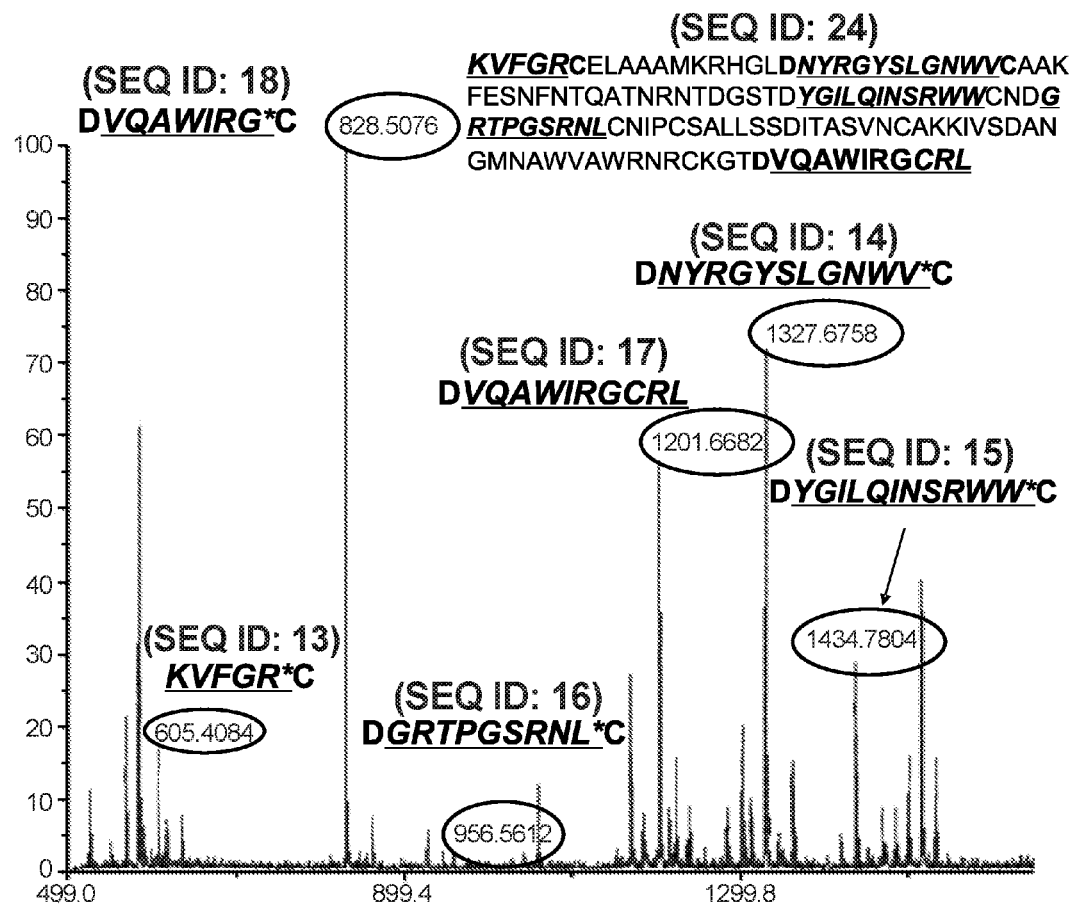
FIG. 16 is a chart of the observed peptide fragments according to the cleavage rules after pyrolysis of protein lysozyme.

Careful inspection of this serial of MS/MS mass spectra (FIGS. 15A-E) reveals that pyrolysis indeed induced the cleavage of the protein lysozyme mot only at the C-terminus of D, but also induced cleavages at the N-terminus of cysteine residues, with the added −1 Da mass modification at the amino acid to the C terminal side of the cysteine. The structure of the −1 mass modification is under further investigation and we believe it to be an amide (R—CO—NH$_2$) replacing the original—OH group at the C-terminus of a peptide. This result shows that pyrolysis is a very promising protein digestion approach, as it can generate small peptide fragments (which are desired by mass spectrometry measurements) by site-specifically cleaving at two different amino acid sites. FIG. 16 shows the observed peptide fragments according to the (revised) pyrolysis DC-cleavage rules and it can be seen that the majority of the prominent peaks are assigned.

Figure 17:
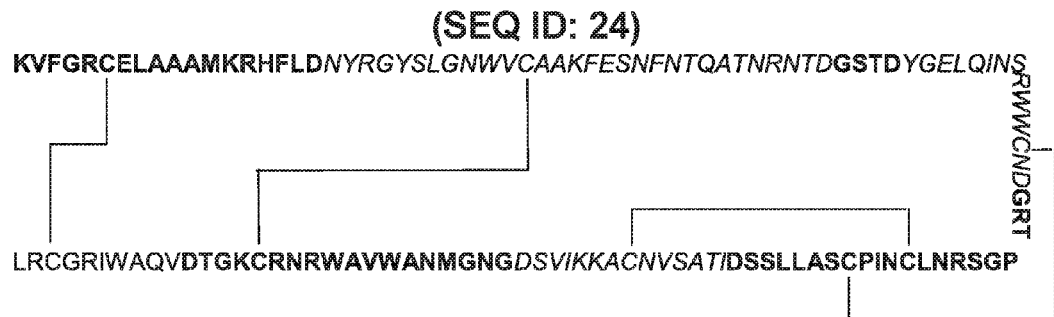
FIG. 17 is a chart of the disulfide bond sites in lysozyme.

When both of the two-site cleavages considered, very good sequence coverage (42%) of lysozyme is obtained (FIG. 16). Worth to note that disulfide bonds connecting two cysteine residues in a polypeptide chain must be broken during the pyrolysis of lysozyme as well, when we take a look at the disulfide bond sites in lysozyme (FIG. 17).

The disulfide bonds have to be broken to generate the observed peptide fragments of sequences KVFGR*C (SEQ ID NO. 13) (MH$^+$605.7), DNYRGYSLGNWV*C (SEQ ID NO. 14) (MH$^+$1327.8), DYGILOINSRWW*C (SEQ ID NO. 15) (MH$^+$1434.6), DGRTPGSRNL*C (SEQ ID NO. 16) (MH$^+$956.8), DVQAWIRGCRL (SEQ ID NO. 17) (MH$^+$1201.6), DVQAWIRG*C (SEQ ID NO. 18) (MH$^+$828.7), providing further evidence that disulfide bonds are broken during pyrolysis. This valuable feature of pyrolysis-induced protein digestion eliminates the disulfide bond breaking step that usually involves and extra and time-consuming step necessary prior to enzymatic and chemical digestion methods[16]. In an enzymatic or chemical digestion procedure, cleavage of disulfide bonds commonly involves chemical digestion procedure, cleavage of disulfide bonds commonly involves chemical reduction of disulfide bonds (R—S—S—R$^1$) to thiol groups (R—SH) with the addition of dithiothreitol, followed by alkylation of the reduced cysteines to prevent the residues from reforming their bonds through oxidation[16]. The whole process needs 30 minutes to several hours, further adding to the total analysis time required for protein identification.

To test the ability of the pyrolysis-induced specific-cleavage at cysteine and to break disulfide bonds, more peptides and proteins containing cysteine residue(s) were examined.

Figure 18A:
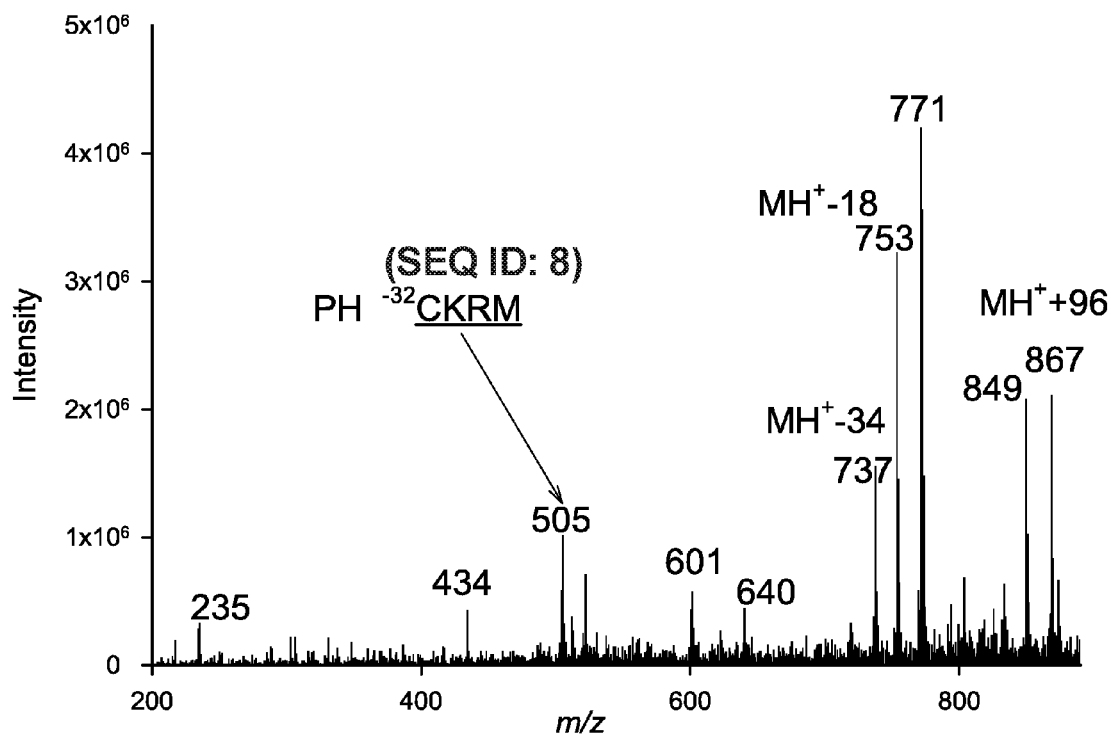
FIG. 18(A) is a chart of the ESI full scan of peptide Antioxidant A after pyrolysis and FIG. 18(B) the MS/MS spectrum of m/z 505, the C-cleavage product.
Figure 18B:
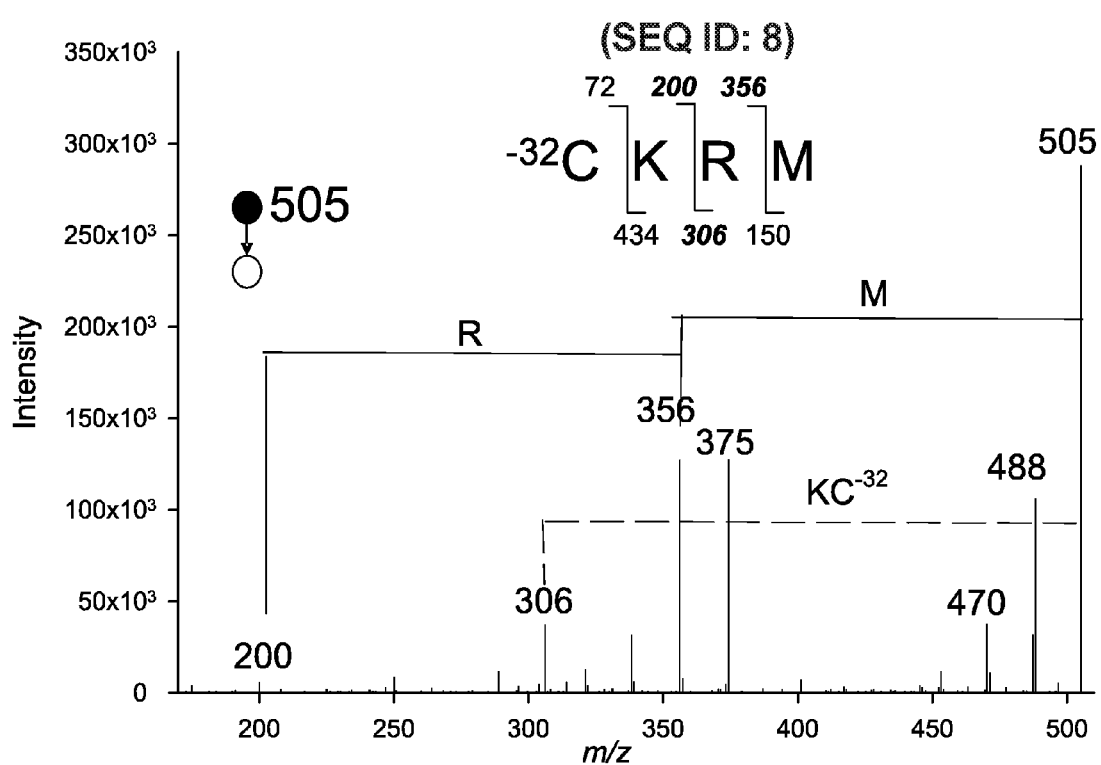
Figure 19A:
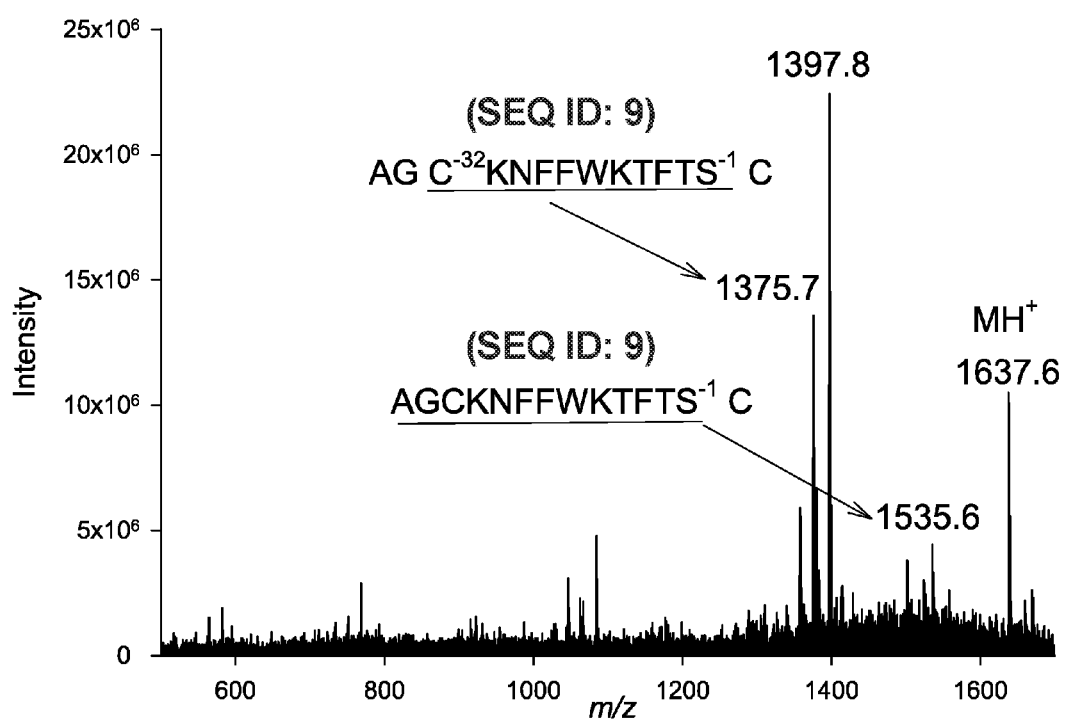
FIG. 19(A) is a chart of the ESI full scan of peptide Somatostatin 14 after pyrolysis and FIGS. 19(B) and 19(C) the MS/MS spectrum of m/z 1535.6 and 1575.6, the C-cleavage products, respectively.
Figure 19B:
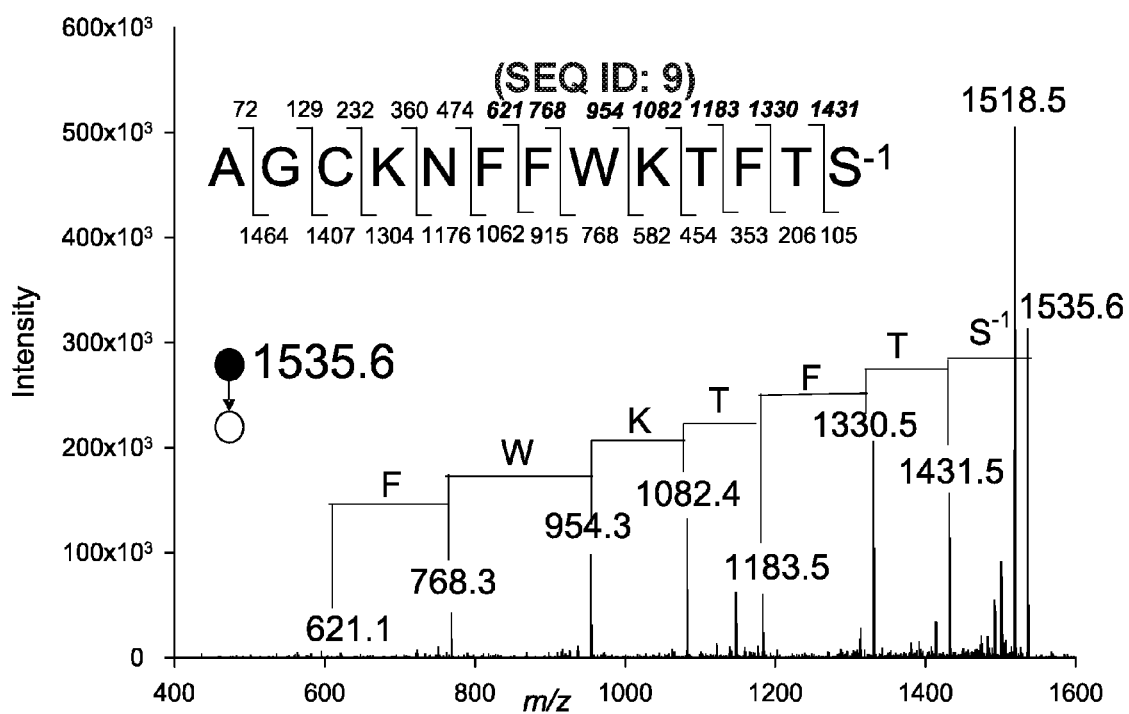
Figure 19C:
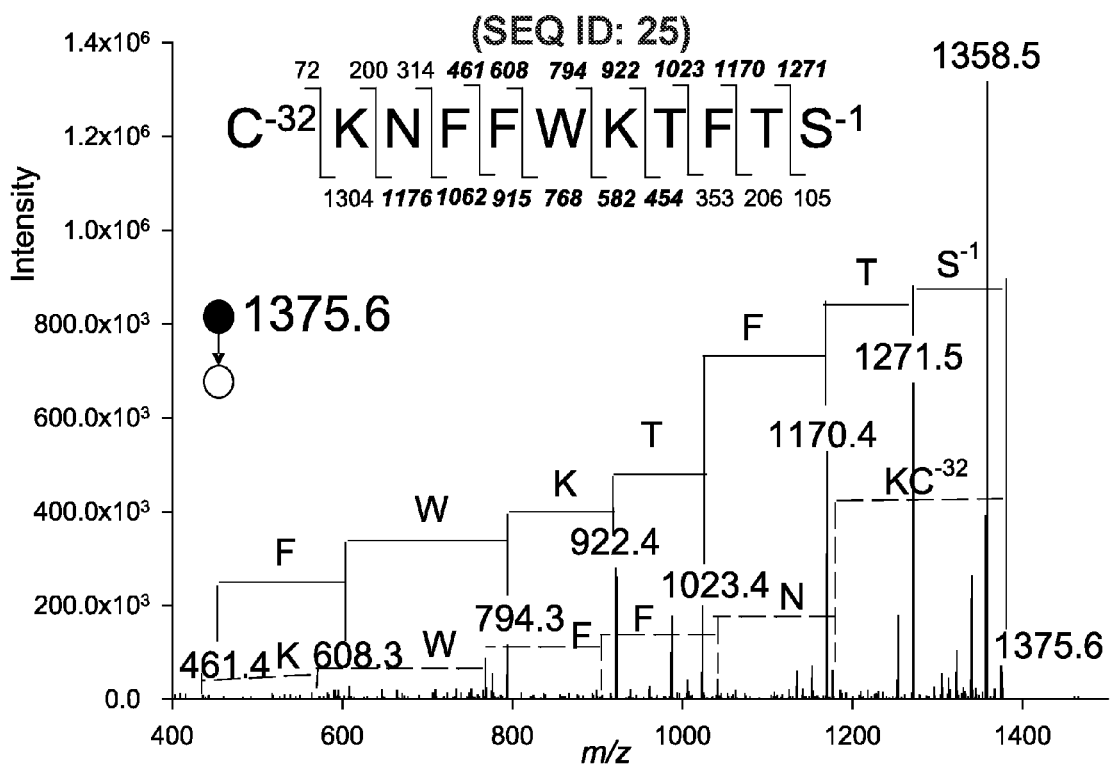

Two more peptides containing cysteine residue(s) were tested: Antioxidant peptide A, PHCKRM (SEQ ID NO. 8) (FIGS. 18A and 18B), and Somatostatin14, AGCKNFFWK-TFTSC (SEQ ID NO. 9) (disulfide bond between the two cysteines) (FIGS. 19A-C).

FIGS. 14 and 15 illustrate that pyrolysis indeed induces the two tested peptides to cleave at the N-terminus of cysteine. For peptide Antioxidant A, the C-terminal cleave at the N-terminus of cysteine. For peptide Antioxidant A, the C-terminal side peptide fragment after cleavage at cysteine is observed at m/z 505 and the MS/MS confirms its sequence. Furthermore, the mass calculation and MS/MS data show that the C-terminal side peptide fragment after C-cleavage has a modification of 32 Da mass less than the original cysteine residue. Recall that in the protein lysozyme, the N-terminal side peptide fragment after C-cleavage possesses a modification of 1 Da mass less than the original, unmodified residue In the spectra of the pyrolyzed peptide Somatostatin14, cleavages at both of the two cysteines take place, both of the C, N terminal peptide fragments are present and both of the mass modifications (−32 and −1) are observed, further increasing the validity of the C-cleavage rule. Again, the sequences of the specific cleavage framents (m/z 1535.6 and 1375.6) are confirmed by MS/MS. Moreover, the disulfide bond between the two cysteins proved to be broken by pyrolysis from the two fragments of m/z 1535.6 and 1375.6.

Example 6

Pyrolytic Digestion of Proteins and their Identification

More proteins containing just cysteine (insulin bovine) and containing both cysteine and aspartic acid α-lactalbumin (bovine milk), albumin (chick egg white), cytochrome C (horse heart)) were tested. Also, their MS/MS date were used to identify the protein via database search—Mascot and Sequest V.3.3.1 (Thermo, San Jose, Calif.).

First, the date search was performed on the protein lysozyme. The MS/MS data of ions at m/z 605, 828, 1201, 1327 and 1434 were manually extracted into a "*.dta" format file (format used by most database searches), which contains the precursor ion's mass and charge, and the fragmentation ions' mass and intensity. The searching parameters are as follows and used for all the following searches. Database: MSDB Taxonomy: All entries; Enzyme: None; Allow up to 1 missed cleavages; No modifications; No quantitation; Peptide tol.: ±2 Da; MS/MS tol: ±1.5 Da; Peptide Charge:1+, 2+, 3+; Monoisotopic; Data format: Sequest (.DTA); No precursor; Instrument: Default; No error tolerant; No Decoy; Report top Auto hits.

Figure 20A:
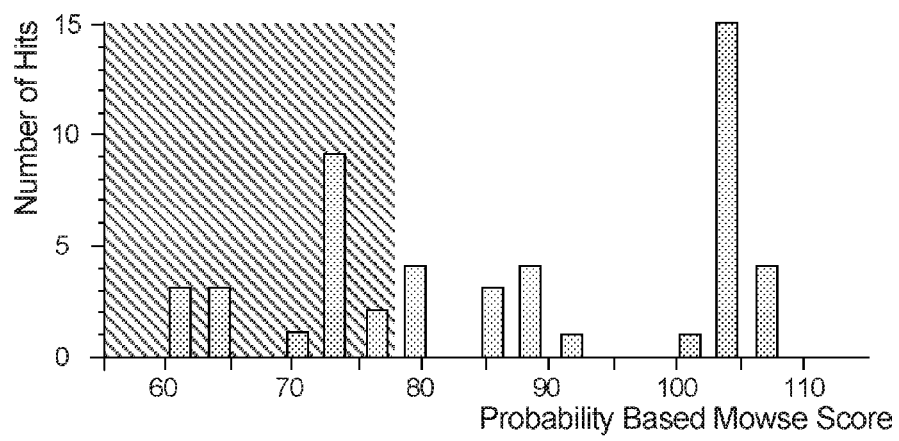

FIGS. 20A-C show the Mascot search results of lysozyme. Protein Lysozyme is successfully identified with a very high score.1. Recall that a score of 52 was obtained when ion m/z 1201 alone was used in the search. In this search five of the pyrolysis DC cleavage products are applied, the score jumps to as high as 107, further increasing the identification's specificity. Moreover, the sequences of all of the fragment ions are correctly shown with the corresponding −1 Da modification (as the error of the match or "Delta" value. This is the case because the web-based free access algorithm cannot take into account user-specified chemical modifications. A licensed version of this software is needed for this ability). The searching results of lysozyme are very encouraging, showing that a simple process as high temperatures heating or pyrolysis has the ability to digest proteins with site-specificity and therefore identity the protein via bottom-up proteomics. Furthermore, because the free version of Mascot used cannot allow editing our own "enzyme", the "no enzyme" option was selected. We believe a much better and more specific search result could be obtained if an accurate "enzyme" (namely the pyrolysis cleavage before C and after D with a all chemical modifications) were used.

Mass spectral data for lysozyme (containing full scans and MS/MS scans) was searched by another searching engine, Seaquest. Sequest is an algorithm that searches within a database containing peptide fragmentation spectra from known proteins for matches to spectra attained in the experiment[17, 18]. In the Sequest search, an in silico "enzyme" was created within the BioworksBrowser™ to perform the pyrolysis digestion at D and C residues. However, in establishing the search parameters, "partially cleavage at either side" was selected, because of limiting flexibility in the "enzyme" editing. That is, the software does not allow to generate an in silico enzyme which cleavages at different sides of two residues, for example, to cleave at N-terminus or C and C-terminus of D. The other parameters used in the search include up to 10 missed cleavage sites, group scan of 50, minimum group count of 1, minimum ion count of 12, the charge state option was set to auto, and the C-terminal peptide variable modification set as −1. The above parameters are used for all the following searching, unless otherwise specified. The Sequest search of the entire database successfully identified the protein lysozyme with a probability score of 6.3E6 and Xc score of 36 and both of the two scores are very good. However, only two (1328, 1435) of the 5 expected fragments are detected/identified by Sequest, compared to 5 out of 5 found by the Mascot database search.

The same Sequest search is conducted to lysozyme, but within the database of chicken proteins. The probability score of 1.2E5 and a better Xc score of 56 gained. Furthermore, 4 (828, 1201, 1328, 1435) of the 5 expected fragments are identified by Sequest, showing a better search result if the protein source can be narrowed down.

Figure 21A:
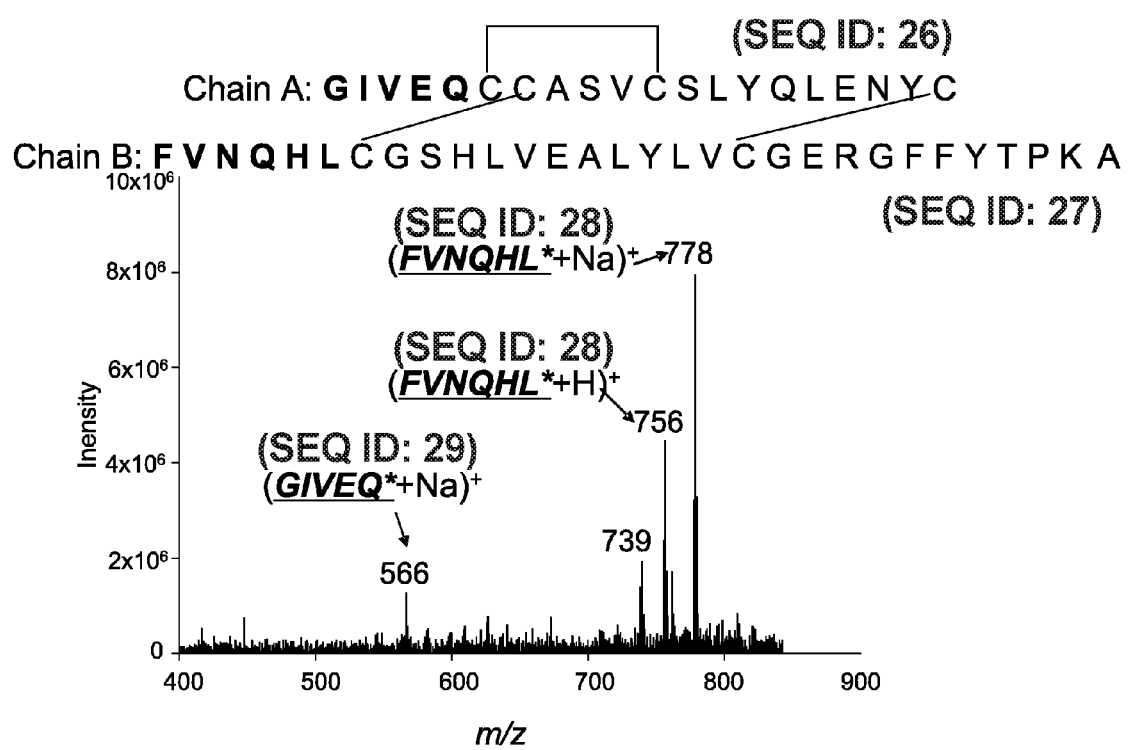
FIGS. 21 (A)-(C) show the ESI full scan mass spectrum of the protein insulin after pyrolysis and the MS/MS mass spectra of m/z 566 and 778.
Figure 21B:
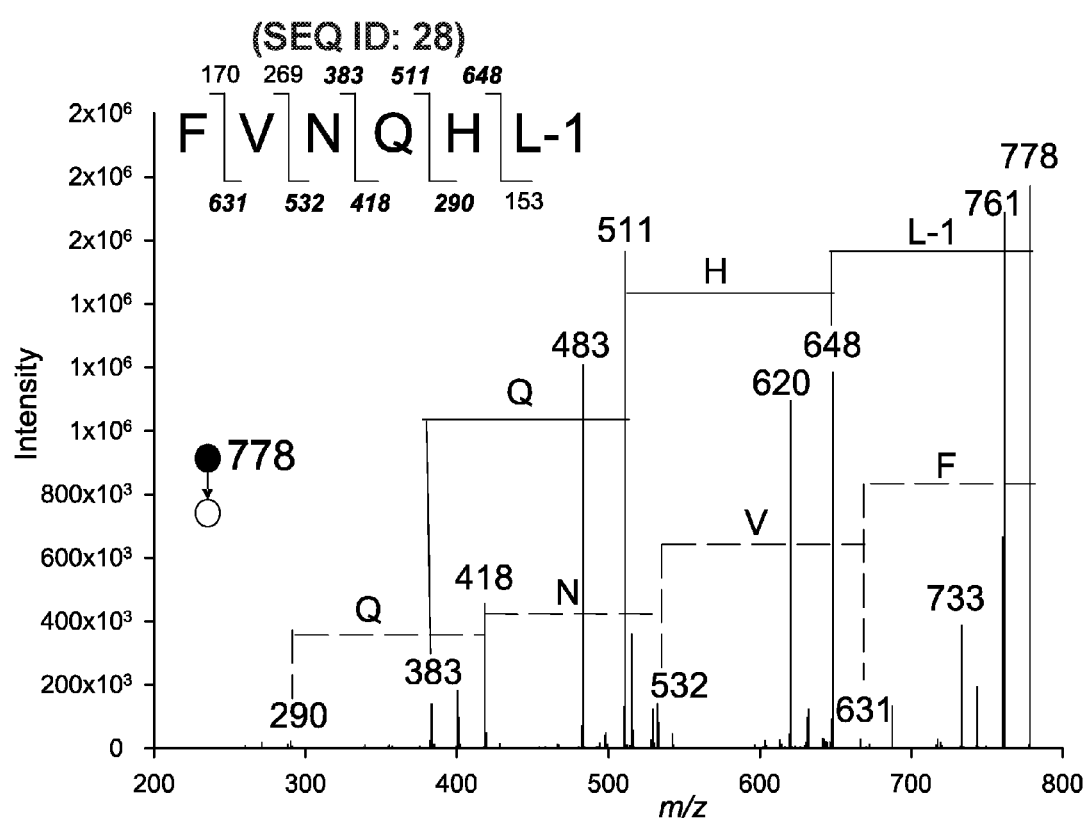
Figure 21C:
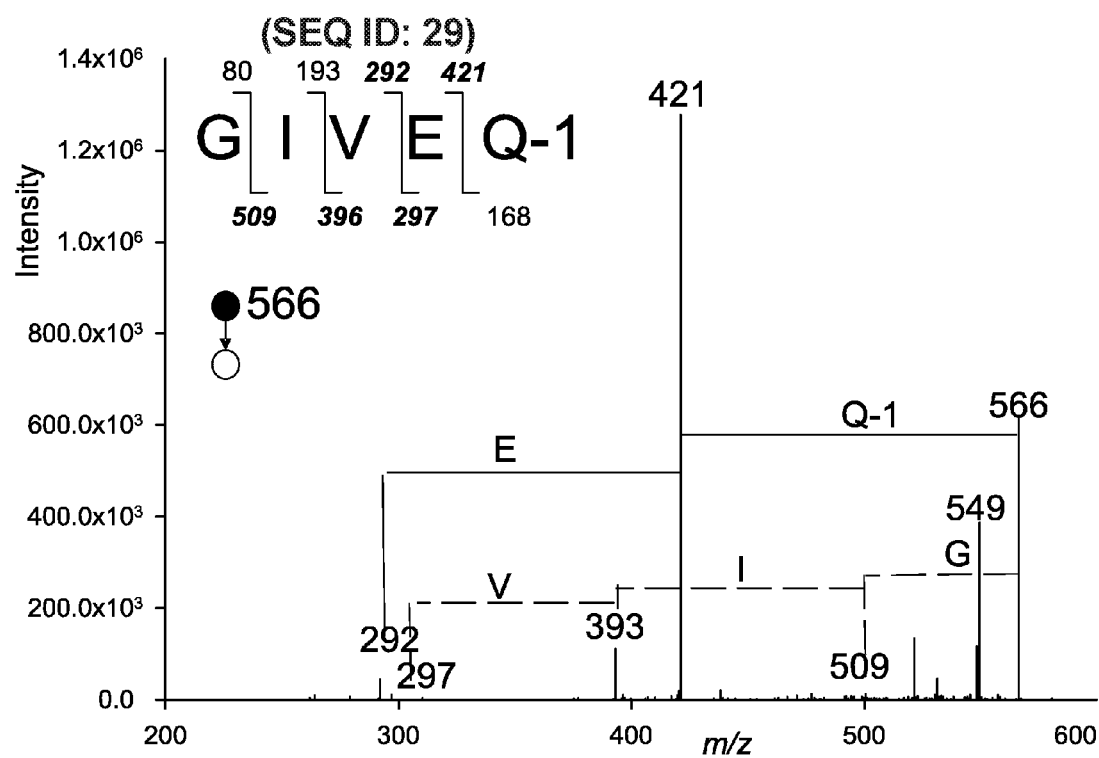
Figure 23A:
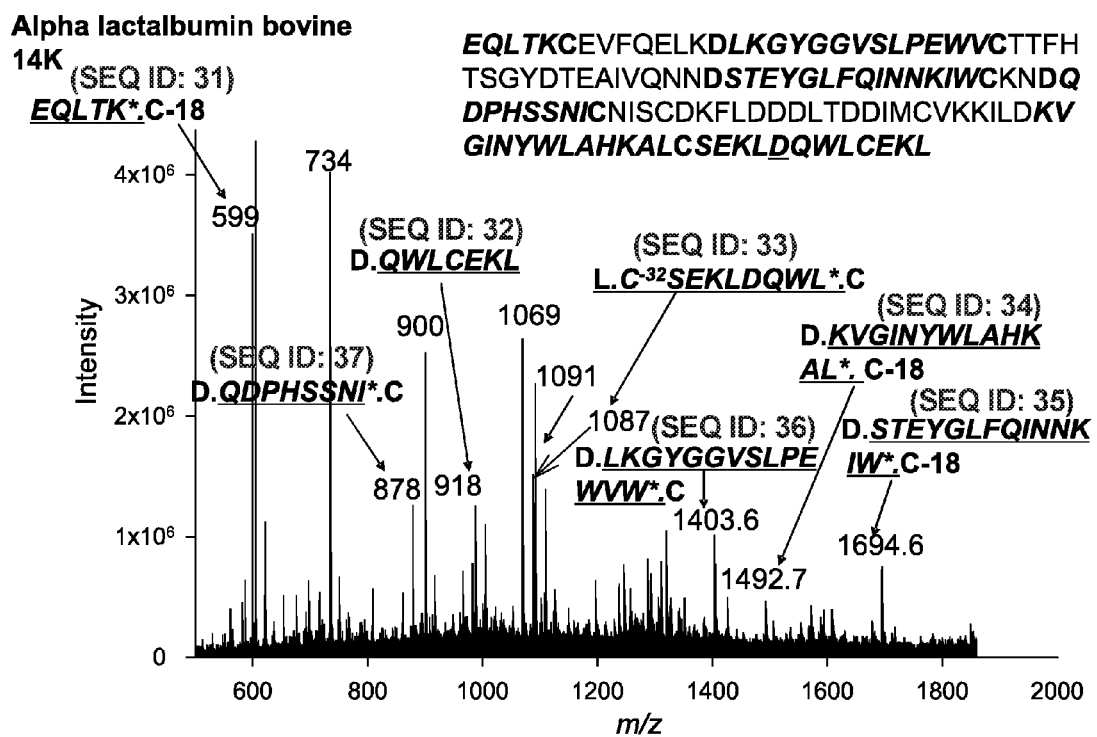
FIGS. 23A-F show the ESI full scan of protein α-lactalbumin (bovine milk) after pyrolysis and the MS/MS spectra.
Figure 23B:
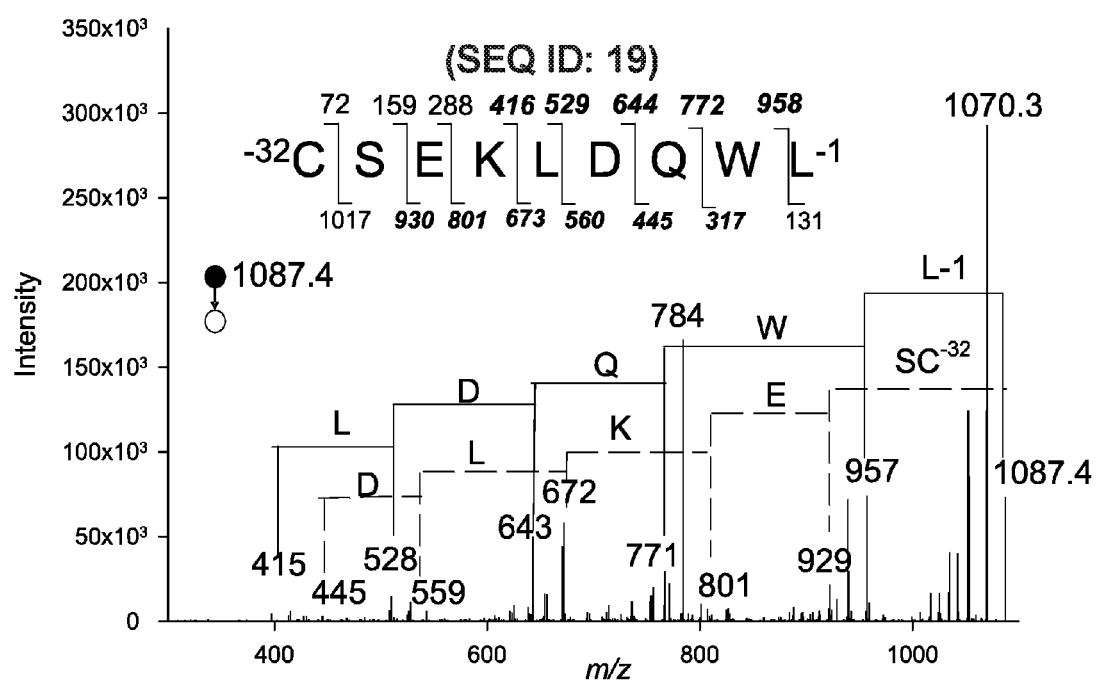
Figure 23C:
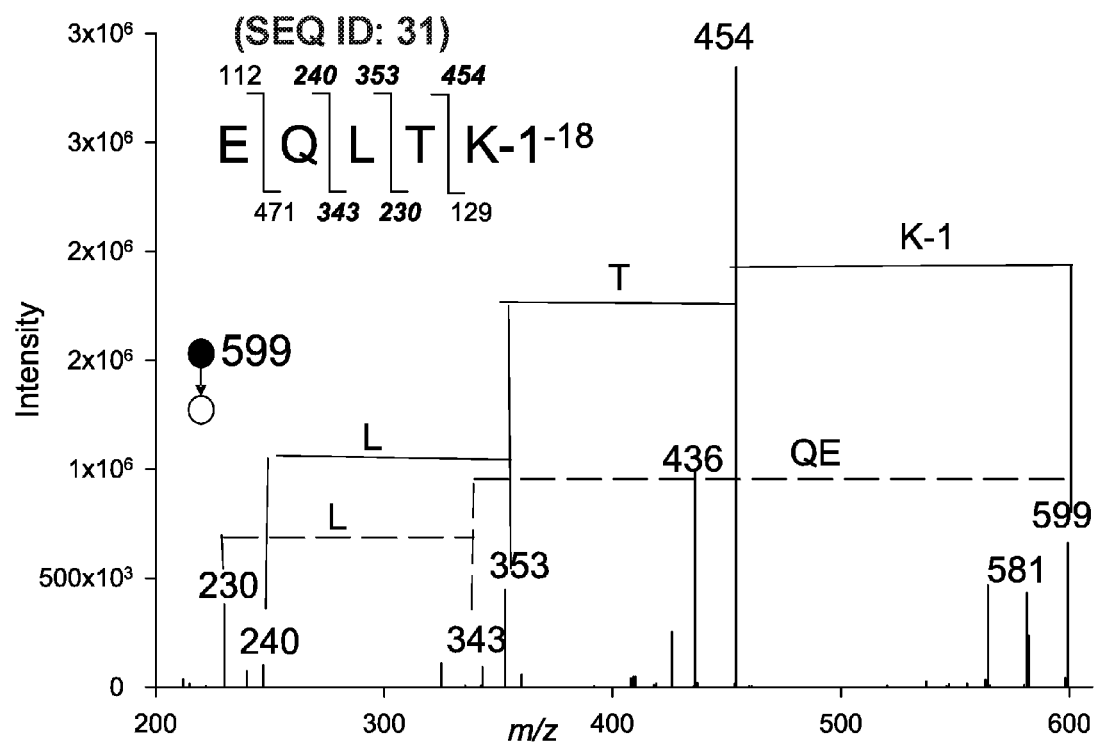
Figure 23D:
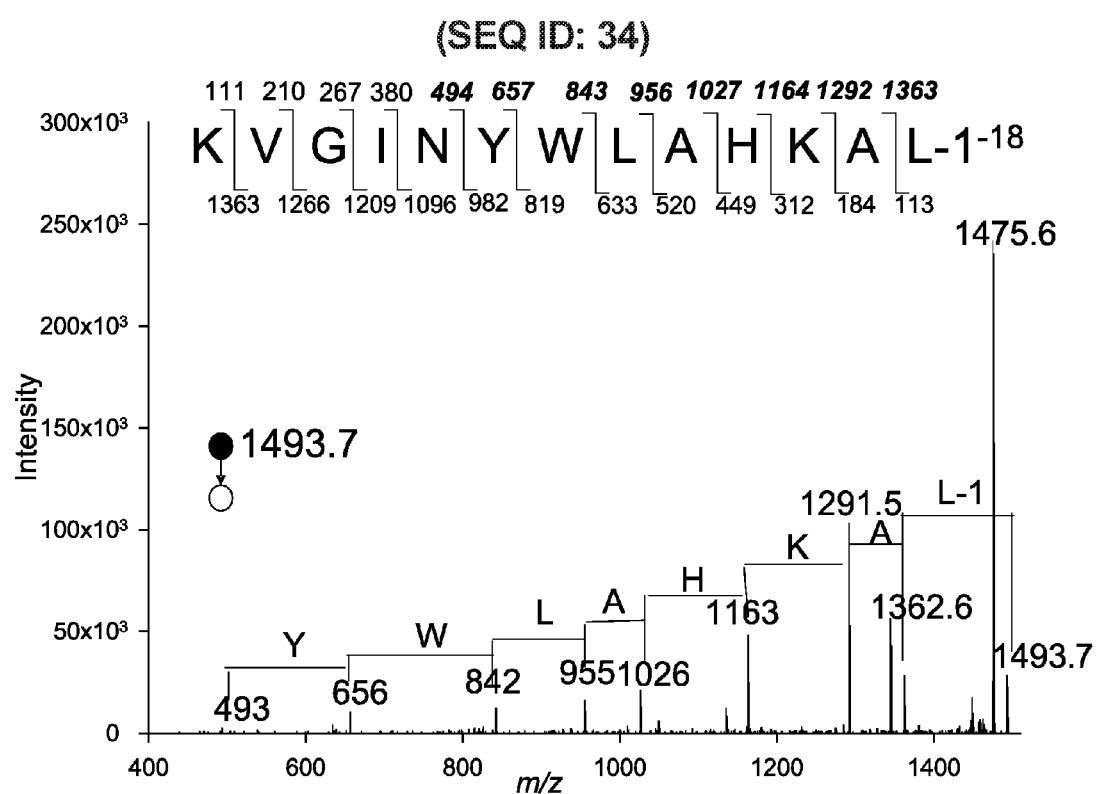
Figure 23E:
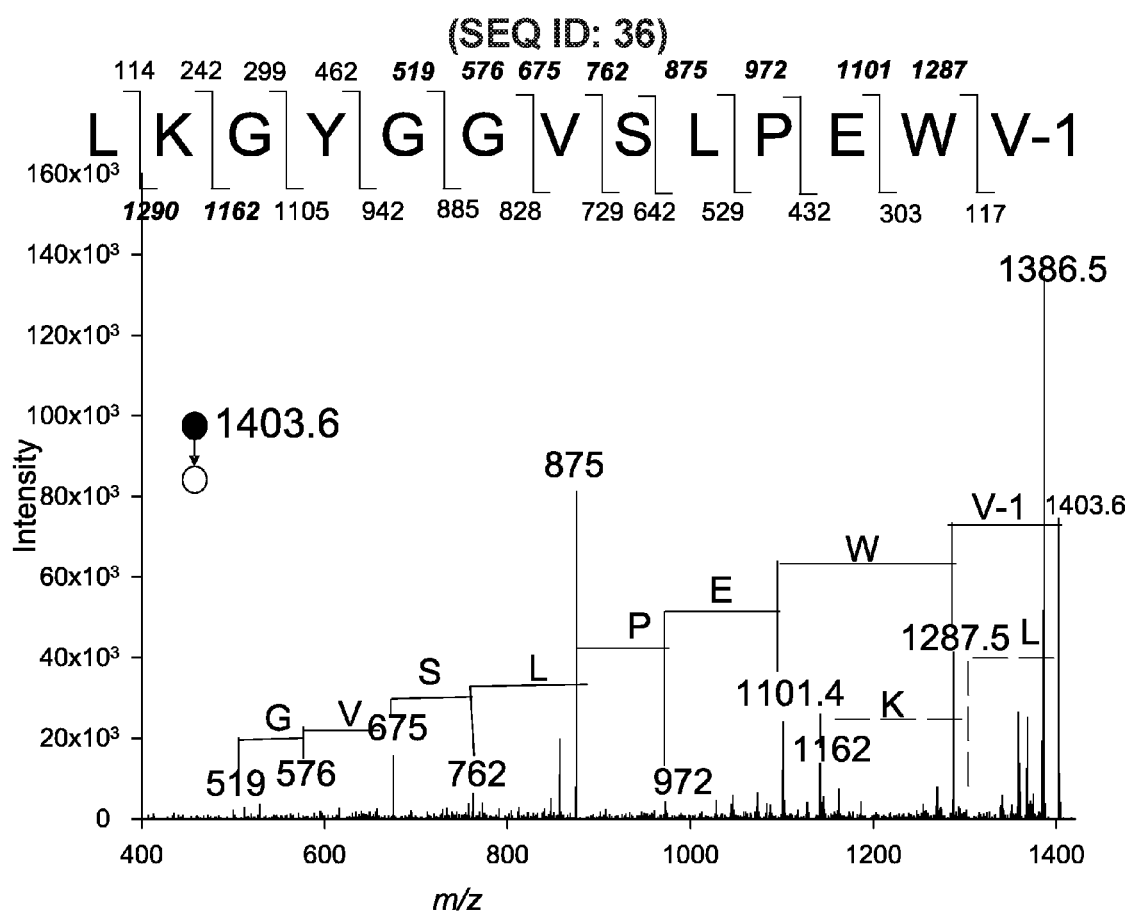
Figure 23F:
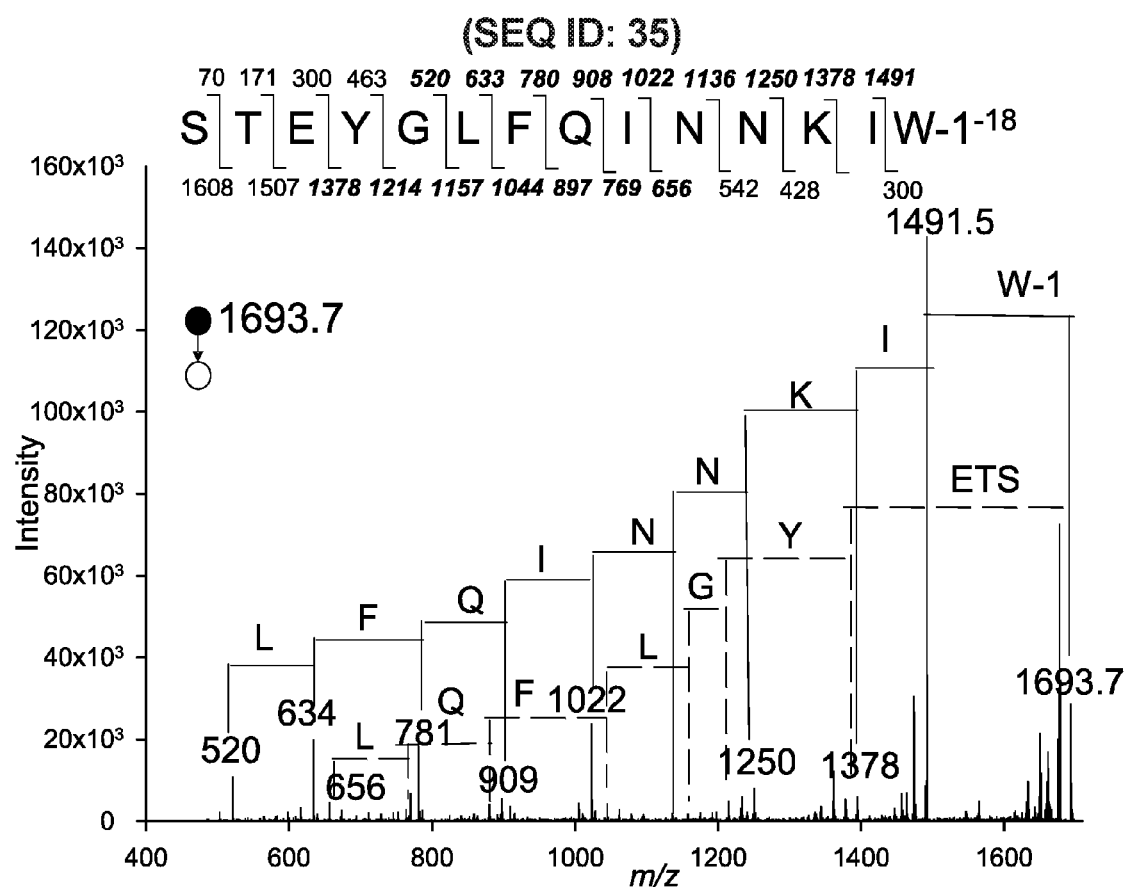

FIGS. 21A-C show the ESI full scan mass spectrum of the protein insulin after pyrolysis and the MS/MS mass spectra of m/z 566 and 778, the sodiated C-cleavage products confirm the sequences of both fragments analyzed. The sequence coverage for pyrolysis DC cleavage of insulin is 25.5%. Also, the first disulfide bonds connecting the two chains and the intra-chain A disulfide bond are broken. However the C-terminal side peptide.

The MS/MS data of ions at m/z 778 and 566 were manually extracted into a "*.dta" format file. For the sodiated ions, the value of 22 was subtracted to the precursor ion's mass and each of the fragmentation ions' to change them to protonated ions, but keep the intensity unchanged. FIG. 22 shows the Mascot search result of insulin using the MS/MS data of ions at m/z 778 and 566, showing the protein insulin is successfully identified, and both of the two fragment peptides are detected.

Sequest searching was also performed on this protein; however it was not successfully identified. Probable reason is that Sequest has problem dealing with small peptides, just as the ion m/z 605 is not identified to be part of lysozyme.

FIGS. 23A-F show the ESI full scan of protein α-lactalbumin (bovine milk) after pyrolysis and the MS/MS spectra. The sequence coverage is up to 60.2%. MS/MS confirms their sequences.

The MS/MS data of prominent ions at m/z 1087, 599, 1493.7, 1403.6, 1693.7, 617, 852, 936, 1511, 1712.6 were manually extracted into dta format files, which were used for the Mascot search. The Mascot search result successfully identified the protein α-lactalbumin with a very high score of 130 (greater than 78 is significant), and 6 peptide fragments are detected. However, the very prominent peak at m/z 1087, corresponding to LC$^{32}$SEKLDQWL*C (SEQ ID NO. 19), is not detected by the software, again due to limitations in setting up an in silico "enzyme" that accounts for the −32 modification of the N-terminal side peptide fragment in the free web-based version of Mascot.

Sequest result searched against the bovine database showed the successful identification of the protein α-lactalbumin. Again, the very prominent peak at m/z 1087, is not identified by the Sequest, due to the lack of proper accounting of chemical modifications by the data base search. However, the Sequest search against the whole database did not result in the identification of the protein. Careful inspection shows the peptides in the protein list are not generated according to the DC cleavage rule, which may be attributed to not being able to create the desired in-silico pyrolyutic "enzyme" in Sequest (namely, cleavage at before C and after D at the same time). Hence, it is expected that a better search outcome will result if using an appropriate in silicol pyrolytic enzyme.

Figure 24A:
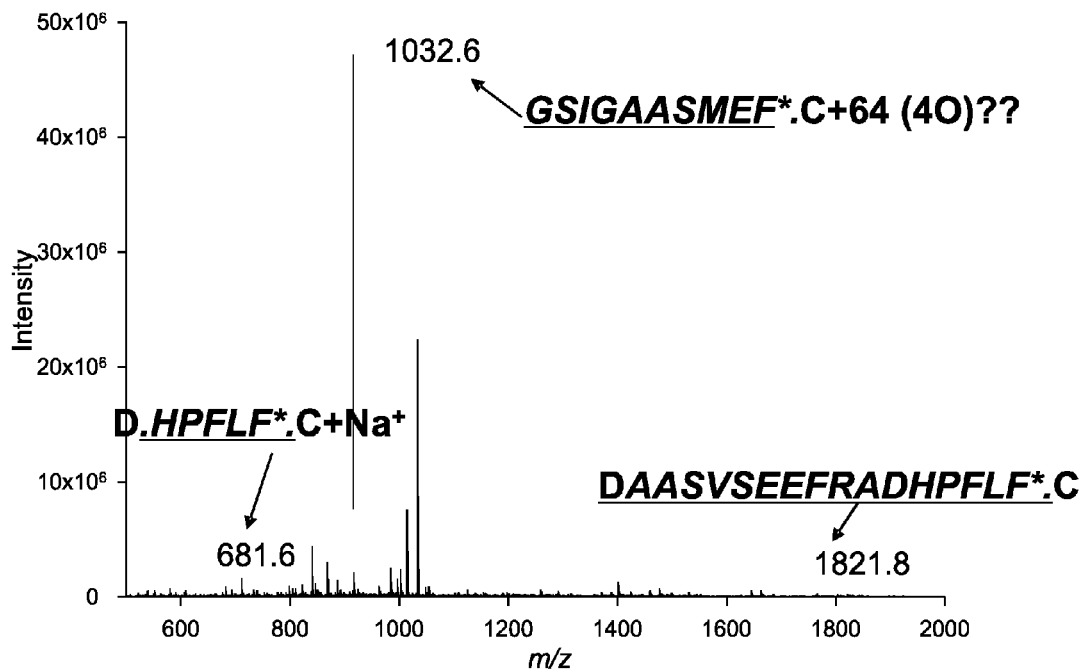
FIGS. 24 (A)-(C) show the ESI full scan mass spectrum of the protein albumin (chicken) after pyrolysis and the corresponding MS/MS mass spectra.
Figure 24B:
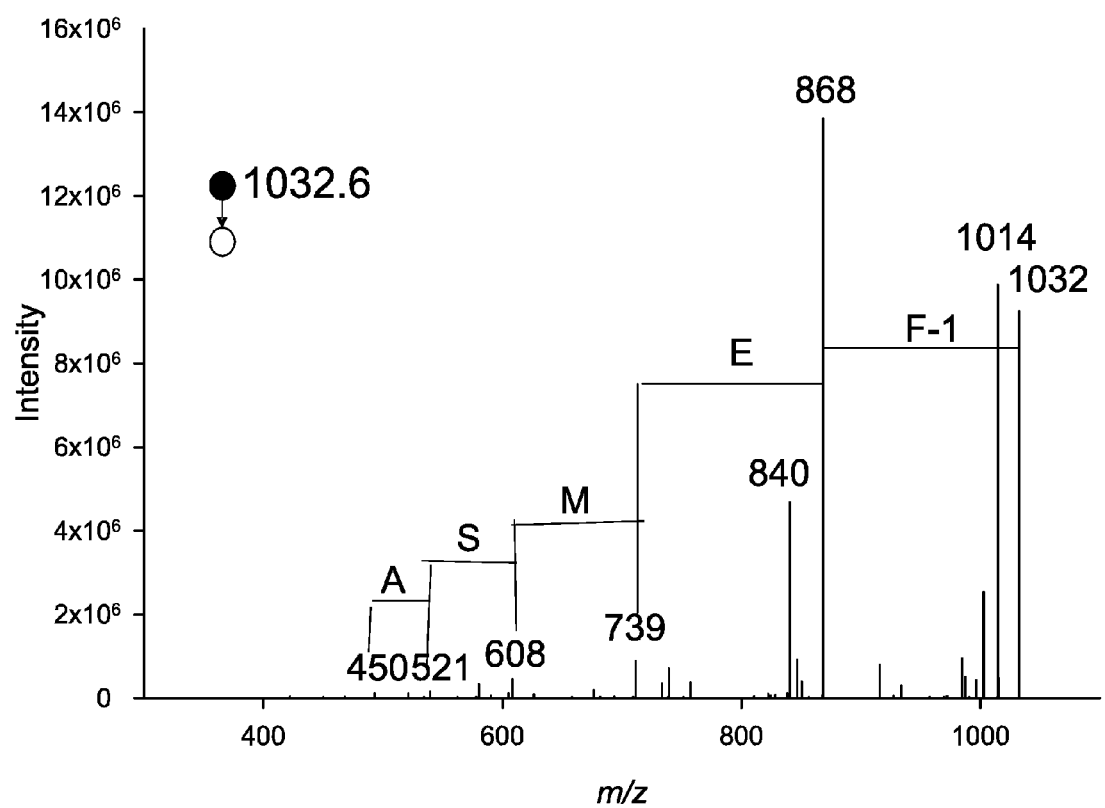
Figure 24C:
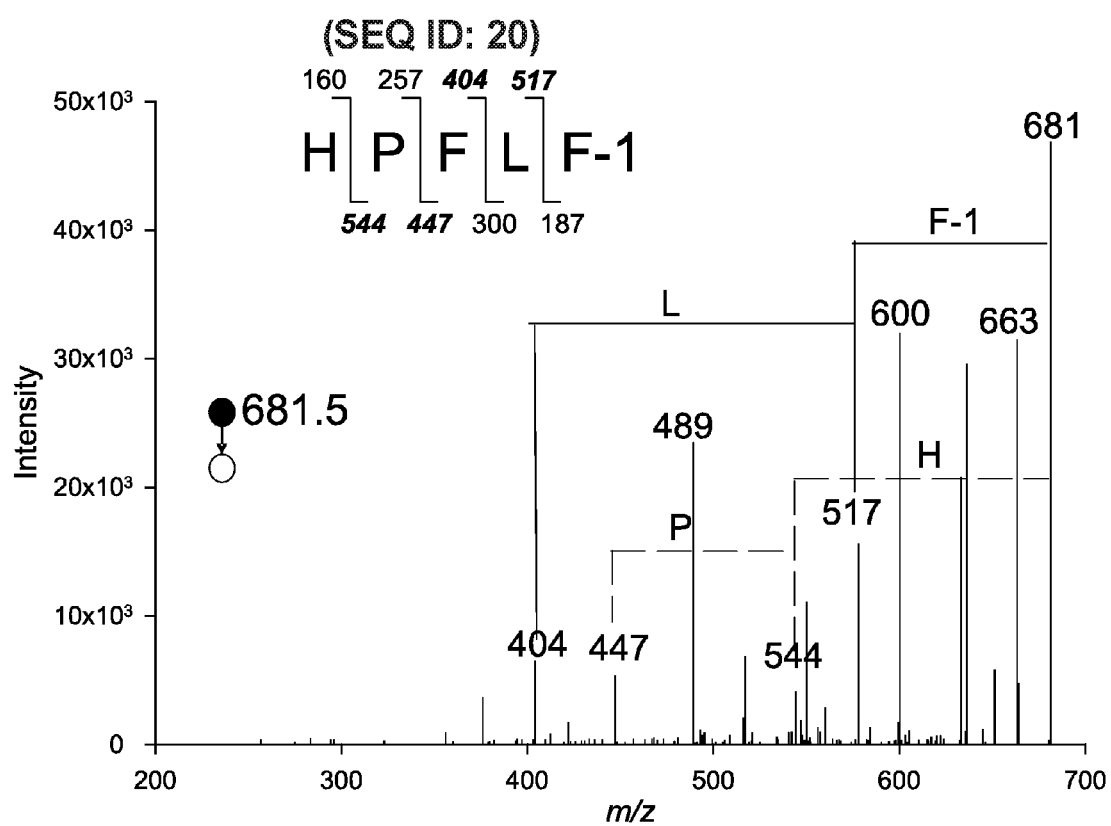

FIG. 24 shows the ESI full scan mass spectrum of the protein albumin (chicken) after pyrolysis and the corresponding MS/MS mass spectra. The peaks at m/z 681 and 1821.7 correspond to the cleavage products at D.C. corresponding to the sodiated DHPFLF*C (SEQ ID NO. 20) and protonated D AASVSEEFRADHPFLF*C (SEQ ID NO. 21), and their sequences are confirmed by MS/MS analysis. However, MS/MS data of the strongest peak at m/z 1032.6 seems to indicate to the cleavage product of sequence G SIGAASMEF*C (SEQ ID NO. 22), however, with a mass modification of +64. the MS/MS data show the b-ion series in the CID< but the y-ion series is not. Further investigation is needed to illustrate its structure.

Mascot analysis of the MS-data was unable to identify this protein. The unknown +64 modification of the peptide is partly suspected to cause this uncertainty. Subsequent Sequest search against the chicken database accounting for the variable modification of −18 at the C-terminus of peptides shows albumin chicken is identified. However, Sequest search against the entire database did not show the identification of albumin chicken.

Figure 25A:
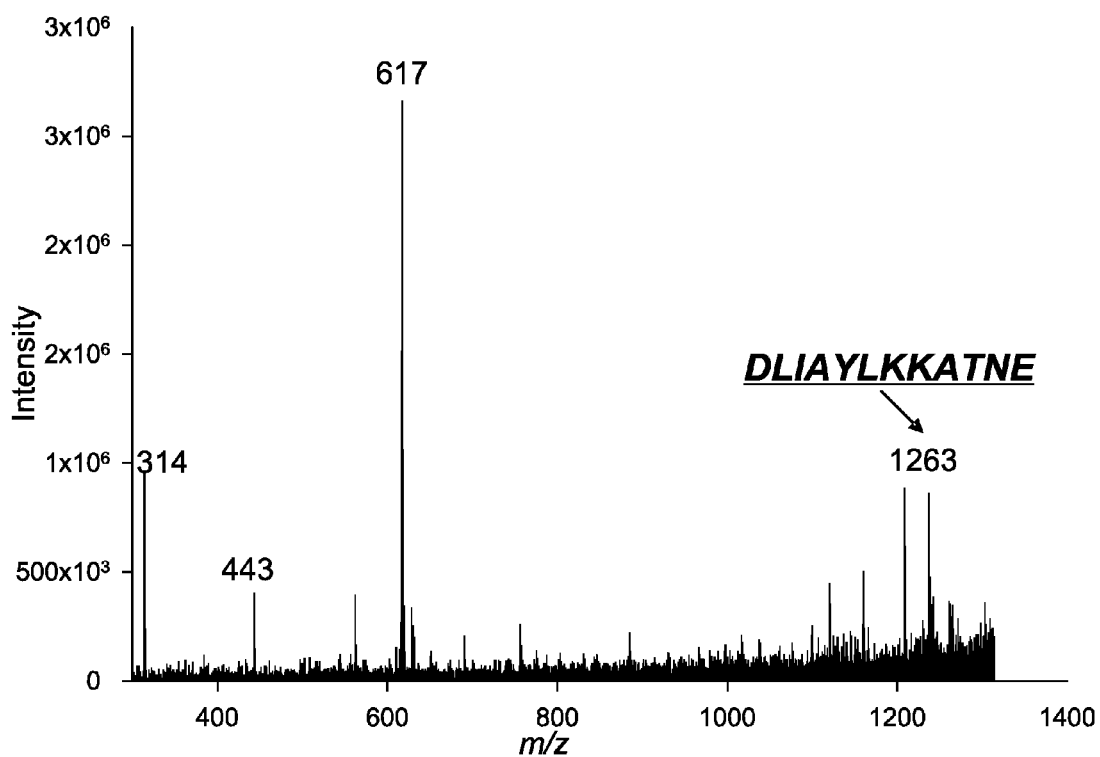
FIG. 25(A) shows the ESI full scan mass spectrum of the protein cytochrome C (horse heart) after pyrolysis and FIG. 25 (B) shows the corresponding MS/MS mass spectra.
Figure 25B:
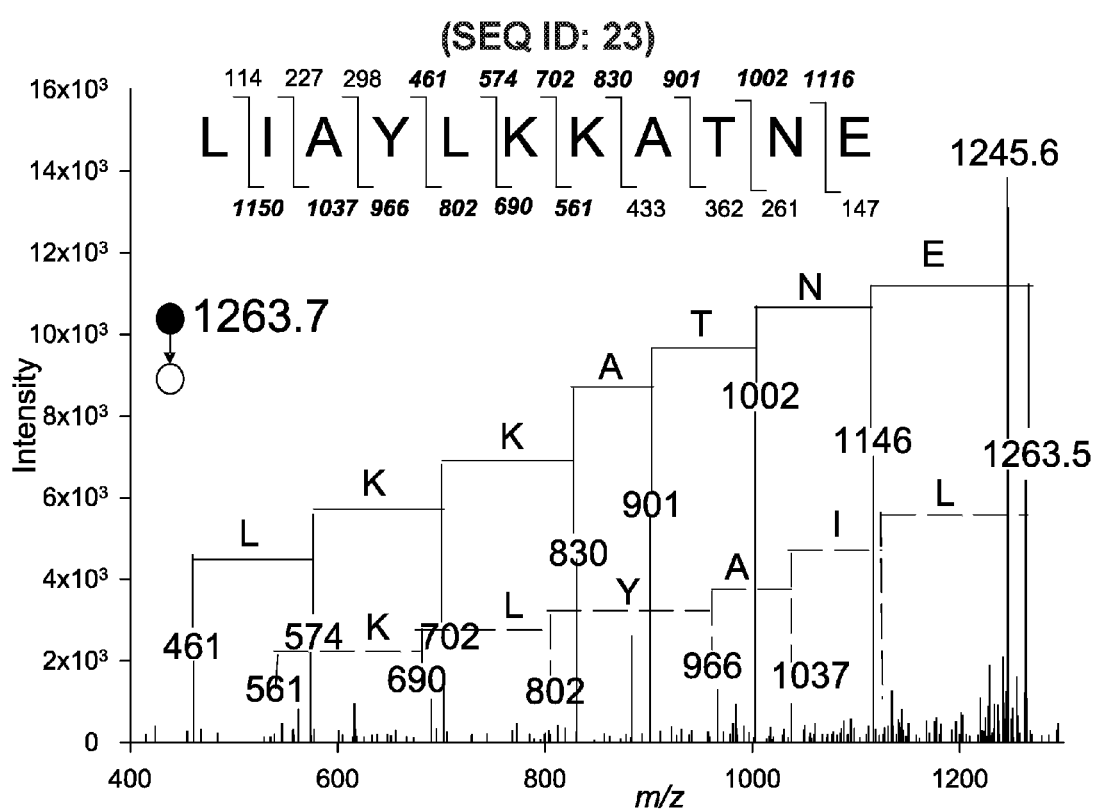

The same experiment was conducted on the protein cytochrome C (horse heart). The only pyrolysis D, C cleavage product observed is an ion at m/z 1263, corresponding to the peptide of sequence DLIAYLKKATNE (SEQ ID NO. 23) (FIG. 25). the dta file of ion m/z 1263 is applied for Mascot search shown in FIG. 26. It shows the peptide fragment is a sequence tag and cytochrome C is identified. Also, Sequest search against the entire database shows the identification of cytochrome C by identifying the sequence tag.

In summary, at this point, results presented demonstrated that pyrolysis for 10 seconds and up to 220° C. induces peptides and proteins to cleave site-specifically at the N-terminus of C and at the C-terminus of D. Moreover, sequence information of the original protein is retained after the pyrolysis process and the sequence tags can be detected by MS/MS. In addition, the MS/MS data can be used for successful database search (Mascot and Sequest) to identify the protein. However, limited success in protein identification has been achieved by this method since we are unable to design the appropriate pyrolytic in silico "enzyme" and accounting for the proper chemical modifications. Finally, some of the expected DC cleavage peptides are not observed in the ESI analysis. Considering that some of these peptides might be suppressed due to the ionization suppression effects commonly present in ESI of complex mixtures, an HPLC separation is coupled online prior to the MS analysis to investigate this possibility.

Example 7

HPLC-MS Analysis of Pyrolyzed Proteins and Database Search

To minimize the ion suppression effect in ESI, pyrolyzed proteins were subjected to online HPLC separation prior to ESI-MS analysis. The software will automatically perform a full-scan mass spectrum followed by three data dependent product ion mass-spectral scans of the most intense precursor ions (a.k.a., "big-three" scan).

Figure 27:
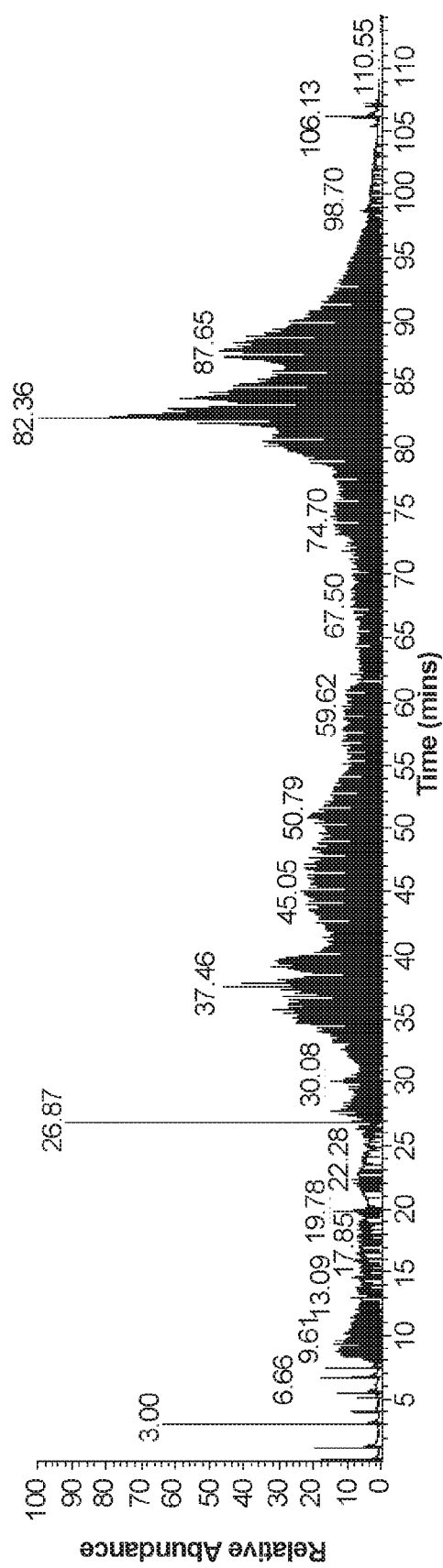
FIG. 27 shows the chromatogram and the Sequest search result of pyrolyzed lysozyme.

FIG. 27 shows the chromatogram and the Sequest search result of pyrolyzed lysozyme. The DC cleavage peptide fragments m/z 605, 828, 1327.6, 1435.6 (also observed in direct injection) were detected at time 15.6, 30.2, 35.7 and 39.4 min respectively (1201 not detected). The Sequest search against the chicken database shows lysozyme is identified and the identified peptides are produced following the DC cleavage rule. Still no more expected fragments are observed. Searching against the entire database did not yield the identity of lysozyme. Converting the RAW file into m/z data file, followed by a Mascot search also failed to give out the correct protein id. Because of the large quantity of the MS/MS data generated, it is not possible to manually extract them to a dta file for Mascot search.

In the case of the protein albumin (chicken), it is identified by Sequest search against the chicken database, but not against the entire database.

Figure 28A:
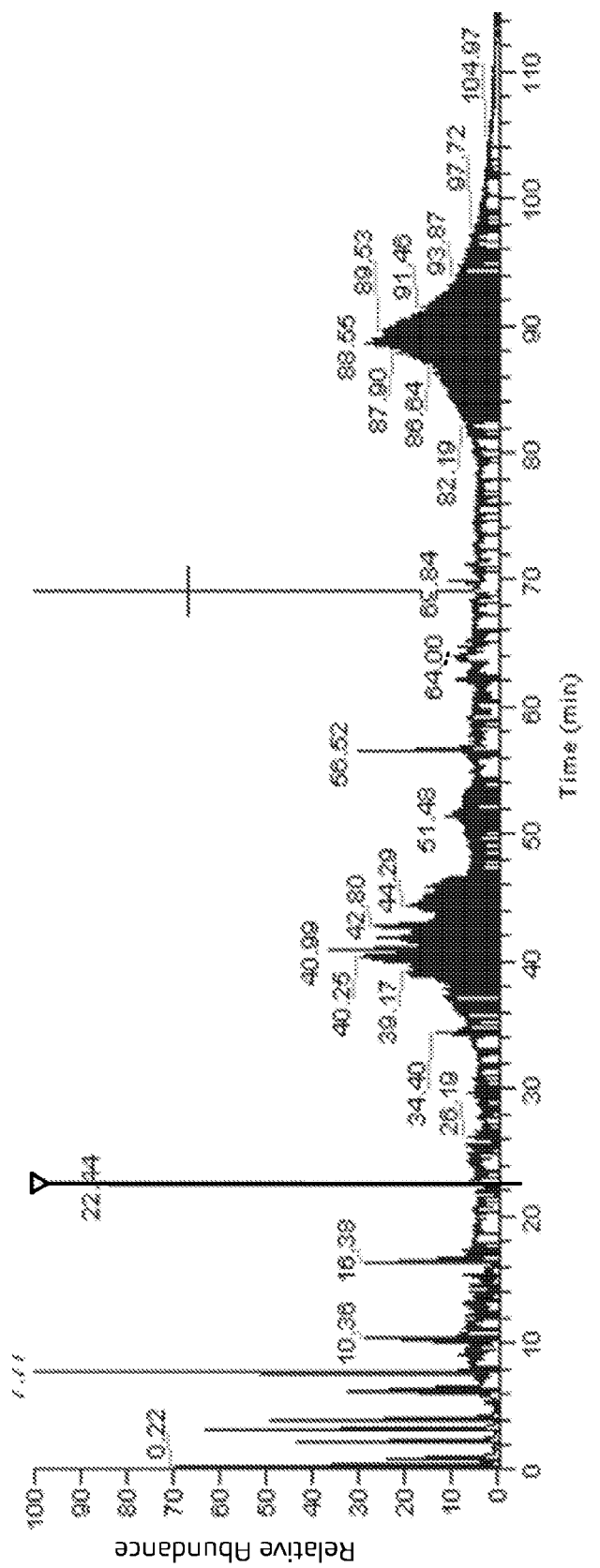
FIGS. 28 (A)-(C) show chromatograph (A) and full MS scans (B)-(C) at time 22.58 min and 39.17 min for protein alactalbumin.
Figure 28B:
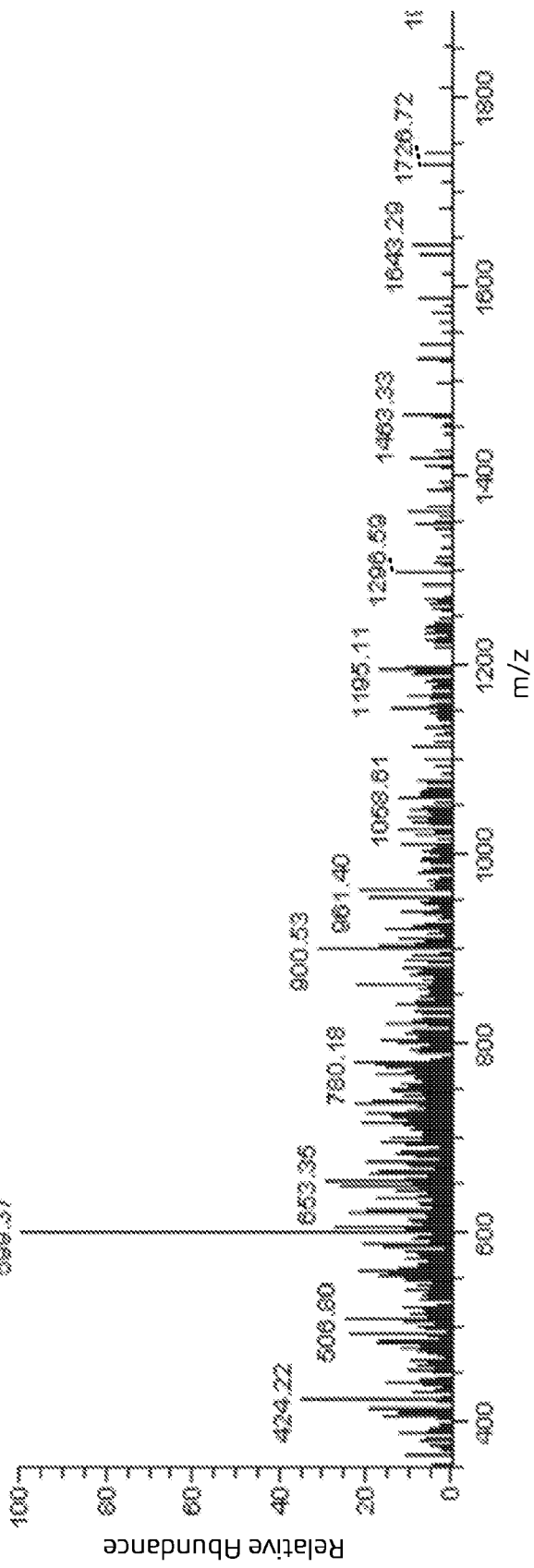
Figure 28C:
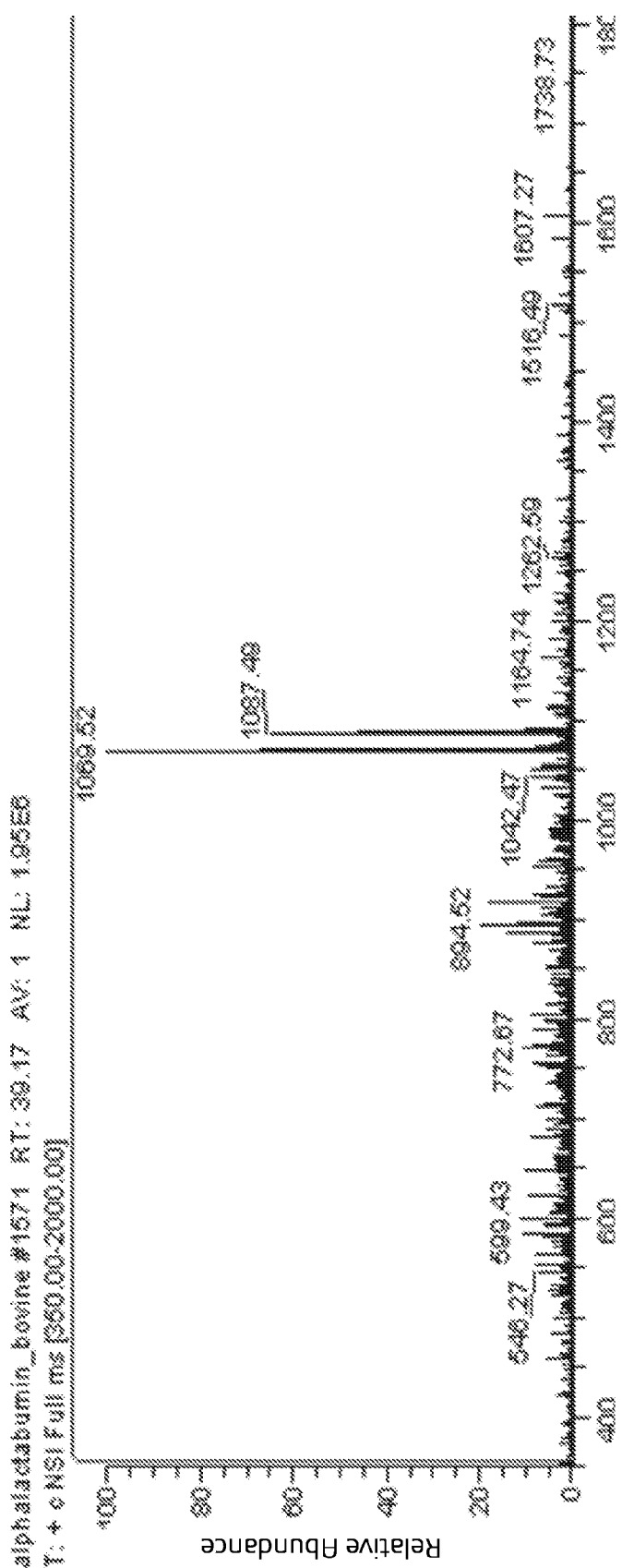

The same HPLC-MS experiment was conduct to protein alactalbumin. FIG. 28 illustrates its chromatograph and full MS scans at time 22.58 min and 39.17 min showing the peptides eluting out of column. However, the Sequest search did not yield its identity.

To sum up, HPLC separation prior to ESI analysis does not seem to help identify more expected peptide fragments as anticipated. It seems that the limiting factor in the analysis is the inability of the Sequest search engine, as mentioned before, to design the pyrolytic in silico enzyme with the appropriate cleavage sites and chemical modifications.

Example 8

Application to Bacterial Identification

At this point, it is demonstrated that pyrolysis can used as a protein digestion method to identify proteins by database search. In this section, this methodology is extended to the identification of bacteria via bottom-up proteomics using pyrolysis as the "enzyme".

FIG. 29 shows the full ESI mass spectrum scan of pyrolyzed samples of *E. coli* and *S. Aureus* via direct infusion ESI-MS. FIG. 30 shows the on-probe DESI-MS (on-probe DESI is presented in detail in Chapter 3) full scan of pyrolyzed bacteria whole cells *Salmonella typhimutium*, and *Pseudomonas aureginosa*. The full scans of these bacteria show there are no prominent peaks of peptides detected, majorly because of the ion suppression effect and high complexity of the sample produced (after whole cells were pyrolyzed). To circumvent this limitation, HPLC separation prior to ESI analysis was conducted on these samples.

Figure 31A:
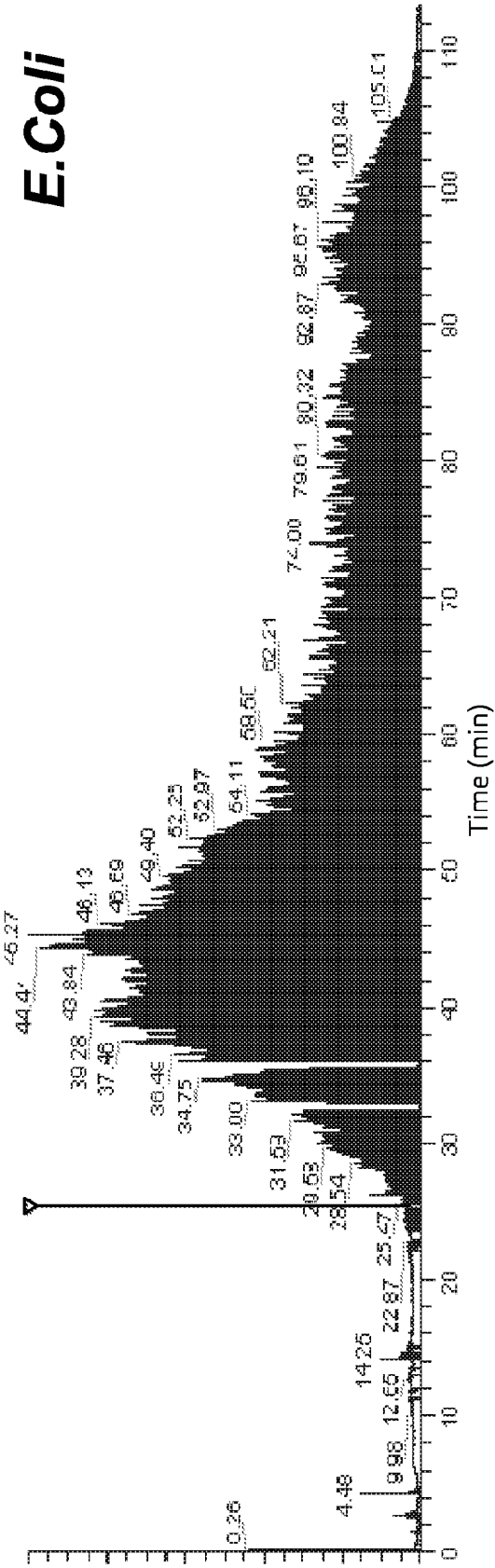
FIGS. 31 (A)-(C) show chromatograph (A) and full scan mass spectra for bacteria E. coli at retention time 25.34 min (B) and 25.85 min (C).
Figure 31B:
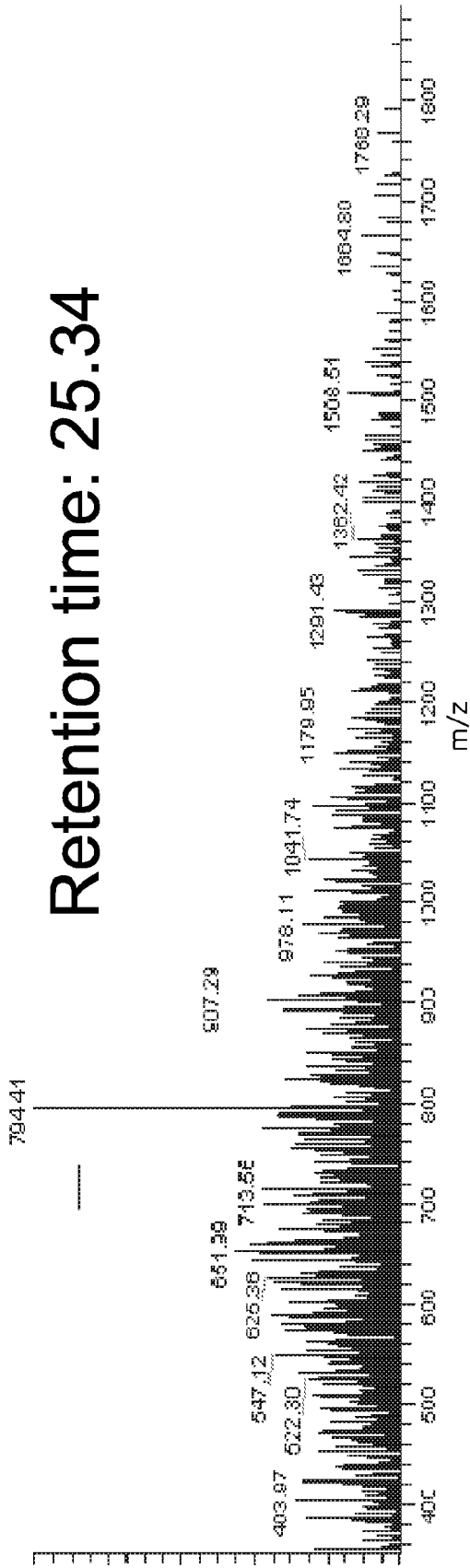
Figure 31C:
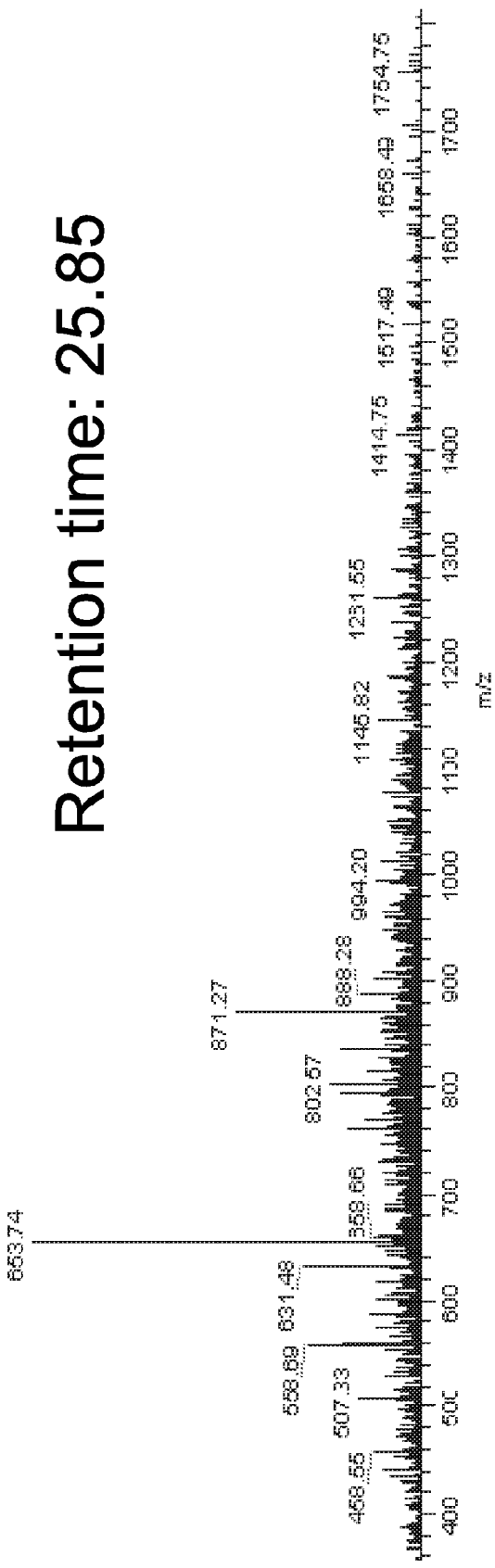

The HPLC-MS experiment was conducted on the bacteria *E. coli*. FIG. 31 illustrates its chromatogram and full scan mass spectra at retention time 25.34 min and 25.85 min as examples showing the peptides eluting out of column. Also good MS/MS data are obtained for each peptide eluting out of column at different times. The Sequest search in bacteria database (FIG. 31) did give out some of its possible protein origins being from *E. Coli*, however not with high ranks (the highest is #57). Upon further inspection, the peptides detected for all the proteins in the result list were not generated according to the DC cleavage rule (namely generated from cleavage before C and after D). Again, even though high S/N tandem mass spectra of peptides are obtained from the pyrolysis of intact bacteria, a capable search engine is still limiting factor to perform a successful database search for bacteria identification.

Figure 32A:
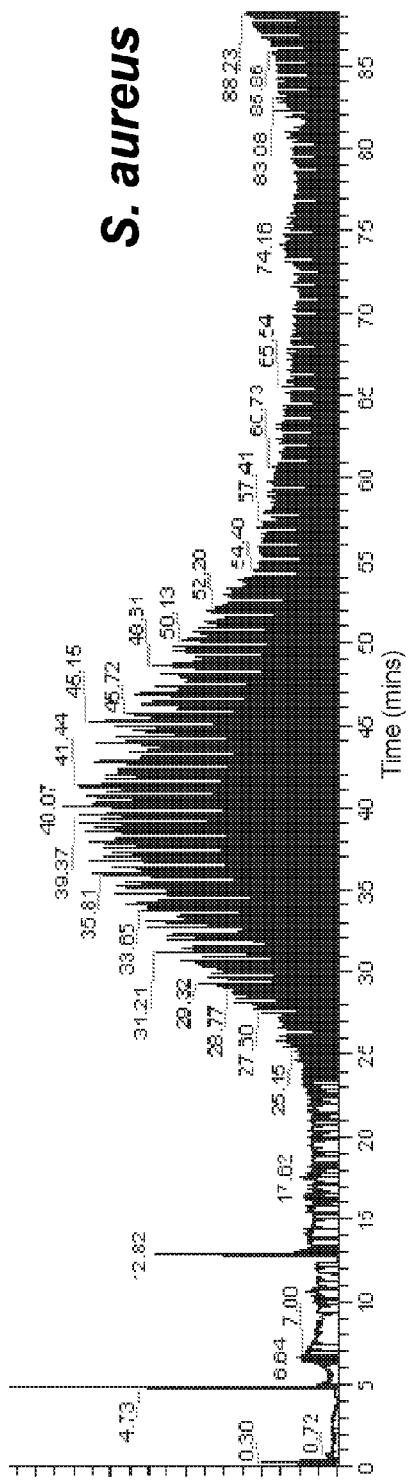
FIGS. 32 (A)-(C) show chromatograph (A) and full scan mass spectra for bacteria S. aureus at retention time 13.43 min (B) and 33.32 min (C).
Figure 32B:
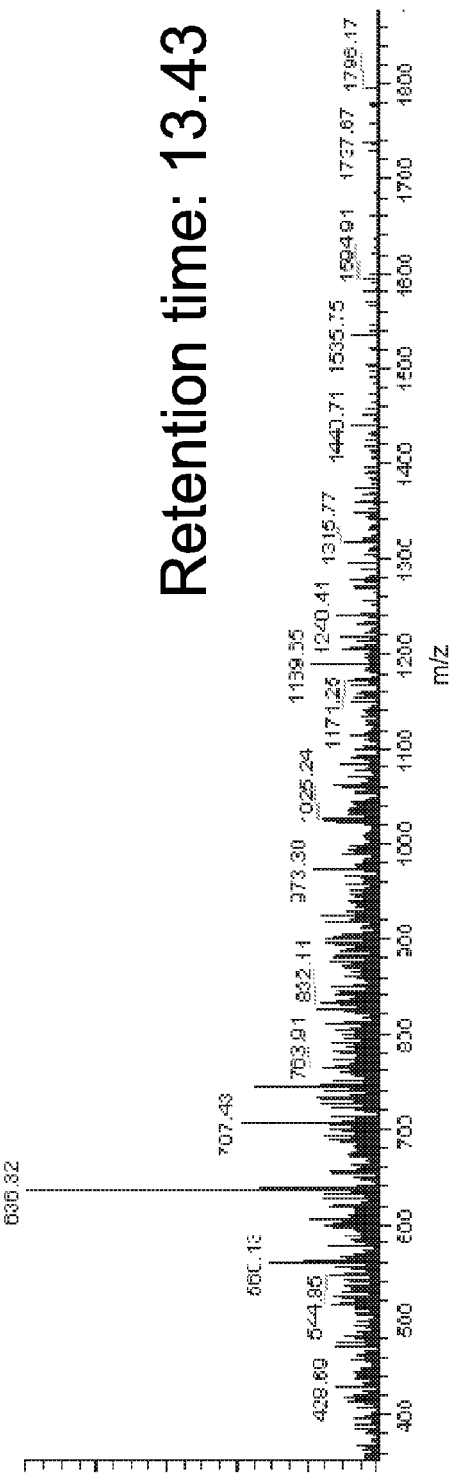
Figure 32C:
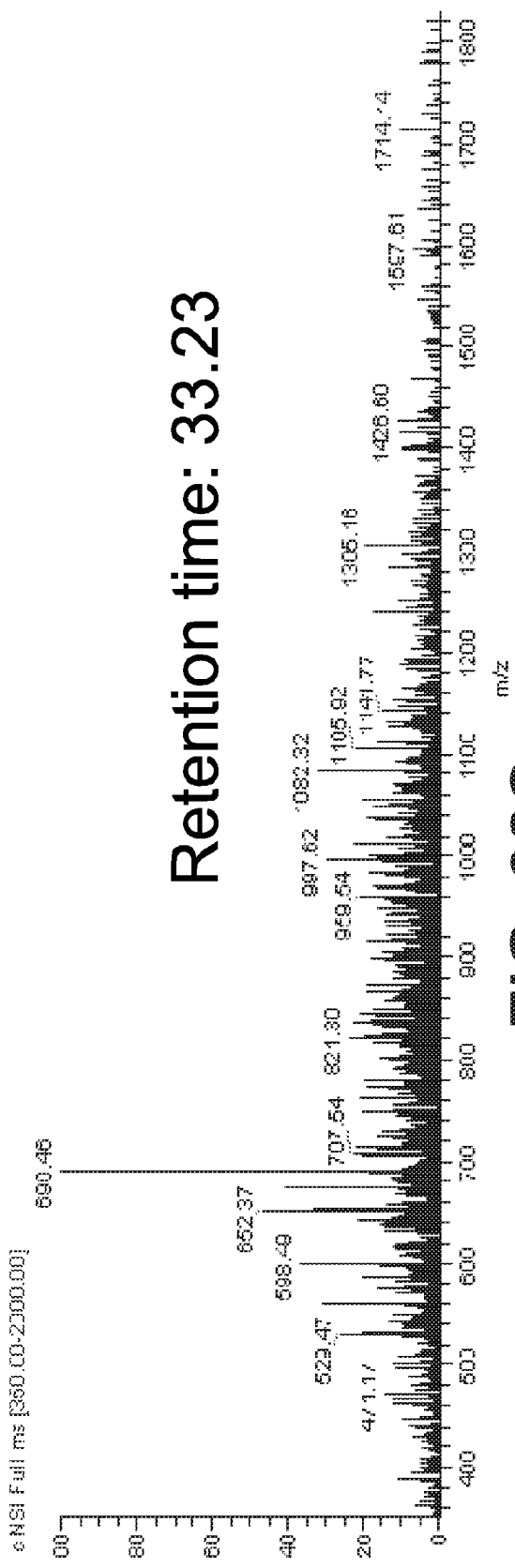
Figure 33:
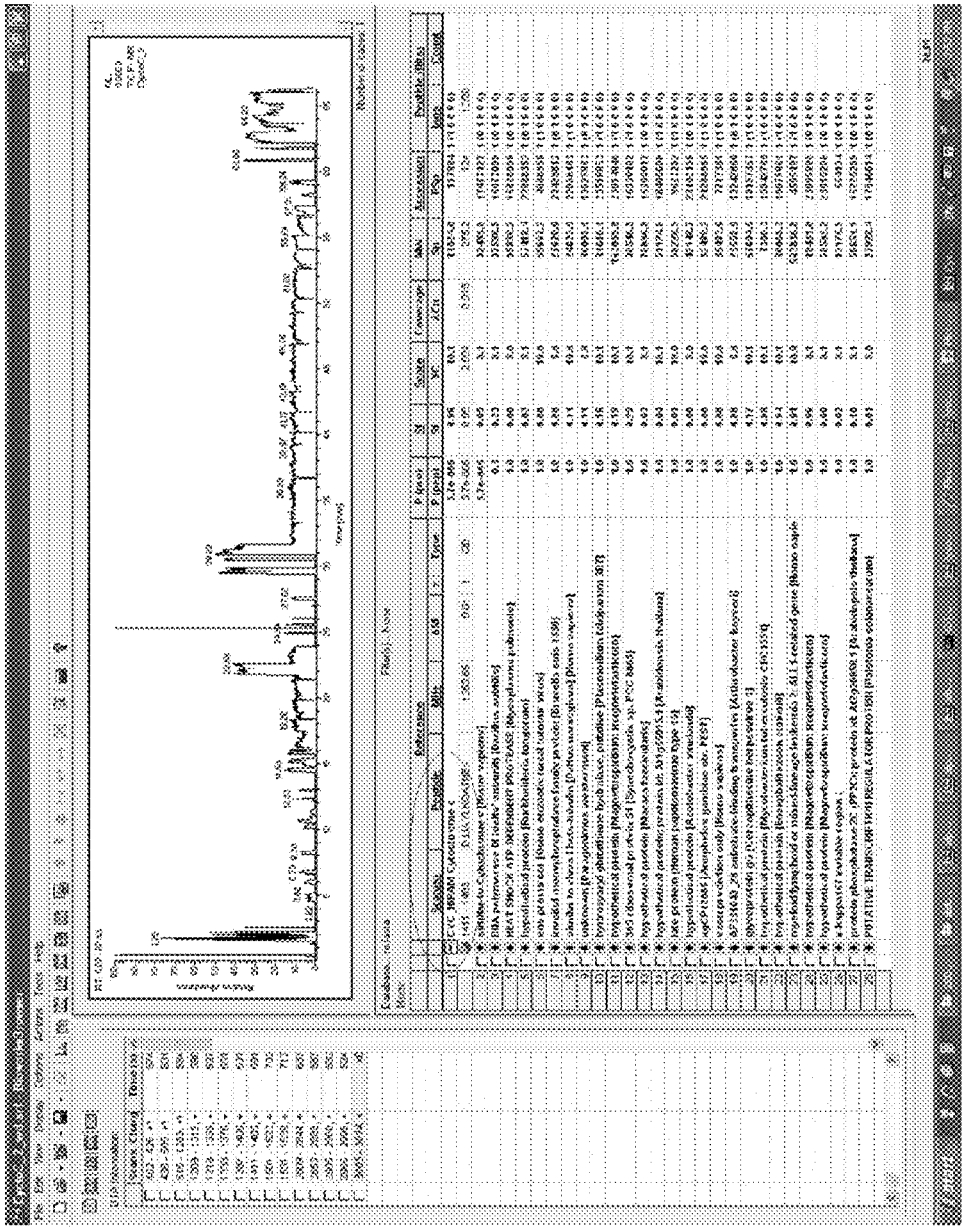
FIG. 33 shows an HPLC chromatogram of cytochrome c and a chart of Sequest results.
Figure 34:
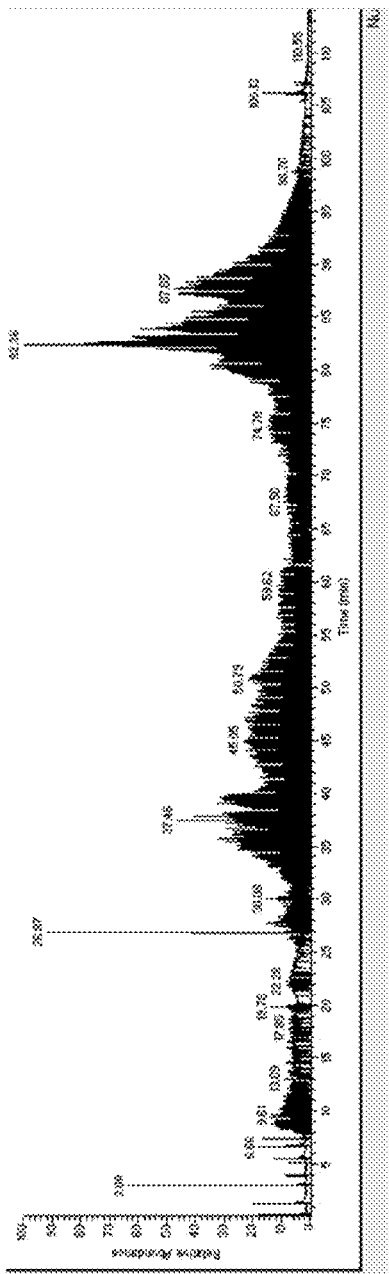
FIG. 34(A) is an HPLC chromatogram of pyrolyzed lysozyme and FIG. 34(B) is a chart of the Sequest search result gained via HPLC-MS.
Figure 34:
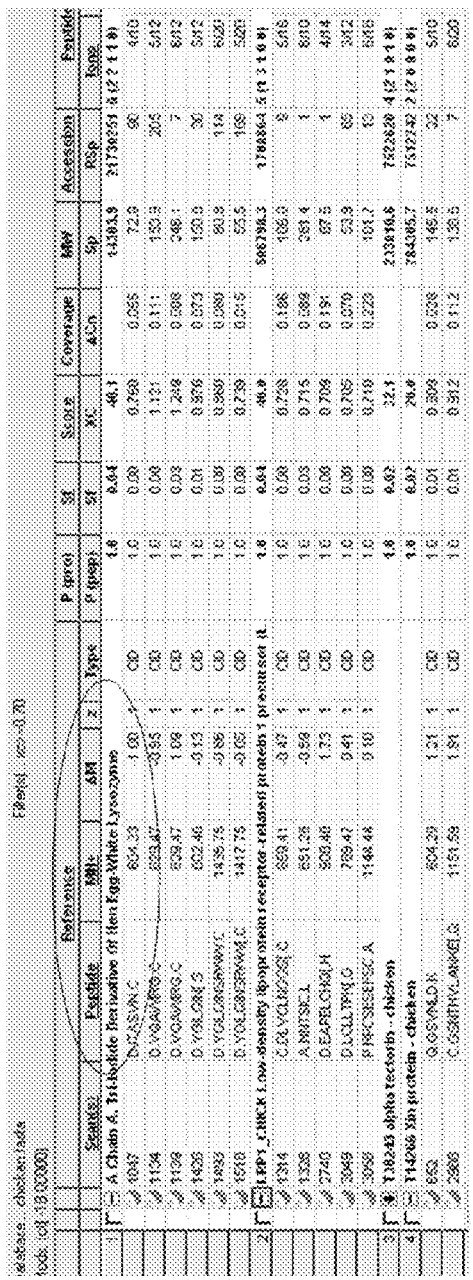
Figure 36:
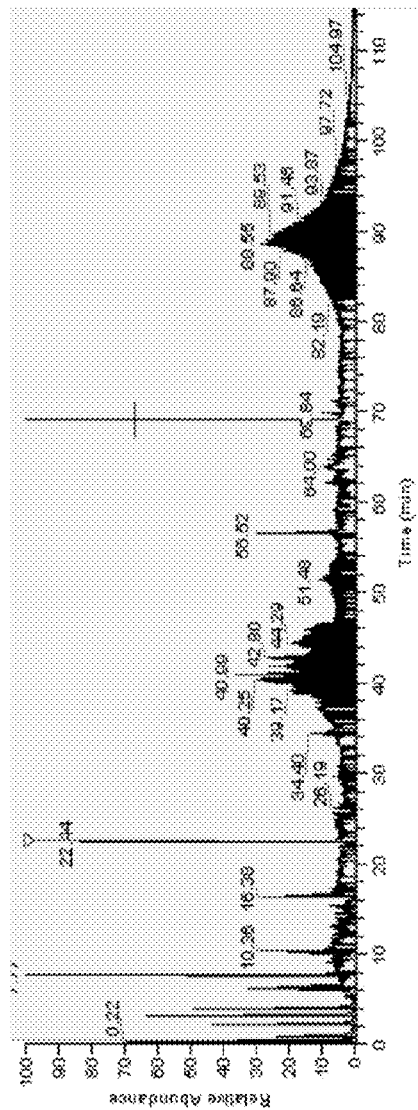
FIGS. 36(A) and (C) are HPLC chromatograms of alpha-lactalbumin and FIGS. 36(B) and 36(D) are charts of the full MS scans at time 22.58 min and 39.17 min respectively, showing the peptides eluting out of the column.
Figure 36:
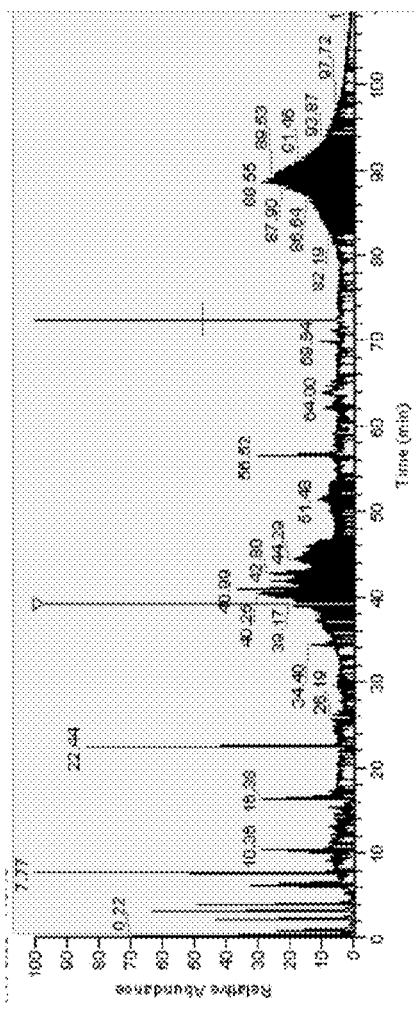
Figure 36:
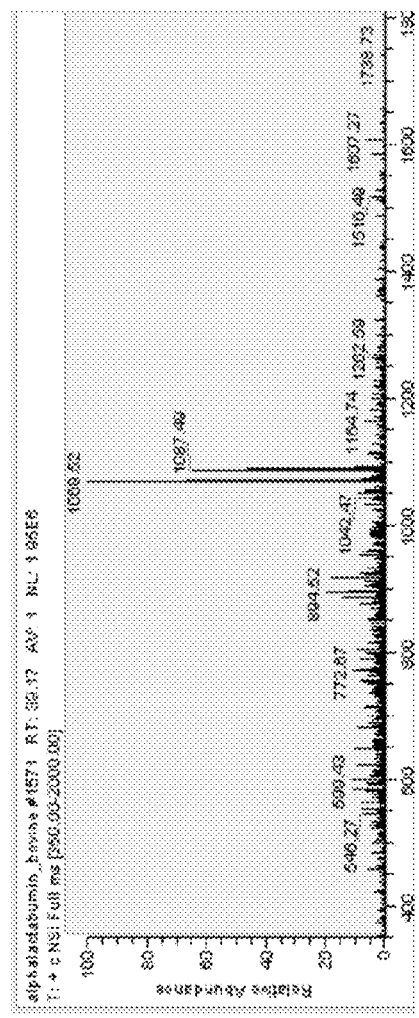
Figure 38:
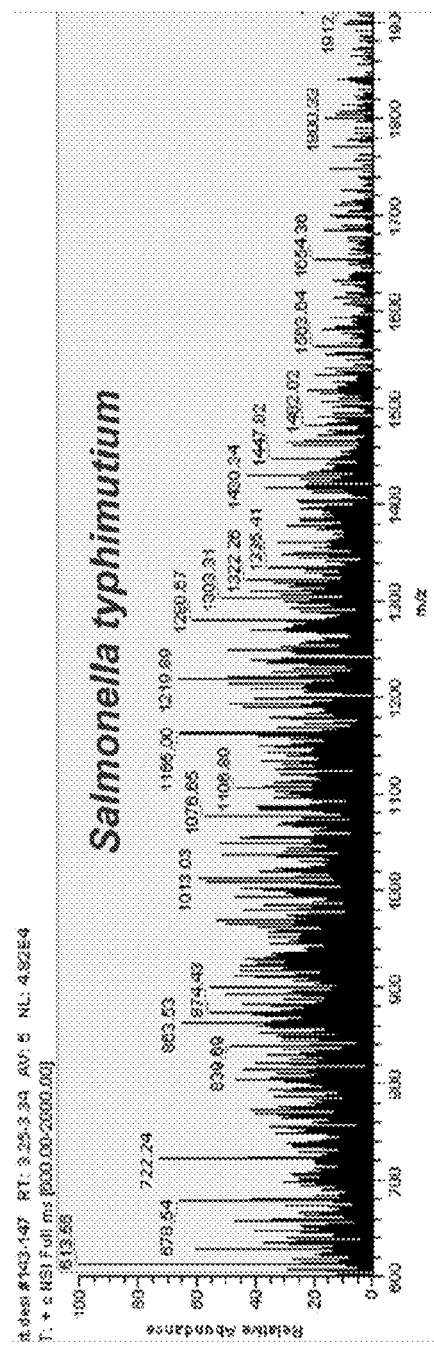
FIGS. 38(A) and 38(B) are charts of the on-probe DESI-MS full scan of pyrolyzed whole cells of S. typhimutium and P. aureginosa, respectively.
Figure 38:
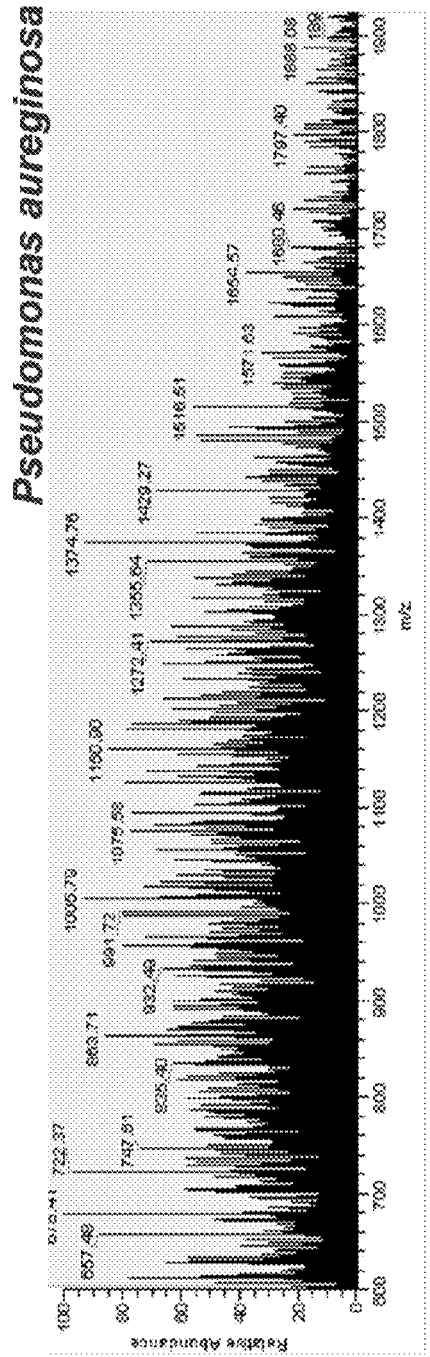
Figure 39:
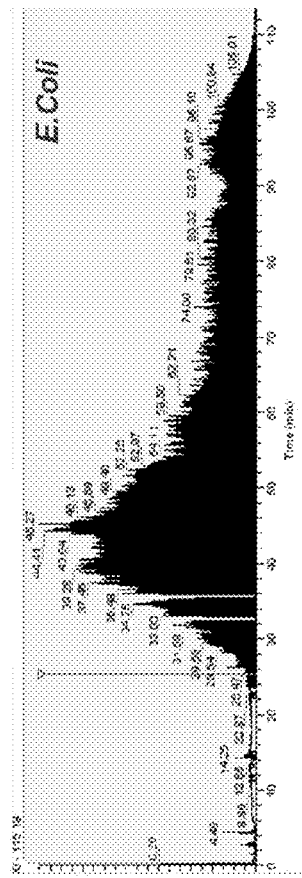
FIG. 39(A) is an HPLC chromatogram of pyrolyzed E. coli.
FIGS. 39(B) and 39(C) are charts of the full MS scans at 25.34 and 25.85, respectively.
FIG. 39(D) is a chart of the Sequest search in a bacteria database showing the one of its possible origins is E. coli.
Figure 39:
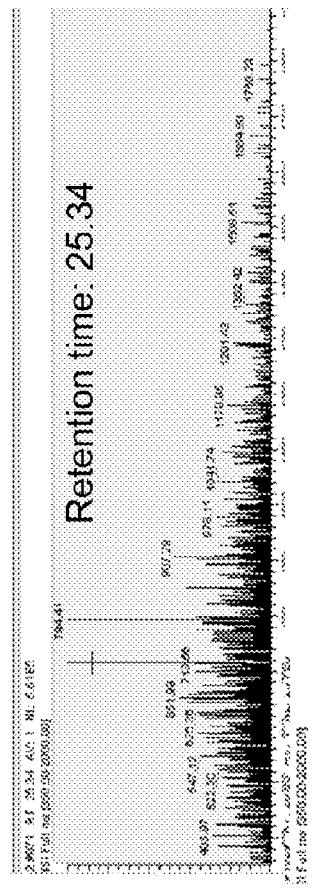
Figure 39:
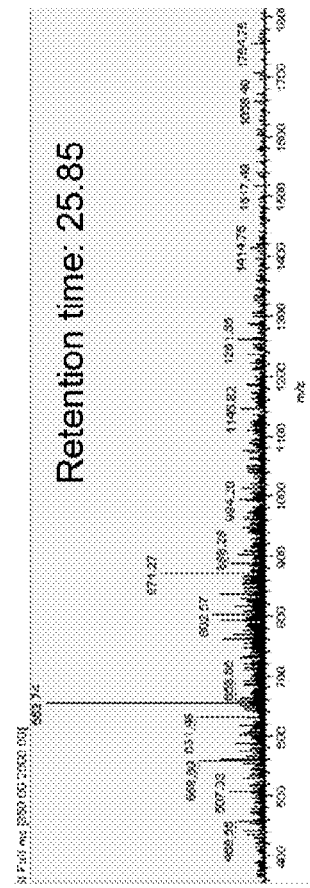
Figure 40:
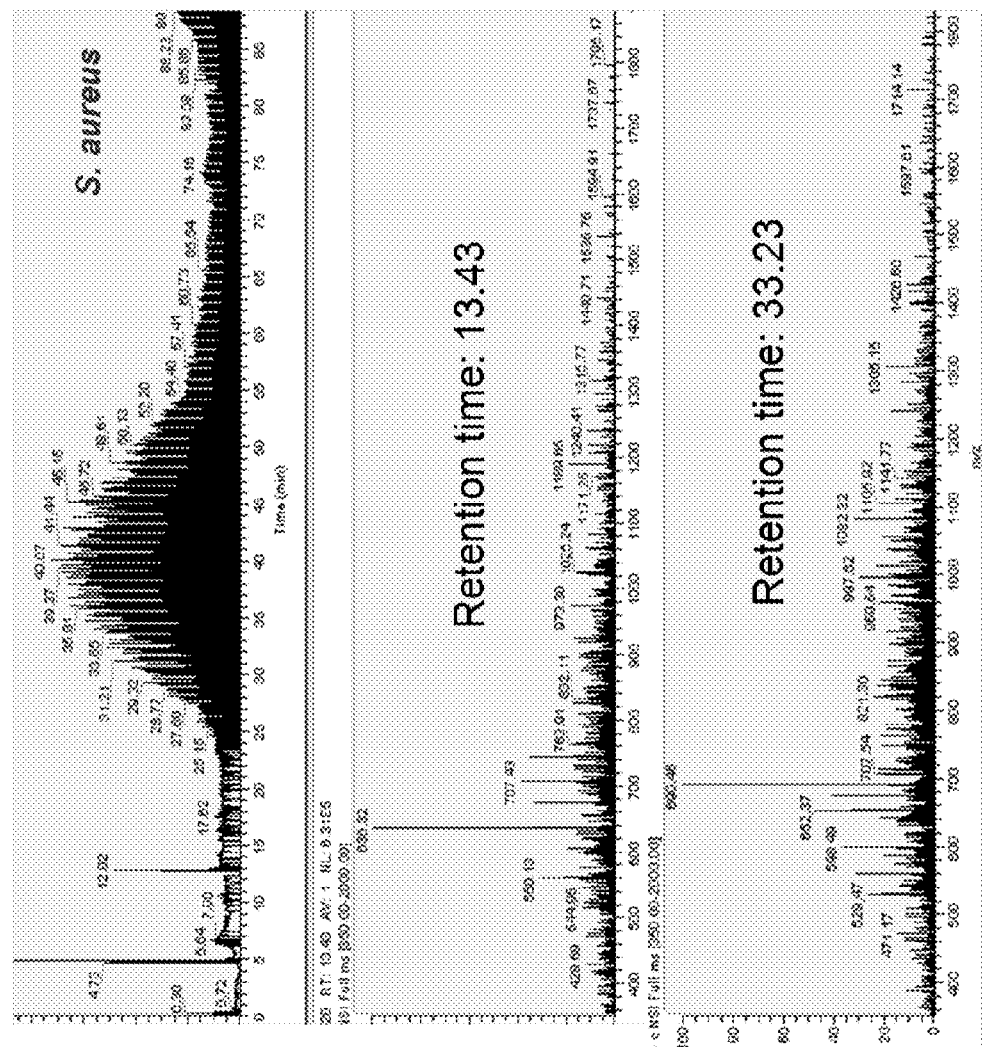
FIG. 40(A) is an HPLC chromatogram of pyrolyzed S. aureus.
FIGS. 40(B) and 40(C) are charts of the full MS scans at 13.43 and 33.23, respectively.
FIG. 40(D) is a chart of the Sequest search in a bacteria database showing the one of its possible origins is S. aureus.

The same experiment was done to bacteria *S. aureus*, and its chromatograph and full scan mass spectra at retention time 13.43 min and 33.32 min (FIG. 32) showing the peptides eluting out of column. Just like *E. coli*, the Sequest search in bacteria (FIG. 32) did give out one of its possible protein origins being *S. aureus*; however, not with a high rank (#42). Again, the peptides detected for all the proteins in the result list were not generated according to the DC cleavage rule (namely generated from cleavage before C and after D).

In summary, due to the complexity of the pyrolyzed bacteria, full ESI-MS analysis does not show any peptide peaks and thus HPLC is required prior to entering the mass spectrometer. In HPLC-ESI-MS, peptide fragments from pyrolysis are eluted from HPLC column and are detected by MS. The precursor ions and their MS/MS data are used for Sequest database searching, which shows some of the proteins are actually from the tested bacteria. However, the identified peptides by Sequest are not produced following the DC cleavage rule, because of the software's enzyme design limitation. Thus, a capable search engine is needed to perform the database search, to verify if pyrolysis can be applied for bacteria identification.

REFERENCES (1) Baldwin, M. A. *Mol. Cell. Proteomics FIELD Full Journal Title: Molecular and Cellular Proteomics FIELD Full Journal* 2004, 3, 1-9.
(2) Kellner, R. L., F.; Meyer, H. E. *Microcharacterization of Protein*, 2 ed.; Wiley-VCH: Weinheim, Germany, 1999.
(3) Corey, E. J.; Haefele, L. F. *Journal of he American Chemical Society* 1959, 81, 2225-2228.
(4) Iwasaki, H.; Cohen, O L. A.; Witkop, B. *J. Am. Chem. Soc.* 1963, 85, 3701-3702.
(5) Lewis, R. *Elastomeric Proteins* 2003, 136-151.
(6) English, R. D.; Cotter, R. J. *J. Mass Spectrom.* 2003, 38, 296-304.
(7) Yao, Z-P.; Afonso, C.; Fenselau, C. *Rapid Commun. Mass Spectrom.* 2002, 16, 1953-1956.
(8) Anhalt, J. P.; Fenselau, C. *Anal. Chem.* 1975, 47, 219-225.
(9) Meuzelaar, H. L. C.; Haverkamp, J.; Hileman, F. D. *Techniques and Instrumentation in Analytic Chemistry, Vol. 3: Pyrolysis Mass Spectrometry of Recent and Fissil Biomaterials*, 1982.
(10) DeLuca, S.; Sarver, E. W.; Harrington, P.; Voorhees, K. J. *Anal. Chem.* 1990, 62, 1465-1472.
(11) Basile, F.; Voorhees, K. J.; Hadfield, T. L. *Applied and Environmental Microbiology* 1995, 61, 1534-1539.
(12) Hendricker A. D., V. K. J. *Journal of Analytical and Applied Pyrolysis* 1996, 36, 51-70.
(13) Meetani, M.; Basile, F.; Voorhees, K. *J. Appl. Anal. Pyrolysis* 2003, 68-69, 101-113.
(14) Thomya, P.; Wesdemiotis, C.; Erdodi, G.; Kennedy, J. P., Seattle, Wash., May 29-Jun. 1, 2006 2006; American Society for Mass Spectrometry.
(15) Sato, M.; Hida, M.; Nagase, H. *Journal of analytical toxicology* 2001, 25, 304-309.
(16) Hauser, N. Ph.D. *dissertation, University of Wyoming* 2008,
(17) Yates, J. R., III; McCormack, A. L.; Eng, J. *Analytical Chemistry* 1996, 68, 534A-540A.
(18) MacCoss, M. J.; Wu, C. C.; Yates, J. R., III *Analytical Chemistry* 2002, 74, 5593-5599.

The foregoing description and drawings comprise illustrative embodiments of the present inventions. The foregoing embodiments and the methods described herein may vary based on the ability, experience, and preference of those skilled in the art. Merely listing the steps of the method in a certain order does not constitute any limitation on the order of the steps of the method. The foregoing description and drawings merely explain and illustrate the invention, and the invention is not limited thereto, except insofar as the claims are so limited. Those skilled in the art that have the disclosure before them will be able to make modifications and variations therein without departing from the scope of the invention.

We claim:

1. A method of analyzing a peptide sample containing aspartic acid and cysteine, comprising the steps of:
   (a) heating the peptide sample to between about 180° C. and about 250° C., in a period of between about 5 seconds and about 30 seconds to cleave the peptide at both the aspartic acid and cysteine site-specific locations;
   (b) electrospraying the digested sample with a solvent to produce desorbed ions of components of the digested sample; and
   (c) detecting the desorbed ions.

2. A method as described in claim 1, wherein the step of detecting the desorbed ions is by mass spectrometry.

3. A method as described in claim 1, wherein the solvent is free of cationizing agents.

4. A method as described claim 1, wherein the method is performed at atmospheric pressure.

5. Apparatus for analyzing a peptide sample containing aspartic acid and cysteine, comprising:
   (a) a heating element having a surface on which the sample is deposited and which heats the peptide sample to between about 180° C. and about 250° C., in a period of between about 5 seconds and about 30 seconds to cleave the peptide at both the aspartic acid and cysteine site-specific locations;
   (b) an electrospray device that subjects the digested sample to a solvent spray to produce desorbed ions of components of the digested sample; and
   (c) a detector for detecting the desorbed ions.

* * * * *